US007928230B2

(12) United States Patent
Wacker et al.

(10) Patent No.: US 7,928,230 B2
(45) Date of Patent: Apr. 19, 2011

(54) METHOD FOR MODULATING GPR119 G PROTEIN-COUPLED RECEPTOR AND SELECTED COMPOUNDS

(75) Inventors: Dean A. Wacker, Yardley, PA (US); Karen A. Rossi, Newton, PA (US); Ying Wang, New Hope, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 229 days.

(21) Appl. No.: 12/173,864

(22) Filed: Jul. 16, 2008

(65) Prior Publication Data
US 2009/0042919 A1    Feb. 12, 2009

Related U.S. Application Data

(60) Provisional application No. 60/950,162, filed on Jul. 17, 2007.

(51) Int. Cl.
C07D 401/00    (2006.01)
(52) U.S. Cl. ..................................... 544/324
(58) Field of Classification Search .................. 544/324; 514/272
See application file for complete search history.

(56) References Cited

U.S. PATENT DOCUMENTS

| | | | |
|---|---|---|---|
| 3,826,643 A | 7/1974 | Diehl et al. |
| 5,488,064 A | 1/1996 | Sher |
| 5,491,134 A | 2/1996 | Sher et al. |
| 5,541,204 A | 7/1996 | Sher et al. |
| 5,612,359 A | 3/1997 | Murugesan |
| 5,770,615 A | 6/1998 | Cheng et al. |
| 5,776,983 A | 7/1998 | Washburn et al. |
| 6,043,265 A | 3/2000 | Murugesan et al. |
| 6,566,384 B1 | 5/2003 | Owen et al. |
| 2003/0181420 A1 | 9/2003 | Bayne et al. |
| 2005/0080111 A1 | 4/2005 | Bayne et al. |
| 2005/0245515 A1 | 11/2005 | Dehmlow et al. |
| 2006/0155128 A1 | 7/2006 | Jones et al. |
| 2006/0292073 A1 | 12/2006 | Goodman et al. |

FOREIGN PATENT DOCUMENTS

| | | |
|---|---|---|
| EP | 1 338 651 | 8/2003 |
| WO | WO 96/38144 | 12/1996 |
| WO | WO 97/12613 | 4/1997 |
| WO | WO 97/12615 | 4/1997 |
| WO | WO 99/26659 | 6/1999 |
| WO | WO 00/01389 | 1/2000 |
| WO | WO 00/39102 | 7/2000 |
| WO | WO 02/02519 | 1/2002 |
| WO | WO 2004/065380 | 8/2004 |
| WO | WO 2004/076413 | 9/2004 |
| WO | WO 2004/089885 | 10/2004 |
| WO | WO 2005/007647 | 1/2005 |
| WO | WO 2005/007658 | 1/2005 |
| WO | WO 2005/025504 | 3/2005 |
| WO | WO 2005/089786 | 9/2005 |
| WO | WO 2005/121121 | 12/2005 |
| WO | WO 2006/067532 | 6/2006 |
| WO | WO 2006/083491 | 8/2006 |

OTHER PUBLICATIONS

Ahrén, B., "Autonomic regulation of islet hormone secretion—Implications for health and disease", Diabetologia, vol. 43, pp. 393-410 (2000).
Arbeeny, C. et al., "The Metabolic Syndrome: From Pathophysiology to Novel Treatment Strategies", Curr. Med. Chem.—Imm., Endoc. & Metab. Agents, vol. 1, No. 1, pp. 1-24 (2001).
Boger, D.L. et al., "Total Syntheses of Azafluoranthene Alkaloids: Rufescine and Imeluteine", J. Org. Chem., vol. 49, No. 21, pp. 4050-4055 (1984).
Brancati, F.L. et al., "Body Weight Patterns from 20 to 49 Years of Age and Subsequent Risk for Diabetes Mellitus", Arch. Intern. Med., vol. 159, pp. 957-963 (1999).
Bundgaard, H., Chapter 5: "Design and Application of Prodrugs", A Textbook of Drug Design and Development, Harwood Academic Publishers, publ., Krogsgaard-Larsen, P. et al., eds., pp. 113-191 (1991).
Bundgaard, H., ed., Design of Prodrugs, Elsevier Science Publishers B.V., publ. (1985) (table of contents).
Butler, A.E. et al., "β-Cell Deficit and Increased β-Cell Apoptosis in Humans with Type 2 Diabetes", Diabetes, vol. 52, pp. 102-110 (2003).
Chu, Z.-L. et al., "A Role for β-Cell-Expressed G Protein-Coupled Receptor 119 in Glycemic Control by Enhancing Glucose-Dependent Insulin Release", Endocrinology, vol. 148, No. 6, pp. 2601-2609 (2007).
Cornicelli, J.A. et al., "15-Lipoxygenase and Its Inhibition: A Novel Therapeutic Target for Vascular Disease", Current Pharmaceutical Design, vol. 5, No. 1, pp. 11-20 (1999).
Deng, H. et al., "Aryllead(IV) Reagents in Synthesis: Formation of the C11 Quaternary Center of N-Methylwelwitindolinone C Isothiocyanate", Organic Letters, vol. 3, No. 19, pp. 3001-3004 (2001).
Donetti, A. et al., "(Imidazolylphenyl)formamidines. A Structurally Novel Class of Potent Histamine $H_2$ Antagonists", J. Med. Chem., vol. 27, No. 3, pp. 380-386 (1984).
Ford, E.S. et al., "Prevalence of the Metabolic Syndrome Among US Adults", Journal of the American Medical Association, vol. 287, No. 3, pp. 356-359 (2002). Fredriksson, R. et al., "Seven evolutionary conserved human rhodopsin G protein-coupled receptors lacking close relatives", FEBS Letters, vol. 554, pp. 381-388 (2003).
Frlan, R. et al., "Recent Progress in Diaryl Ether Synthesis", Synthesis, No. 14, pp. 2271-2285 (2006).
Gennaro, A.R., ed., Remington's Pharmaceutical Sciences, 17th Edition, Mack Publishing Company, publ., p. 1418 (1985).
Gomtsyan, A. et al., "Design, Synthesis, and Structure-Activity Relationship of 6-Alkynylpyrimidines as Potent Adenosine Kinase Inhibitors", J. Med. Chem., vol. 45, No. 17, pp. 3639-3648 (2002).
Greene, T.W. et al., Protective Groups in Organic Synthesis, Second Edition, John Wiley & Sons, Inc., publ., pp. ix-x (table of contents) (1991).
Haning, H. et al., "Novel heterocyclic thyromimetics", Bioorganic & Medicinal Chemistry Letters, vol. 15, pp. 1835-1840 (2005).
Hara, S., "Ileal Na+/bile acid cotransporter inhibitors", Drugs of the Future, vol. 24, No. 4, pp. 425-430 (1999).
Hertzog, D.L., "Recent advances in the cannabinoids", Expert Opin. Ther. Patents, vol. 14, No. 10, pp. 1435-1452 (2004).
Hill, J.O. et al., "Environmental Contributions to the Obesity Epidemic", Science, vol. 280, pp. 1371-1374 (1998).
Hong, C.Y. et al., "Asymmetric Synthesis of Either Enantiomer of Opium Alkaloids and Morphinans. Total Synthesis of (−)- and (+)-Dihydrocodeinone and (−)- and (+)-Morphine", J. Am. Chem. Soc., vol. 115, No. 23, pp. 11028-11029 (1993).

(Continued)

Primary Examiner — Janet L Andres
Assistant Examiner — Heidi Reese
(74) Attorney, Agent, or Firm — Terence J. Bogie

(57) ABSTRACT

A method of modulating the activity of the GPR119 G protein-coupled receptor comprising administering to a mammalian patient in need thereof a therapeutically effective amount of at least one compound of Formula I or Formula IA and, optionally, an additional therapeutic agent.

8 Claims, No Drawings

OTHER PUBLICATIONS

Itoh, T. et al., "A General Palladium-Catalyzed Coupling of Aryl Bromides/Triflates and Thiols", Organic Letters, vol. 6, No. 24, pp. 4587-4590 (2004).

Jiang, G. et al., "Prevention of obesity in mice by antisense oligonucleotide inhibitors of stearoyl-CoA desaturase-1", The Journal of Clinical Investigation, vol. 115, No. 4, pp. 1030-1038 (2005).

Justus, K. et al., "First Synthesis of a Strained 14-Membered Biaryl Ether Lactone by Macrolactonization", Tetrahedron Letters, vol. 32, No. 14, pp. 5781-5784 (1991).

Katritzky, A.R. et al., "Efficient Transformations of Aldehydes and Ketones into One-Carbon Homologated Carboxylic Acids", Synthesis, pp. 1425-1427 (1996).

Ketcha, D.M. et al., "The Reduction of N-(phenylsulfonyl)indoles with Sodium Cyanoborohydride in Trifluoroacetic Acid", Tetrahedron Letters, vol. 30, No. 49, pp. 6833-6836 (1989).

Le Stunff, C. et al., "Early Changes in Postprandial Insulin Secretion, Not in Insulin Sensitivity, Characterize Juvenile Obesity", Diabetes, vol. 43, pp. 696-702 (1994).

Magnus, P. et al., "Studies on the Synthesis of the Antitumor Agent CC-1065. Synthesis of the Unprotected Cyclopropapyrroloindole A Portion Using the 3,3'-Bipyrrole Strategy", J. Am. Chem. Soc., vol. 109, No. 9, pp. 2706-2711 (1987).

NCBI Entrez Accession No. AAP72125 (gi:32165516), Fredriksson, R. et al., Dec. 8, 2003.

NCBI Entrez Accession No. AY288423 (gi:32165529), Fredriksson, R. et al., Dec. 8, 2003.

Nishio, T. et al., "Reduction of Indolin-2-ones and Desulfurization of Indoline-2-thiones to Indoline and Indole Derivatives", Helvetica Chimica Acta, vol. 73, pp. 1719-1723 (1990).

Norman, M.H. et al., "Structure-Activity Relationships of a Series of Pyrrolo[3,2-d]pyrimidine Derivatives and Related Compounds as Neuropeptide Y5 Receptor Antagonists", J. Med. Chem., vol. 43, No. 22, pp. 4288-4312 (2000).

Overton, H.A. et al., "Deorphanization of a G protein-coupled receptor for oleoylethanolamide and its use in the discovery of small-molecule hypophagic agents", Cell Metabolism, vol. 3, pp. 167-175 (2006).

Pedersen, O., "The Impact of Obesity on the Pathogenesis of Non-Insulin-Dependent Diabetes Mellitus: A Review of Current Hypotheses", Diabetes/Metabolism Reviews, vol. 5, No. 6, pp. 495-509 (1989).

Perry, I.J. et al., "Prospective study of risk factors for development of non-insulin dependent diabetes in middle aged British men", BMJ, vol. 310, pp. 560-564 (1995).

Prentki, M. et al., "Islet β cell failure in type 2 diabetes", The Journal of Clinical Investigation, vol. 116, No. 7, pp. 1802-1812 (2006).

Radinov, R. et al., "Lithiation of Polychloropyrimidines and Dichloropyridines", J. Org. Chem., vol. 56, No. 15, pp. 4793-4796 (1991).

Schubert, U., "The Homologation of Hagemann's Ester", Synthesis, pp. 364-365 (1978).

Sendobry, S.M. et al., "Attenuation of diet-induced atherosclerosis in rabbits with a highly selective 15-lipoxygenase inhibitor lacking significant antioxidant properties", British Journal of Pharmacology, vol. 120, pp. 1199-1206 (1997).

Sirowej, H. et al., "Preparation of substituted indoles by reduction of isatin and oxindole derivatives with diborane/tetrahydrofuran", Synthesis, No. 2, p. 84 (1972).

Soga, T. et al., "Lysophosphatidylcholine enhances glucose-dependent insulin secretion via an orphan G-protein-coupled receptor", Biochemical and Biophysical Research Communications, vol. 326, pp. 744-751 (2005).

Takahashi, K. et al., "Efficient Method for a One-Carbon Homologation of Aldehydes and Benzophenone to Carboxylic Acids", J. Org. Chem., vol. 48, No. 20, pp. 3566-3569 (1983).

Testa, B. et al., Hydrolysis in Drug and Prodrug Metabolism: Chemistry, Biochemistry, and Enzymology, Wiley-VCH GmbH & Co., publ., pp. xi-xx (table of contents) (2003).

Urgaonkar, S. et al., "Application of a New Bicyclic Triaminophosphine Ligand in Pd-Catalyzed Buchwald-Hartwig Amination Reactions of Aryl Chlorides, Bromides, and Iodides", J. Org. Chem. vol. 68, No. 22, pp. 8416-8423 (2003).

Wermuth, C.G. et al., Chapter 31: "Designing Prodrugs and Bioprecursors I: Carrier Prodrugs", The Practice of Medicinal Chemistry, Academic Press Limited, publ., Wermuth, C.G., ed., pp. 671-696 (1996).

Yang, B.H. et al., "Palladium-catalyzed amination of aryl halides and sulfonates", Journal of Organometallic Chemistry, vol. 576, pp. 125-146 (1999).

Young, S.D. et al., "L-743,726 (DMP-266): a Novel, Highly Potent Nonnucleoside Inhibitor of the Human Immunodeficiency Virus Type 1 Reverse Transcriptase", Antimicrobial Agents and Chemotherapy, vol. 39, No. 12, pp. 2602-2605 (1995).

Zhang, X. et al., "Dimethyldioxirane Oxidation of Indole Derivatives. Formation of Novel Indole-2,3-epoxides and a Versatile Synthetic Route to Indolinones and Indolines", J. Am. Chem. Soc., vol. 115, No. 19, pp. 8867-8868 (1993).

METHOD FOR MODULATING GPR119 G PROTEIN-COUPLED RECEPTOR AND SELECTED COMPOUNDS

RELATED APPLICATION

This application claims the benefit of U.S. Provisional Application No. 60/950,162, filed on Jul. 17, 2007, incorporated herein by reference in its entirety.

BACKGROUND OF THE INVENTION

Diabetes mellitus is a serious disease afflicting over 100 million people worldwide. In the United States, there are more than 12 million diabetics, with 600,000 new cases diagnosed each year. Diabetes mellitus is a diagnostic term for a group of disorders characterized by abnormal glucose homeostasis resulting in elevated blood sugar. There are many types of diabetes, but the two most common are Type 1 (also referred to as insulin-dependent diabetes mellitus or IDDM) and Type 2 (also referred to as non-insulin-dependent diabetes mellitus or NIDDM).

The etiology of the different types of diabetes is not the same; however, everyone with diabetes has two things in common: overproduction of glucose by the liver and little or no ability to move glucose out of the blood into the cells where it becomes the body's primary fuel.

People who do not have diabetes rely on insulin, a hormone made in the pancreas, to move glucose from the blood into the cells of the body. However, people who have diabetes either do not produce insulin or cannot efficiently use the insulin they produce; therefore, they cannot move glucose into their cells. Glucose accumulates in the blood creating a condition called hyperglycemia, and over time, can cause serious health problems.

Diabetes is a syndrome with interrelated metabolic, vascular, and neuropathic components. The metabolic syndrome, generally characterized by hyperglycemia, comprises alterations in carbohydrate, fat and protein metabolism caused by absent or markedly reduced insulin secretion and/or ineffective insulin action. The vascular syndrome consists of abnormalities in the blood vessels leading to cardiovascular, retinal and renal complications. Abnormalities in the peripheral and autonomic nervous systems are also part of the diabetic syndrome.

Diabetes has also been implicated in the development of kidney disease, eye diseases and nervous-system problems. Kidney disease, also called nephropathy, occurs when the kidney's "filter mechanism" is damaged and protein leaks into urine in excessive amounts and eventually the kidney fails. Diabetes is also a leading cause of damage to the retina at the back of the eye and increases risk of cataracts and glaucoma. Finally, diabetes is associated with nerve damage, especially in the legs and feet, which interferes with the ability to sense pain and contributes to serious infections. Taken together, diabetes complications are one of the nation's leading causes of death.

Many people with NIDDM have sedentary lifestyles and are obese; they weigh approximately 20% more than the recommended weight for their height and build. Furthermore, obesity is characterized by hyperinsulinemia and insulin resistance, a feature shared with NIDDM, hypertension and atherosclerosis.

Obesity, which is the result of an imbalance between caloric intake and energy expenditure, is highly correlated with insulin resistance and diabetes in experimental animals and human. However, the molecular mechanisms that are involved in obesity-diabetes syndromes are not clear. During early development of obesity, increased insulin secretion balances insulin resistance and protects patients from hyperglycemia (Le Stunff et al., *Diabetes,* 43:696-702 (1989)). However, over time, β-cell function deteriorates and non-insulin-dependent diabetes develops in about 20% of the obese population (Pederson, P., *Diab. Metab. Rev.,* 5:505-509 (1989)) and (Brancati, F. L. et al., *Arch. Intern. Med.,* 159: 957-963 (1999)). Given its high prevalence in modern societies, obesity has thus become the leading risk factor for NIDDM (Hill, J. O. et al., *Science,* 280:1371-1374 (1998)). However, the factors which predispose a fraction of patients to alteration of insulin secretion in response to fat accumulation remain unknown. The most common diseases with obesity are cardiovascular disease (particularly hypertension), diabetes (obesity aggravates the development of diabetes), gall bladder disease (particularly cancer) and diseases of reproduction. Research has shown that even a modest reduction in body weight can correspond to a significant reduction in the risk of developing coronary heart disease.

Obesity considerably increases the risk of developing cardiovascular diseases as well. Coronary insufficiency, atheromatous disease, and cardiac insufficiency are at the forefront of the cardiovascular complication induced by obesity. It is estimated that if the entire population had an ideal weight, the risk of coronary insufficiency would decrease by 25% and the risk of cardiac insufficiency and of cerebral vascular accidents by 35%. The incidence of coronary diseases is doubled in subjects less than 50 years of age who are 30% overweight. The diabetes patient faces a 30% reduced lifespan. After age 45, people with diabetes are about three times more likely than people without diabetes to have significant heart disease and up to five times more likely to have a stroke. These findings emphasize the inter-relations between risks factors for NIDDM, obesity and coronary heart disease as well as the potential value of an integrated approach involving the treatment of both obesity and diabetes (Perry, I. J. et al., *BMJ,* 310:560-564 (1995)).

Type 2 diabetes results from the progressive loss of pancreatic β-cell function in the presence of insulin resistance, leading to an overall reduction in insulin output (Prentki, M. et al., "Islet failure in type 2 diabetes", *J. Clin. Invest.,* 116: 1802-1812 (2006)). β-cells are the cell type that store and release insulin in response to an elevation in plasma glucose or in response to hormonal signals from the gut following the ingestion of food. Evidence suggests that in type 2 diabetics the rate of β-cell cell death (apoptosis) exceeds that of new β-cell development, yielding an overall loss in β-cell number (Butler, A. E. et al., "β-cell deficit and increased β-cell apoptosis in humans with type 2 diabetes", *Diabetes,* 52:102-110 (2003)). β-cell apoptosis may arise from persistent elevations in plasma glucose levels (glucotoxicity) and/or plasma lipid levels (lipotoxicity).

G-protein coupled receptors (GPCRs) expressed on β-cells are known to modulate the release of insulin in response to changes in plasma glucose levels (Abren, B., "Autonomic regulation of islet hormone secretion—Implications for health and disease", *Diabetologia,* 43:393-410 (2003)). Those GPCRs specifically coupled to the elevation of cAMP via the $G_s$ alpha subunit of G-protein, have been shown to enhance glucose-stimulated insulin release from β-cells. Cyclic AMP-stimulating GPCRs on β-cells include the GLP-1, GIP, β2-adrenergic receptors and GPR119. Increasing cAMP concentration in β-cells is known to lead to the activation of PKA which is thought to prevent the opening of potassium channels on the surface of the β-cell. The reduction in K⁺ efflux depolarizes the β-cell leading to an influx of Ca⁺⁺ which promotes the release of insulin.

GPR119 (e.g., human GPR119, GenBank® Accession No. AAP72125 and alleles thereof; e.g., mouse GPR119, GenBank® Accession No. AY288423 and alleles thereof) is a GPCR located at chromosome position Xp26.1 (Fredriksson, R. et al., "Seven evolutionarily conserved human rhodopsin G protein-coupled receptors lacking close relatives", *FEBS Lett.*, 554:381-388 (2003)). The receptor is coupled to Gs, and when stimulated, produces an elevation in cAMP in a variety of cell types including β-cell-derived insulinomas (Soga, T. et al., "Lysophosphatidylcholine enhances glucose-dependent insulin secretion via an orphan G-protein-coupled receptor", *Biochem. Biophys. Res. Comm.*, 326:744-751 (2005), International Applications WO 04/065380, WO 04/076413, WO 05/007647, WO 05/007658, WO 05/121121, WO 06/083491, and EP 1338651). The receptor has been shown to be localized to the β-cells of the pancreas in a number of species as well as in specific cell types of the gastrointestinal tract. Activation of GPR119, with agonist ligands such as lysophosphatidylcholine, produce a glucose dependent increase in insulin secretion from primary mouse islets and various insulinoma cell lines such as NIT-1 and HIT-T15 (Soga, T. et al., "Lysophosphatidylcholine enhances glucose-dependent insulin secretion via an orphan O-protein-coupled receptor", *Biochem. Biophys. Res. Comm.*, 326:744-751 (2005); Chu, Z. L. et al., "A role for β-cell-expressed GPR119 in glycemic control by enhancing glucose-dependent insulin release", *Endocrinology*, doi: 10.1210/en.2006-1608 (2007)).

When activators of GPR119 are administered to either normal mice or mice that are prone to diabetes due to genetic mutation, prior to an oral glucose tolerance test, improvements in glucose tolerance are observed. A short-lived increase in plasma glucagon-like peptide-1 and plasma insulin levels are also observed in these treated animals (Chu, Z. L. et al., "A role for β-cell-expressed GPR119 in glycemic control by enhancing glucose-dependent insulin release", *Endocrinology*, doi:10.1210/en.2006-1608 (2007)). In addition to effects on plasma glucose levels, GPR119 activators have also been demonstrated to produce reductions in acute food intake and to reduce body weight in rats following chronic administration (Overton, H. A. et al., "Deorphanization of a G protein-coupled receptor for oleoylethanolamide and its use in the discovery of small-molecule hypophagic agents", *Cell Metabolism*, 3:167-175 (2006), and patent applications WO 05/007647 and WO 05/007658).

SUMMARY OF THE INVENTION

In accordance with the present invention, a method for modulating the GPR119 G protein-coupled receptor is described as applied to the compounds of Formula I and IA. In addition, a selected group of compounds are also disclosed for the same utility.

The method described herein is focused on the use of compounds of Formula I and IA to modulate the GPR 119 receptor, for example agonists of the GPR119 receptor Consequently, the compounds of the present invention may be used in the treatment of multiple diseases or disorders associated with GPR119, such as diabetes and related conditions, microvascular complications associated with diabetes, the macrovascular complications associated with diabetes, cardiovascular diseases, Metabolic Syndrome and its component conditions, obesity and other maladies. Examples of diseases or disorders associated with the modulation of the GPR119 G protein-coupled receptor that can be prevented, modulated, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis and its sequelae, abnormal heart function, myocardial ischemia, stroke, Metabolic Syndrome, hypertension, obesity, dislipidemia, dyslipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy and glaucoma.

More particularly, the present invention relates to methods of modulating the activity of the GPR119 G protein-coupled receptor comprising administering to a mammalian patient, for example, a human patient, in need thereof a therapeutically effective amount of a compound of the present invention, alone, or optionally, in combination with another compound of the present invention and/or at least one other type of therapeutic agent.

Even more particularly, the present invention relates to a method for preventing, modulating, or treating the progression or onset of diseases or disorders associated with the activity of the GPR119 G protein-coupled receptor comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

Examples of diseases or disorders associated with the activity of the GPR119 G protein-coupled receptor that can be prevented, modulated, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis and its sequelae, abnormal heart function, myocardial ischemia, stroke, Metabolic Syndrome, hypertension, obesity, dislipidemia, dyslipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy and glaucoma.

The present invention relates to a method for preventing, modulating, or treating the progression or onset of diabetes, hyperglycemia, obesity, dyslipidemia, hypertension and cognitive impairment comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

The present invention relates to a method for preventing, modulating, or treating the progression or onset of diabetes, comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

The present invention relates to a method for preventing, modulating, or treating the progression or onset of hyperglycemia comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

The present invention relates to a method for preventing, modulating, or treating the progression or onset of obesity comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

For example, the present invention relates to a method for preventing, modulating, or treating the progression or onset of dyslipidemia comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

In another example, the present invention relates to a method for preventing, modulating, or treating the progression or onset of hypertension comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

In a special combination, the present invention relates to the use of a formulated product wherein the selected formulation is made by combining (a) a compound of Formula I and/or IA (using any of the compound embodiments listed herein) and (b) a dipeptidyl peptidase-IV (DPP4) inhibitor.

The compounds of Formula I and IA can be administered for any of the uses described herein by any suitable means, for example, orally, such as in the form of tablets, capsules, granules or powders; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents.

In carrying out the method of the invention for treating diabetes and related diseases, a pharmaceutical composition will be employed containing the compounds of formula I, with or without other antidiabetic agent(s) and/or antihyperlipidemic agent(s) and/or other type therapeutic agents in association with a pharmaceutical vehicle or diluent. The pharmaceutical composition can be formulated employing conventional solid or liquid vehicles or diluents and pharmaceutical additives of a type appropriate to the mode of desired administration, such as pharmaceutically acceptable carriers, excipients, binders, and the like. The compounds can be administered to a mammalian patient, including humans, monkeys, dogs, etc. by an oral route, for example, in the form of tablets, capsules, beads, granules or powders. The dose for adults is preferably between 1 and 2,000 mg per day, which can be administered in a single dose or in the form of individual doses from 1-4 times per day.

A typical capsule for oral administration contains one or more compounds of Formula I or Formula IA (250 mg), lactose (75 mg), and magnesium stearate (15 mg). The mixture is passed through a 60 mesh sieve and packed into a No. 1 gelatin capsule.

A typical injectable preparation is produced by aseptically placing 250 mg of one or more compounds of Formula I or Formula IA into a vial and then aseptically freeze-drying and sealing. For use, the contents of the vial are mixed with 2 mL of physiological saline to produce an injectable preparation.

The method of this invention comprises the administration of a compound of Formula I or Formula IA or mixtures thereof:

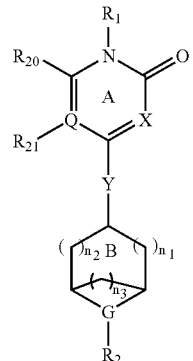

Formula I

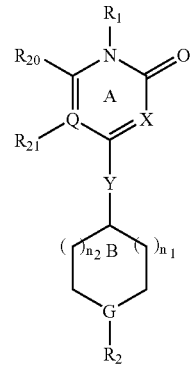

Formula IA wherein $n_1$, $n_2$, $n_3$, G, Q, X, $R_1$, $R_2$, $R_{20}$ and $R_{21}$ are defined below.

Compounds used in the method of the present invention modulate the activity of G protein-coupled receptors. Preferably, compounds of the present invention modulate the activity of the GPR119 G protein-coupled receptor ("GPR119"). Consequently, the compounds of the present invention may be used in the treatment of multiple diseases or disorders associated with GPR119, such as diabetes and related conditions, microvascular complications associated with diabetes, the macrovascular complications associated with diabetes, cardiovascular diseases, Metabolic Syndrome and its component conditions, obesity and other maladies. Examples of diseases or disorders associated with the modulation of the GPR119 G protein-coupled receptor that can be prevented, modulated, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis and its sequelae, abnormal heart function, myocardial ischemia, stroke, Metabolic Syndrome, hypertension, obesity, dislipidemia, dyslipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy and glaucoma.

In addition, the present invention relates to a formulated product wherein the selected formulation is made by using a compound of Formula I and/or IA as the only active ingredient or by combining (a) a compound of Formula I and/or IA (using any of the compound embodiments listed herein) and (b) an additional active ingredient, for example, dipeptidyl peptidase-IV (DPP4) inhibitor (for example, a member selected from saxagliptin, sitagliptin, vildagliptin and alogliptin).

The present invention provides for compounds of Formula I and IA, pharmaceutical compositions employing such compounds, and for methods of using such compounds. In particular, the present invention provides a pharmaceutical composition comprising a therapeutically effective amount of a compound of Formula I and/or IA, alone or in combination with a pharmaceutically acceptable carrier.

Further, in accordance with the present invention, a method is provided for preventing, modulating, or treating the progression or onset of diseases or disorders associated with the activity of the GPR119 G protein-coupled receptor, such as defined above and hereinafter, wherein a therapeutically effective amount of a compound of formula I is administered to a mammalian, i.e., human, patient in need of treatment.

The compounds of the invention can be used alone, in combination with other compounds of the present invention, or in combination with one or more other agent(s).

Further, the present invention provides a method for preventing, modulating, or treating the diseases as defined above and hereinafter, wherein a therapeutically effective amount of a combination of a compound of Formula I and/or IA and another compound of Formula I or IA and/or at least one other type of therapeutic agent, is administered to a mammalian, i.e., human, patient in need of treatment.

DESCRIPTION OF THE INVENTION

A method of modulating the activity of the GPR119 G protein-coupled receptor comprising administering to a mammalian patient in need thereof a therapeutically effective amount of at least one compound of Formula I or Formula IA and, optionally, an additional therapeutic agent wherein the compound of Formula I or Formula IA is selected from:

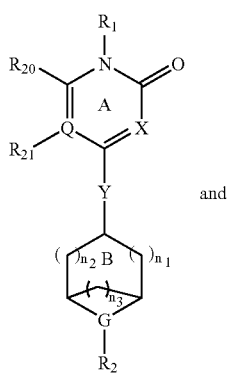

Formula I and

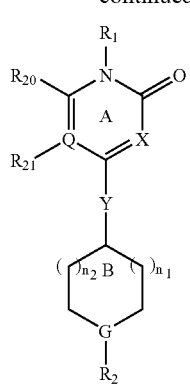

Formula IA including enantiomers, diastereomers, solvates and salts thereof (particularly enantiomers, diastereomers and pharmaceutically acceptable salts thereof) having ring A and ring B, wherein:

ring A is optionally substituted with one or more R's shown as $R_{20}$ and $R_{21}$;

G is CH or N;

Q is C or N;

X is CH or N, provided that Q and X are not both N;

Y is $CH_2$, $N(R_3)$, $C(=O)$, O, $OCR_9R_9$, S, $S(=O)$ or $S(O)_2$;

$n_1$ is 0-2;

$n_2$ is 0-2;

$n_3$ is 1-2;

$R_1$ is a 6-membered monocyclic aryl, a 5-membered monocyclic heteroaryl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1c}$, $R_{1d}$ and $R_{1e}$ are each independently selected from the group consisting of hydrogen, alkyl, alkenyl, alkynyl, cycloalkyl, aryl, heteroaryl, heterocyclyl, halo, $-NH_2$, $-CN$, $-NO_2$, $-C(=O)OH$, $-C(=O)OR_{10}$, $-OCF_3$, $-OR_{10}$, $-OH$, $-SH$, $-SR_{10}$, $-S(O)_3H$, $-P(O)_3H_2$, $-C(=O)NR_9R_9$, $-NR_9R_9$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{10}$, $-NR_9C(=O)H$, $-NR_9C(=O)R_{10}$, $-O(=O)R_{10}$, $-OC(=O)NR_9R_9$, $-C(=NR_{14})NR_9R_9$, $-NHC(=NR_{14})NR_{14}R_{14}$, $-S(=O)R_{10}$, $-S(O)_2R_{10}$, $-NR_9C(=O)OR_8$ and $-NR_9S(O_2)R_8$, wherein the alkyl alkenyl, alkynyl, cycloalkyl, aryl, heteroaryl and heterocyclyl may each be optionally substituted with one or more $R_6$'s; provided that at least one of $R_{1a}$, $R_{1b}$, $R_{1c}$, $R_{1d}$ and $R_{1e}$ is heteroaryl;

$R_2$ is cycloalkyl, aryl, heteroaryl, heterocyclyl, $-S(O)_2R_5$, $-C(=O)NR_3R_5$, $-C(=O)R_5$ or $-C(=O)OR_5$, wherein the cycloalkyl, aryl, heteroaryl and heterocyclyl may each be optionally substituted with one or more $R_6$'s;

$R_3$ is hydrogen, alkyl, alkoxy, cycloalkyl, aryl, arylalkyl, heteroaryl, heteroarylalkyl, heterocyclyl or heterocyclylalkyl, wherein the heteroaryl, heteroarylalkyl, heterocyclyl and heterocyclylalkyl may each contain 1-4 heteroatoms selected from N, O and S;

$R_5$ is alkyl, alkenyl, aryl, cycloalkyl, heteroaryl or heterocyclyl, each of which may be optionally substituted with one or more $R_6$'s;

$R_6$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, $-NH_2$, $-CN$, $-NO_2$, $-C(=O)OH$, $-C(=O)OR_{10}$, $-OCF_3$, $-OR_{10}$, $-OH$, $-SH$, $-SR_{10}$, $-S(O)_3H$, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R$_{9a}$;

R$_8$, at each occurrence, is independently selected from the group consisting of alkyl, aryl, cycloalkyl, heteroaryl and heterocyclyl, each of which may be optionally substituted with one or more R$_{8a}$'s;

R$_{8a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$ R$_{14}$, =O, —NR$_{14}$C(=O)OR$_{14}$ and —NR$_{14}$S(O$_2$)R$_{14}$;

R$_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 R$_{9a}$, and the heteroaryl, heteroarylalkyl, heterocyclyl and heterocyclylalkyl each contain 1-4 heteroatoms selected from N, O and S;

R$_{9a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$, =O and arylalkyl;

R$_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 R$_{10a}$, and the heteroaryl, heteroarylalkyl, heterocyclyl and heterocyclylalkyl each contain 1-4 heteroatoms selected from N, O and S;

R$_{10a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$ R$_{14}$, —NR$_{14}$C(=O)OR$_8$, —NR$_{14}$S(O$_2$)R$_8$ and arylalkyl;

R$_{14}$, at each occurrence, is independently selected from hydrogen, alkyl, cycloalkyl and aryl; and R$_{20}$ and R$_{21}$ are each independently selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

The terms "Formula I" and "Formula IA" and all embodiments thereof shall include enantiomers, diastereomers, solvates and salts thereof (particularly enantiomers, diastereomers and pharmaceutically acceptable salts thereof).

In a second embodiment, a method of modulating the activity of the GPR119 G protein-coupled receptor wherein for the compound of Formula I or Formula IA:

ring A is optionally substituted with one or more R's shown as R$_{20}$ and R$_{21}$;

G is CH or N;

Q is C or N;

X is CH or N, provided that Q and X are not both N;

Y is CH$_2$, N(R$_3$), C(=O), O, OCR$_9$R$_9$, S, S(=O) or S(O)$_2$;

n$_1$ is 0-2;

n$_2$ is 0-2;

n$_3$ is 1-2;

R$_1$ is a 6-membered monocyclic aryl or a 6-membered monocyclic heteroaryl, each of which may be optionally substituted with one or more members selected from R$_{1a}$, R$_{1b}$, R$_{1c}$, R$_{1d}$ and R$_{1e}$;

R$_{1a}$, R$_{1b}$, R$_{1c}$, R$_{1d}$ and R$_{1e}$ are each independently selected from the group consisting of hydrogen, alkyl, alkenyl, alkynyl, cycloalkyl, aryl, heteroaryl, heterocyclyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ and —NR$_9$S(O$_2$)R$_8$, wherein the alkyl alkenyl, alkynyl, cycloalkyl, aryl, heteroaryl and heterocyclyl may each be optionally substituted with one or more R$_6$'s; provided that at least one of R$_{1a}$, R$_{1b}$, R$_{1c}$, R$_{1d}$ and R$_{1e}$ is heteroaryl;

R$_2$ is cycloalkyl, aryl, heteroaryl, heterocyclyl, —S(O)$_2$R$_5$, —C(=O)NR$_3$R$_5$, —C(=O)R$_5$ or —C(=O)OR$_5$, wherein the cycloalkyl, aryl, heteroaryl and heterocyclyl may each be optionally substituted with one or more R$_6$'s;

R$_3$ is hydrogen, alkyl, alkoxy, cycloalkyl, aryl, arylalkyl, heteroaryl, heteroarylalkyl, heterocyclyl or heterocyclylalkyl;

R$_5$ is alkyl, alkenyl, aryl, cycloalkyl, heteroaryl or heterocyclyl, each of which may be optionally substituted with one or more R$_6$'s;

R$_6$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —$NR_9C(=O)OR_8$ and —$NR_9S(O_2)R_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_8$, at each occurrence, is independently selected from the group consisting of alkyl, aryl, cycloalkyl, heteroaryl and heterocyclyl, each of which may be optionally substituted with one or more $R_{8a}$'s;

$R_{8a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —$NH_2$, —CN, —$NO_2$, —$C(=O)OH$, —$C(=O)OR_{14}$, —$OCF_3$, —$OR_{14}$, —OH, —SH, —$SR_{14}$, —$S(O)_3H$, —$P(O)_3H_2$, —$C(=O)NR_{14}R_{14}$, —$NR_{14}R_{14}$, —$S(O)_2NR_{14}R_{14}$, —$NR_{14}S(O)_2CF_3$, —$C(=O)NR_{14}S(O)_2R_{14}$, —$S(O)_2NR_{14}C(=O)R_{14}$, —$S(O)_2NR_{14}C(=O)NR_{14}R_{14}$, —$C(=O)NR_{14}S(O)_2CF_3$, —$C(=O)R_{14}$, —$NR_{14}C(=O)H$, —$NR_{14}C(=O)R_{14}$, —$OC(=O)R_{14}$, —$C(=NR_{14})NR_{14}R_{14}$, —$NHC(=NR_{14})NR_{14}R_{14}$, —$S(=O)R_{14}$, —$S(O)_2R_{14}$, =O, —$NR_{14}C(=O)OR_{14}$ and —$NR_{14}S(O)_2R_{14}$;

$R_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 $R_{9a}$;

$R_{9a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —$NH_2$, —CN, —$NO_2$, —$C(=O)OH$, —$C(=O)OR_{14}$, —$OCF_3$, —$OR_{14}$, —OH, —SH, —$SR_{14}$, —$S(O)_3H$, —$P(O)_3H_2$, —$C(=O)NR_{14}R_{14}$, —$NR_{14}R_{14}$, —$S(O)_2NR_{14}R_{14}$, —$NR_{14}S(O)_2CF_3$, —$C(=O)NR_{14}S(O)_2R_{10}$, —$S(O)_2NR_{14}C(=O)R_{10}$, —$S(O)_2NR_{14}C(=O)NR_{14}R_{14}$, —$C(=O)NR_{14}S(O)_2CF_3$, —$C(=O)R_{14}$, —$NR_{14}C(=O)H$, —$NR_{14}C(=O)R_{14}$, —$OC(=O)R_{14}$, —$C(=NR_{14})NR_{14}R_{14}$, —$NHC(=NR_{14})NR_{14}R_{14}$, —$S(=O)R_{14}$, —$S(O)_2R_{14}$, —$NR_{14}C(=O)OR_8$, —$NR_{14}S(O_2)R_8$, =O and arylalkyl;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may be optionally substituted with 0-3 $R_{10a}$;

$R_{10a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —$NH_2$ —CN, —$NO_2$, —$C(=O)OH$, —$C(=O)OR_{14}$, —$OCF_3$, —$OR_{14}$, —OH, —SH, —$SR_{14}$, —$S(O)_3H$, —$P(O)_3H_2$, —$C(=O)NR_{14}R_{14}$, —$NR_{14}R_{14}$, —$S(O)_2NR_{14}R_{14}$, —$NR_{14}S(O)_2CF_3$, —$C(=O)NR_{14}S(O)_2R_9$, —$S(O)_2NR_{14}C(=O)OR_9$, —$S(O)_2NR_{14}C(=O)NR_{14}R_{14}$, —$C(=O)NR_{14}S(O)_2CF_3$, —$C(=O)R_{14}$, —$NR_{14}C(=O)H$, —$NR_{14}C(=O)R_{14}$, —$OC(=O)R_{14}$, —$C(=NR_{14})NR_{14}R_{14}$, —$NHC(=NR_{14})NR_{14}R_{14}$, —$S(=O)R_{14}$, —$S(O)_2R_{14}$, —$NR_{14}C(=O)OR_8$, —$NR_{14}S(O_2)R_8$ and aryl alkyl;

$R_{14}$, at each occurrence, is independently selected from hydrogen, alkyl, cycloalkyl and aryl; and $R_{20}$ and $R_{21}$ are each independently selected from the group consisting of hydrogen, alkyl, haloalkyl, cycloalkyl, halo, —CN, —$C(=O)OH$, —$C(=O)OR_{10}$, —$OCF_3$, —$OR_{10}$, —OH, —$C(=O)NR_9R_9$, —$C(=O)R_{10}$ and —$OC(=O)R_{10}$.

In a third embodiment, a method of modulating the activity of the GPR119 G protein-coupled receptor wherein for the compound of Formula I or Formula IA:

ring A is optionally substituted with one or more R's shown as $R_{20}$ and $R_{21}$;

G is CH or N;

Q is C or N;

X is CH or N, provided that Q and X are not both N;

Y is $CH_2$, $N(R_3)$, $C(=O)$, O, $OCR_9R_9$, S, $S(=O)$ or $S(O)_2$;

$n_1$ is 0-2;

$n_2$ is 0-2;

$n_3$ is 1-2;

$R_1$ is phenyl, pyridinyl, pyrazinyl or pyrimindinyl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1c}$, $R_{1d}$ and $R_{1e}$ are each independently selected from the group consisting of hydrogen, alkyl, alkenyl, alkynyl, cycloalkyl, aryl, heteroaryl, heterocyclyl, halo, —$NH_2$, —CN, —$NO_2$, —$C(=O)OH$, —$C(=O)OR_{10}$, —$OCF_3$, —$OR_{10}$, —OH, —SH, —$SR_{10}$, —$S(O)_3H$, —$P(O)_3H_2$, —$C(=O)NR_9R_9$, —$NR_9R_9$, —$S(O)_2NR_9R_9$, —$NR_9S(O)_2CF_3$, —$C(=O)NR_9S(O)_2R_9$, —$S(O)_2NR_9C(=O)OR_9$, —$S(O)_2NR_9C(=O)NR_9R_9$, —$C(=O)NR_9S(O)_2CF_3$, —$C(=O)R_{10}$, —$NR_9C(=O)H$, —$NR_9C(=O)R_{10}$, —$OC(=O)R_{10}$, —$OC(=O)NR_9R_9$, —$C(=NR_{14})NR_9R_9$, —$NHC(=NR_{14})NR_{14}R_{14}$, —$S(=O)R_{10}$, —$S(O)_2R_{10}$, —$NR_9C(=O)OP$, and —$NR_9S(O_2)R_8$, wherein the alkyl alkenyl, alkynyl, cycloalkyl, aryl, heteroaryl and heterocyclyl may each be optionally substituted with one or more $R_6$'s; provided that at least one of $R_{1a}$, $R_{1b}$, $R_{1c}$, $R_{1d}$ and $R_{1e}$ is heteroaryl;

$R_2$ is cycloalkyl, aryl, heteroaryl, heterocyclyl, —$S(O)_2R_5$, —$C(=O)NR_3R_5$, —$C(=O)R_5$ or —$C(=O)OR_5$, wherein the cycloalkyl, aryl, heteroaryl and heterocyclyl may each be optionally substituted with one or more $R_6$'s;

$R_3$ is hydrogen, alkyl, alkoxy, cycloalkyl, aryl, arylalkyl, heteroaryl, heteroarylalkyl, heterocyclyl or heterocyclylalkyl;

$R_5$ is alkyl, alkenyl, aryl, cycloalkyl, heteroaryl or heterocyclyl, each of which may be optionally substituted with one or more $R_6$'s;

$R_6$, at each occurrence, is independently selected from alkyl, haloalkyl, aryl, alkenyl, alkynyl, cycloalkyl, cycloalkyl alkyl heteroaryl, heteroarylalkyl, heterocyclyl, heterocyclyl alkyl, halo, —$NH_2$, —CN, —$NO_2$, —$C(=O)OH$, —$C(=O)OR_{10}$, —$OCF_3$, —$O_{10}$, —OH, —SH, —$SR_{10}$, —$S(O)_3H$, —$P(O)_3H_2$, —$C(=O)NR_9R_9$, —$NR_9R_9$, —$S(O)_2NR_9R_9$, —$NR_9S(O)_2CF_3$, —$C(=O)N_9S(O)_2R_9$, —$S(O)_2NR_9C(=O)OR_9$, —$S(O)_2NR_9C(=O)NR_9R_9$, —$C(=O)NR_9S(O)_2CF_3$—$C(=O)R_{10}$, —$NR_9C(=O)H$, —$NR_9C(=O)R_{10}$, —$OC(=O)R_{10}$, —$C(=NR_{14})NR_9R_9$, —$NHC(=NR_{14})NR_{14}R_{14}$, —$S(=O)R_{10}$, —$S(O)_2R_{10}$, =O, —$NR_9C(=O)OR_8$ and —$NR_9S(O_2)R_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_8$, at each occurrence, is independently selected from the group consisting of alkyl, aryl, cycloalkyl, heteroaryl and heterocyclyl, each of which may be optionally substituted with one or more $R_{8a}$'s;

$R_{8a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —$NH_2$, —CN, —$NO_2$, —$C(=O)OH$, —$C(=O)OR_{14}$, —$OCF_3$, —$OR_{14}$, —OH, —SH, —$SR_{14}$, —$S(O)_3H$, —$P(O)_3H_2$, —$C(=O)NR_{14}R_{14}$, —$NR_{14}R_{14}$, —$S(O)_2NR_{14}R_{14}$, —$NR_{14}S(O)_2CF_3$, —$C(=O)NR_{14}S(O)_2R_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$ R$_{14}$, =O, —NR$_{14}$C(=O)OR$_{14}$ and —NR$_{14}$S(O)$_2$ R$_{14}$;

R$_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 R$_{9a}$;

R$_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)O, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O)$_2$R$_9$, =O and arylalkyl;

R$_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 R$_{10a}$;

R$_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$ R$_{14}$, —NR$_{14}$C(=O)OR$_8$, —NR$_{14}$S(O)$_2$R$_8$ and arylalkyl;

R$_{14}$, at each occurrence, is independently selected from hydrogen, alkyl, cycloalkyl and aryl; and R$_{20}$ and R$_{21}$ are each independently selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

In a fourth embodiment, a method of modulating the activity of the GPR119 G protein-coupled receptor wherein for the compound of Formula I or Formula IA:

ring A is optionally substituted with one or more R's shown as R$_{20}$ and R$_{21}$;
G is CH or N;
Q is C or N;
X is CH or N, provided that Q and X are not both N;
Y is CH$_2$, N(R$_3$), C(=O), O, OCR$_9$R$_9$, S, S(=O) or S(O)$_2$;
n$_1$ is 0-2;
n$_2$ is 0-2;
n$_3$ is 1-2;
R$_1$ is phenyl or pyridinyl, each of which may be optionally substituted with one or more members selected from R$_{1a}$, R$_{1b}$, R$_{1c}$, R$_{1d}$ and R$_{1e}$;

R$_{1a}$, R$_{1b}$, R$_{1c}$, R$_{1d}$ and R$_{1e}$ are each independently selected from the group consisting of hydrogen, alkyl, alkenyl, alkynyl, cycloalkyl, aryl, heteroaryl, heterocyclyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)N>S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$—C(=O)R$_{10}$, —NR$_9$C(O)N, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OC and —NR$_9$S(O)$_2$R$_8$, wherein the alkyl alkenyl, alkynyl, cycloalkyl, aryl, heteroaryl and heterocyclyl may each be optionally substituted with one or more R$_6$'s; provided that at least one of R$_{1a}$, R$_{1b}$, R$_{1c}$, R$_{1d}$ and R$_{1e}$ is heteroaryl;

R$_2$ is cycloalkyl, aryl, heteroaryl, heterocyclyl, —S(O)$_2$R$_5$, —C(=O)NR$_3$R$_5$, C(=O)R$_5$ or —C(=O)OR$_5$, wherein the cycloalkyl, aryl, heteroaryl and heterocyclyl may each be optionally substituted with one or more R$_6$'s;

R$_3$ is hydrogen, alkyl, alkoxy, cycloalkyl, aryl, arylalkyl, heteroaryl, heteroarylalkyl, heterocyclyl or heterocyclylalkyl;

R$_5$ is alkyl, alkenyl, aryl, cycloalkyl, heteroaryl or heterocyclyl, each of which may be optionally substituted with one or more R$_6$'s;

R$_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$ CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O)$_2$R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R$_{9a}$;

R$_8$, at each occurrence, is independently selected from the group consisting of alkyl, aryl, cycloalkyl, heteroaryl and heterocyclyl, each of which may be optionally substituted with one or more R$_{8a}$'s;

R$_{8a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$ R$_{14}$, =O, —NR$_{14}$C(=O)OR$_{14}$ and —NR$_{14}$S(O)$_2$ R$_{14}$;

R$_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 R$_{9a}$;

R$_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclyl alkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=N$_{14}$)NR$_{14}$R$_{14}$, —S(=O)R$_{14}$, —S(O)$_2$R$_{14}$, —NR$_{14}$C(=O)OR$_9$, —NR$_{14}$S(O$_2$)R$_8$, =O and arylalkyl;

R$_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 R$_{10a}$;

R$_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$—CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ and aryl alkyl;

R$_{14}$, at each occurrence, is independently selected from hydrogen, alkyl, cycloalkyl and aryl; and R$_{20}$ and R$_{21}$ are each independently selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

In a fifth embodiment, a method of modulating the activity of the GPR119 G protein-coupled receptor wherein for the compound of Formula I or Formula IA:

ring A is optionally substituted with one or more R's shown as R$_{20}$ and R$_{21}$;
G is CH or N;
Q is C or N;
X is CH or N, provided that Q and X are not both N;
Y is CH$_2$, N(R$_3$), C(=O), O, OCR$_9$R$_9$, S, S(=O) or S(O)$_2$;
n$_1$ is 0-2;
n$_2$ is 0-2;
n$_3$ is 1-2;
R$_1$ is

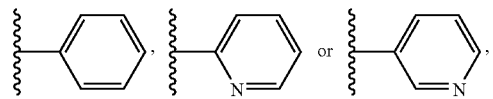

each of which may be optionally substituted with one or more members selected from the group consisting of R$_{1a}$, R$_{1b}$, R$_{1c}$, R$_{1d}$ and R$_{1e}$;

R$_{1a}$, R$_{1b}$, R$_{1c}$, R$_{1d}$ and R$_{1e}$ are each independently selected from the group consisting of hydrogen, alkyl, alkenyl, alkynyl, cycloalkyl, aryl, heteroaryl, heterocyclyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$R$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_9$ and —NR$_9$S(O$_2$)R$_8$, wherein the alkyl alkenyl, alkynyl, cycloalkyl, aryl, heteroaryl and heterocyclyl may each be optionally substituted with one or more R$_6$'s; provided that at least one of R$_{1a}$, R$_{1b}$, R$_{1c}$, R$_{1d}$ and R$_{1e}$ is heteroaryl;

R$_2$ is cycloalkyl, aryl, heteroaryl, heterocyclyl, —S(O)$_2$R$_5$, —C(=O)NR$_3$R$_5$, —C(=O)R$_5$ or —C(=O)OR$_5$, wherein the cycloalkyl, aryl, heteroaryl and heterocyclyl may each be optionally substituted with one or more R$_6$'s;

R$_3$ is hydrogen, alkyl, alkoxy, cycloalkyl, aryl, arylalkyl, heteroaryl, heteroarylalkyl, heterocyclyl or heterocyclylalkyl, wherein the heteroaryl;

R$_5$ is alkyl, alkenyl, aryl, cycloalkyl, heteroaryl or heterocyclyl, each of which may be optionally substituted with one or more R$_6$'s;

R$_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R$_{9a}$;

R$_8$, at each occurrence, is independently selected from the group consisting of alkyl, aryl, cycloalkyl, heteroaryl and heterocyclyl, each of which may be optionally substituted with one or more R$_{8a}$'s;

R$_{8a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, =O, —NR$_{14}$C(=O)OR$_{14}$ and NR$_{14}$S(O$_2$)R$_{14}$;

R$_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 R$_{9a}$;

R$_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$, =O and arylalkyl;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R_{10a}$;

$R_{10a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —O(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$ R$_{14}$, —NR$_{14}$C(=O)OR$_8$, —NR$_{14}$S(O$_2$)R$_8$ and aryl alkyl;

$R_{14}$, at each occurrence, is independently selected from hydrogen, alkyl, cycloalkyl and aryl;

$R_{20}$ and $R_{21}$ are each independently selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —CO(O)NR$_9$R$_9$, —C(=O)R$_{10}$ and —OC(=O)R$_{10}$.

In a sixth embodiment, a method of modulating the activity of the GPR119 G protein-coupled receptor wherein for the compound of Formula I or Formula IA:

ring A is optionally substituted with one or more R's shown as $R_{20}$ and $R_{21}$;

G is CH or N;

Q is C or N;

X is CH or N, provided that Q and X are not both N;

Y is CH$_2$, N(R$_3$), C(=O), O, OCR$_9$R$_9$, S, S(=O) or S(O)$_2$;

$n_1$ is 0-2;

$n_2$ is 0-2;

$n_3$ is 1-2;

$R_1$ is

[chemical structures showing three ring systems with substituents $R_{1a}$, $R_{1b}$, $R_{1c}$, $R_{1d}$, $R_{1e}$]

$R_{1a}$, $R_{1b}$, $R_{1c}$, $R_{1d}$ and $R_{1e}$ are each independently selected from the group consisting of hydrogen, alkyl, alkenyl, alkynyl, cycloalkyl, aryl, heteroaryl, heterocyclyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$N$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ and —NR$_9$S(O$_2$)R$_8$, wherein the alkyl alkenyl, alkynyl, cycloalkyl, aryl, heteroaryl and heterocyclyl may each be optionally substituted with one or more R$_6$'s; provided that at least one of $R_{1a}$, $R_{1b}$, $R_{1c}$, $R_{1d}$ and $R_{1e}$ is heteroaryl;

$R_2$ is cycloalkyl, aryl, heteroaryl, heterocyclyl, —S(O)$_2$R$_5$, —C(=O)NR$_3$R$_5$, —C(=O)R$_5$ or —C(=O)OR$_5$, wherein the cycloalkyl, aryl, heteroaryl and heterocyclyl may each be optionally substituted with one or more R$_6$'s;

$R_3$ is hydrogen, alkyl, alkoxy, cycloalkyl, aryl, arylalkyl, heteroaryl, heteroarylalkyl, heterocyclyl or heterocyclylalkyl;

$R_5$ is alkyl, alkenyl, aryl, cycloalkyl, heteroaryl or heterocyclyl, each of which may be optionally substituted with one or more R$_6$'s;

$R_6$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$ CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_8$, at each occurrence, is independently selected from the group consisting of alkyl, aryl, cycloalkyl, heteroaryl and heterocyclyl, each of which may be optionally substituted with one or more R$_{8a}$'s;

$R_{8a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$ R$_{14}$, =O, —NR$_{14}$C(=O)OR$_{14}$ and —NR$_{14}$S(O$_2$)R$_{14}$;

$R_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 $R_{9a}$;

$R_{9a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$ R$_{14}$, —NR$_{14}$C(=O)OR$_8$, —NR$_{14}$S(O$_2$)R$_8$, =O and arylalkyl;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R_{10a}$;

$R_{10a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ and aryl alkyl;

$R_{14}$, at each occurrence, is independently selected from hydrogen, alkyl, cycloalkyl and aryl; and $R_{20}$ and $R_{21}$ are each independently selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

In a seventh embodiment, a method of modulating the activity of the GPR119 G protein-coupled receptor wherein for the compound of Formula I or Formula IA:

ring A is optionally substituted with one or more R's shown as $R_{20}$ and $R_{21}$;
G is CH or N;
Q is C or N;
X is CH or N, provided that Q and X are not both N;
Y is CO$_2$, N(R$_3$), C(=O), O, OCR$_9$R$_9$, S, S(=O) or S(O)$_2$;
$n_1$ is 0-2;
$n_2$ is 0-2;
$n_3$ is 1-2;
$R_1$ is $R_{1a}$, $R_{1b}$, $R_{1d}$ and $R_{1e}$ are each independently selected from the group consisting of hydrogen, alkyl, alkenyl, alkynyl, cycloalkyl, halo, —CN, —OCF$_3$, —OR$_{10}$, —OH, —C(=O)NR$_9$R$_9$, —NR$_9$R$_9$, —S(O)$_2$NR$_9$R$_9$, —NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —S(=O)R$_{10}$, —S(O)$_2$R$_{10}$, —NR$_9$C(=O)OR$_8$ and —NR$_9$S(O$_2$)R$_8$, wherein the alkyl, alkenyl, alkynyl and cycloalkyl may each be optionally substituted with one or more $R_6$'s;

$R_{1c}$ is a 5-6 membered monocyclic heteroaryl which may be optionally substituted with one or more $R_6$'s;

$R_2$ is cycloalkyl, aryl, heteroaryl, heterocyclyl, —S(O)$_2$R$_5$, —C(=O)NR$_3$R$_5$, —C(=O)R$_5$ or —C(=O)OR$_5$, wherein the cycloalkyl, aryl, heteroaryl and heterocyclyl may each be optionally substituted with one or more $R_6$'s;

$R_3$ is hydrogen, alkyl, alkoxy, cycloalkyl, aryl, arylalkyl, heteroaryl, heteroarylalkyl, heterocyclyl or heterocyclylalkyl;

$R_5$ is alkyl, alkenyl, aryl, cycloalkyl, heteroaryl or heterocyclyl, each of which may be optionally substituted with one or more $R_6$'s;

$R_6$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_8$, at each occurrence, is independently selected from the group consisting of alkyl, aryl, cycloalkyl, heteroaryl and heterocyclyl, each of which may be optionally substituted with one or more $R_{8a}$'s;

$R_{8a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$—C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, =O, —NR$_{14}$C(=O)OR$_{14}$ and —NR$_{14}$S(O$_2$)R$_{14}$;

$R_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, alkoxy, aryl, arylalkyl, heteroaryl, heteroarylalkyl, heterocyclyl and heterocyclylalkyl may each be optionally substituted with 0-5 $R_{9a}$;

$R_{9a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$R$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$, =O and arylalkyl;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R_{10a}$;

$R_{10a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$ R$_{14}$, —NR$_{14}$C(=O)OR$_8$, —NR$_{14}$S(O$_2$)R$_8$ and aryl alkyl;

$R_{14}$, at each occurrence, is independently selected from hydrogen, alkyl, cycloalkyl and aryl; and $R_{20}$ and $R_{21}$ are each independently selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

In an eighth embodiment, a method of modulating the activity of the GPR119 G protein-coupled receptor wherein for the compound of Formula I or Formula IA.

ring A is optionally substituted with one or more R's shown as $R_{20}$ and $R_{21}$;

G is CH or N;

Q is C or N;

X is CH or N, provided that Q and X are not both N;

Y is CH$_2$, N(R$_3$), C(=O), O, OCR$_9$R$_9$, S, S(=O) or S(O)$_2$;

$n_1$ is 0-2;

$n_2$ is 0-2;

$n_3$ is 1-2;

$R_1$ is a 6-membered monocyclic aryl, a 5-membered monocyclic heteroaryl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1c}$, $R_{1d}$ and $R_{1e}$ are each independently selected from the group consisting of hydrogen, alkyl, alkenyl, alkynyl, cycloalkyl, aryl, heteroaryl, heterocyclyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ and —NR$_9$S(O$_2$)R$_8$, wherein the alkyl alkenyl, alkynyl, cycloalkyl, aryl, heteroaryl and heterocyclyl may each be optionally substituted with one or more R$_6$'s; provided that at least one of $R_{1a}$, $R_{1b}$, $R_{1c}$, $R_{1d}$ and $R_{1e}$ is heteroaryl;

$R_2$ is aryl, heteroaryl, heterocyclyl, —C(=O)NR$_3$R$_5$, —C(=O)R$_5$ or C(=O)OR$_5$, wherein the aryl, heteroaryl and heterocyclyl may each be optionally substituted with one or more R$_6$'s;

$R_3$ is hydrogen, alkyl, alkoxy, cycloalkyl, aryl, arylalkyl, heteroaryl, heteroarylalkyl, heterocyclyl or heterocyclylalkyl;

$R_5$ is alkyl, alkenyl, aryl, cycloalkyl, heteroaryl or heterocyclyl, each of which may be optionally substituted with one or more R$_6$'s;

$R_6$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$ CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R$_{9a}$;

$R_8$, at each occurrence, is independently selected from the group consisting of alkyl, aryl, cycloalkyl, heteroaryl and heterocyclyl, each of which may be optionally substituted with one or more R$_{8a}$'s;

$R_{8a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$—C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$ R$_{14}$, =O, —NR$_{14}$C(=O)OR$_{14}$ and NR$_{14}$S(O$_2$)R$_{14}$;

$R_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 R$_{9a}$;

$R_{9a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$ R$_{14}$, —NR$_{14}$C(=O)OR$_8$, —NR$_{14}$S(O$_2$)R$_8$, =O and arylalkyl;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 R$_{10a}$;

$R_{10a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$ R$_{14}$, —NR$_{14}$C(=O)OR$_8$, —NR$_{14}$S(O$_2$)R$_8$ and arylalkyl;

$R_{14}$, at each occurrence, is independently selected from hydrogen, alkyl, cycloalkyl and aryl; and $R_{20}$ and $R_{21}$ are each independently selected from the group consisting of hydrogen, alkyl, haloalkyl, cycloalkyl, halo, —CN, —C(=O)OH, —C(=O)OR$_{10}$, OCF$_3$, —OR$_{10}$, —OH, —C(=O)NR$_9$R$_9$, —C(=O)R$_{10}$ and —OC(=O)R$_{10}$.

In a ninth embodiment a method of modulating the activity of the GPR119 G protein-coupled receptor wherein for the compound of Formula I or Formula IA.

ring A is optionally substituted with one or more R's shown as $R_{20}$ and $R_{21}$;

G is CH or N;

Q is C or N;

X is CH or N, provided that Q and X are not both N;

Y is CH$_{12}$, N(R$_3$), C(=O), O, OCR$_9$R$_9$, S, S(=O) or S(O)$_2$;

$n_1$ is 0-2;

$n_2$ is 0-2;

$n_3$ is 1-2;

$R_1$ is a 6-membered monocyclic aryl, a 5-membered monocyclic heteroaryl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1c}$, $R_{1d}$ and $R_{1e}$ are each independently selected from the group consisting of hydrogen, alkyl, alkenyl, alkynyl, cycloalkyl, aryl, heteroaryl, heterocyclyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ and —NR$_9$S(O$_2$)R$_8$, wherein the alkyl alkenyl, alkynyl, cycloalkyl, aryl, heteroaryl and heterocyclyl may each be optionally substituted with one or more R's; provided that at least one of $R_{1a}$, $R_{1b}$, $R_{1c}$, $R_{1d}$ and $R_{1e}$ is heteroaryl; $R_2$ is aryl, heteroaryl, or —C(=O)OR$_5$, wherein the aryl and heteroaryl may each be optionally substituted with one or more R$_6$'s;

$R_3$ is hydrogen, alkyl, alkoxy, cycloalkyl, aryl, arylalkyl, heteroaryl, heteroarylalkyl, heterocyclyl or heterocyclylalkyl;

$R_5$ is alkyl, alkenyl, aryl, cycloalkyl, heteroaryl or heterocyclyl, each of which may be optionally substituted with one or more R$_6$'s;

$R_6$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_7$, —C(=O)ON, —C(=O)OR$_{10}$, —OCF$_3$, —OR$_{10}$, —CN, —SH, —SR$_{10}$, —S(O)$_3$N, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$ CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, O, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R$_{9a}$;

$R_8$, at each occurrence, is independently selected from the group consisting of alkyl, aryl, cycloalkyl, heteroaryl and heterocyclyl, each of which may be optionally substituted with one or more R$_{9a}$'s;

$R_{8a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O) OR$_{14}$, —OCF$_3$, —OR$_{14}$, —CN, —SH, —SR$_{14}$, —S(O)$_3$N, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$ R$_{14}$, =O, —NR$_{14}$C(=O)OR$_{14}$ and —NR$_{14}$S(O$_2$) R$_{14}$;

$R_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 R$_{9a}$;

$R_{9a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O) OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$ NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$) NR$_{14}$R$_{14}$, —NHC(=NR$_{14}$)NR$_{14}$R$_{14}$, —S(=O)R$_{14}$, —S(O)$_2$ R$_{14}$, —NR$_{14}$C(=O)OR$_8$, —NR$_{14}$S(O$_2$)R$_8$, =O and arylalkyl;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 R$_{10a}$;

$R_{10a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O) OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$ NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=O)NR$_{14}$) NR$_{14}$R$_{14}$, —NHC(NR$_{14}$)NR$_{14}$R$_{14}$, —S(=O)R$_{14}$, —S(O)$_2$ R$_{14}$, —NR$_{14}$C(=O)OR$_8$, —NR$_{14}$S(O$_2$)R$_8$ and arylalkyl;

$R_{14}$, at each occurrence, is independently selected from hydrogen, alkyl, cycloalkyl and aryl; and $R_{20}$ and $R_{21}$ are each independently selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)N$_9$R$_9$, —C(=O)R$_{10}$ and —OC(=O)R$_{10}$.

In a tenth embodiment, a method of modulating the activity of the GPR119 G protein-coupled receptor wherein for the compound of Formula I or Formula IA:

ring A is optionally substituted with one or more R's shown as $R_{20}$ and $R_{21}$;

G is CH or N;

Q is C or N;

X is CH or N, provided that Q and X are not both N;

Y is C$_1$H$_2$, N(R$_3$), C(=O), O, OCR$_9$R$_9$, S, S(=O) or S(O)$_2$;

$n_1$ is 0-2;

$n_2$ is 0-2;

$n_3$ is 1-2;

$R_1$ is a 6-membered monocyclic aryl, a 5-membered monocyclic heteroaryl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1c}$, $R_{1d}$ and $R_{1e}$ are each independently selected from the group consisting of hydrogen, alkyl, alkenyl, alkynyl, cycloalkyl, aryl, heteroaryl, heterocyclyl, halo, —NH$_2$—CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ and —NR$_9$S(O$_2$)R$_8$, wherein the alkyl alkynyl, cycloalkyl, aryl, heteroaryl and heterocyclyl may each be optionally substituted with one or more $R_6$'s; provided that at least one of $R_{1a}$, $R_{1b}$, $R_{1c}$, $R_{1d}$ and $R_{1e}$ is heteroaryl;

$R_2$ is heteroaryl or —C(=O)OR$_5$, wherein the heteroaryl may be optionally substituted with one or more $R_6$'s;

$R_3$ is hydrogen, alkyl, alkoxy, cycloalkyl, aryl, arylalkyl, heteroaryl, heteroarylalkyl, heterocyclyl or heterocyclylalkyl;

$R_5$ is alkyl, alkenyl, aryl, cycloalkyl, heteroaryl or heterocyclyl, each of which may be optionally substituted with one or more $R_6$'s;

$R_6$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_7$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$ CF$_3$, —C(=O)R$_{10}$, —NR$_9$C(=O))H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_8$, at each occurrence, is independently selected from the group consisting of alkyl, aryl, cycloalkyl, heteroaryl and heterocyclyl, each of which may be optionally JO substituted with one or more $R_{8a}$'s;

$R_{8a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$ R$_{14}$, =O, —NR$_{14}$C(=O)OR$_{14}$ and —NR$_{14}$S(O$_2$)R$_{14}$;

$R_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 $R_{9a}$;

$R_{9a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$ R$_{14}$, —NR$_{14}$C(=O)OR$_8$, —NR$_{14}$S(O$_2$)R$_8$, =O and arylalkyl;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R_{10a}$;

$R_{10a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ and arylalkyl;

$R_{14}$, at each occurrence, is independently selected from hydrogen, alkyl, cycloalkyl and aryl; and $R_{20}$ and $R_{21}$ are each independently selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

In an eleventh embodiment, a method of modulating the activity of the GPR119 G protein-coupled receptor wherein for the compound of Formula I or Formula IA:

ring A is optionally substituted with one or more R's shown as $R_{20}$ and $R_{21}$;

G is CH or N;

Q is C or N;

X is CH or N, provided that Q and X are not both N;

Y is CH$_2$, N(R$_3$), C(=O), O, OCR$_9$R$_9$, S, S(=O) or S(O)$_2$;

$n_1$ is 0-2;

$n_2$ is 0-2;

$n_3$ is 1-2;

$R_1$ is a 6-membered monocyclic aryl, a 5-membered monocyclic heteroaryl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1c}$, $R_{1d}$ and $R_{1e}$ are each independently selected from the group consisting of hydrogen, alkyl, alkenyl, alkynyl, cycloalkyl, aryl, heteroaryl, heterocyclyl, halo, —NH$_2$, —CN, —NO$_2$, —C(=O)OH, —C(=O)OR$_{10}$, —OCF$_3$—OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ and —NR$_9$S(O$_2$)R$_8$, wherein the alkyl alkenyl, alkynyl, cycloalkyl, aryl, heteroaryl and heterocyclyl may each be optionally substituted with one or more $R_6$'s; provided that at least one of $R_{1a}$, $R_{1b}$, $R_{1c}$, $R_{1d}$ and $R_{1e}$ is heteroaryl;

$R_2$ is heteroaryl which may be optionally substituted with one or more $R_6$'s;

$R_3$ is hydrogen, alkyl, alkoxy, cycloalkyl, aryl, arylalkyl, heteroaryl, heteroarylalkyl, heterocyclyl or heterocyclylalkyl;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{10}$, $-OCF_3$, $-OR_{10}$, $-OH$, $-SH$, $-SR_{10}$, $-S(O)_3H$, $-P(O)_3H_2$, $-C(=O)NR_9R_9$, $-NR_9R_9$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{10}$, $-NR_9C(=O)H$, $-NR_9C(=O)R_{10}$, $-OC(=O)R_{10}$, $-C(=NR_{14})NR_9R_9$, $-NHC(=NR_{14})NR_{14}R_{14}$, $-S(=O)R_{10}$, $-S(O)_2R_{10}$, $=O$, $-NR_9C(=O)OR_8$ and $-NR_9S(O_2)R_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_8$, at each occurrence, is independently selected from the group consisting of alkyl, aryl, cycloalkyl, heteroaryl and heterocyclyl, each of which may be optionally substituted with one or more $R_{8a}$'s;

$R_{8a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl halo, $-NH_2$, $-CN$, $-NO_2$, $-C(=O)OH$, $-C(=O)OR_{14}$, $-OCF_3$, $-OR_{14}$, $-OH$, $-SH$, $-SR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2CF_3$, $-C(=O)NR_{14}S(O)_2R_{14}$, $-S(O)_2NR_{14}C(=O)OR_{14}$, $-S(O)_2NR_{14}C(=O)NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=O)R_{14}$, $-C(=NR_{14})NR_{14}R_{14}$, $-NHC(=NR_{14})NR_{14}R_{14}$, $-S(=O)R_{14}$, $-S(O)_2R_{14}$, $=O$, $-NR_{14}C(=O)OR_{14}$ and $-NR_{14}S(O_2)R_{14}$;

$R_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 $R_{9a}$;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OR$, $-C(=O)OR_{14}$, $-OCF_3$, $-OR_{14}$, $-OH$, $-SH$, $-SR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2CF_3$, $-C(=O)NR_{14}S(O)_2R_{10}$, $-S(O)_2NR_{14}C(=O)OR_{10}$, $-S(O)_2NR_{14}C(=O)NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=O)R_{14}$, $-C(=NR_{14})NR_{14}R_{14}$, $-NHC(=NR_{34})NR_{14}R_{14}$, $-S(=O)R_{14}$, $-S(O)_2R_{14}$, $-NR_{14}C(=O)OR_8$, $-NR_{14}S(O_2)R_8$, $=O$ and arylalkyl;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R_{10a}$;

$R_{10a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, $-NH_2$, $-CN$, $-NO_2$, $-C(=O)OH$, $-C(=O)OR_{14}$, $-OCF_3$, $-OR_{14}$, $-OH$, $-SH$, $-SR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2CF_3$, $-C(=O)NR_{14}S(O)_2R_9$, $-S(O)_2NR_{14}C(=O)OR_9$, $-S(O)_2NR_{14}C(=O)NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=O)R_{14}$, $-C(=NR_{14})NR_{14}R_{14}$, $-NHC(=NR_{14})NR_{14}R_{14}$, $-S(=O)R_{14}$, $-S(O)_2R_{14}$, $-NR_{14}C(=O)O-$, $-NR_{14}S(O_2)R_8$ and aryl alkyl;

$R_{14}$, at each occurrence, is independently selected from hydrogen, alkyl, cycloalkyl and aryl; and $R_{20}$ and $R_{21}$ are each independently selected from the group consisting of hydrogen, alkyl, haloalkyl, cycloalkyl, halo, $-CN$, $-C(=O)OH$, $-C(=O)OR_{10}$, $-OCF_3$, $-OR_{10}$, $-OH$, $-C(=O)NR_9R_9$, $-C(=O)R_{10}$ and $-OC(=O)R_{10}$.

In a twelfth embodiment, a method of modulating the activity of the GPR119 G protein-coupled receptor wherein for the compound of Formula I or Formula IA:

ring A is optionally substituted with one or more R's shown as $R_{20}$ and $R_{21}$;

G is CH or N;

Q is C or N;

X is CH or N, provided that Q and X are not both N;

Y is $CH_2$, $N(R_3)$, $C(=O)$, O, $OCR_9R_9$, S, $S(=O)$ or $S(O)_2$;

$n_1$ is 0-2;

$n_2$ is 0-2;

$n_3$ is 1-2;

$R_1$ is a 6-membered monocyclic aryl, a 5-membered monocyclic heteroaryl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1c}$, $R_{1d}$ and $R_{1e}$ are each independently selected from the group consisting of hydrogen, alkyl, alkenyl, alkynyl, cycloalkyl, aryl, heteroaryl, heterocyclyl, halo, $-NH_2$, $-CN$, $-NO_2$, $-C(=O)OH$, $-C(=O)OR_{10}$, $-OCF_3$, $-OR_{10}$, $-OH$, $-SH$, $-SR_{10}$, $-S(O)_3H$, $-P(O)_3H_2$, $-C(=O)NR_9R_9$, $-NR_9R_9$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{10}$, $-NR_9C(=O)-$, $-NR_9C(=O)R_{10}$, $-OC(=O)R_{10}$, $-OC(=O)NR_9R_9$, $-C(=NR_{14})NR_9R_9$, $-NHC(=NR_{14})NR_{14}R_{14}$, $-S(=O)R_{10}$, $-S(O)_2R_{10}$, $-NR_9C(=O)OR_9$ and $-NR_9S(O_2)R_8$, wherein the alkyl alkenyl, alkynyl, cycloalkyl, aryl, heteroaryl and heterocyclyl may each be optionally substituted with one or more $R_6$'s; provided that at least one of $R_{1a}$, $R_{1b}$, $R_{1c}$, $R_{1d}$ and $R_{1e}$ is heteroaryl;

$R_2$ is oxadiazolyl, benzoxazolyl, pyridinyl or pyrimidinyl, each of which may be optionally substituted with one or more $R_6$'s;

$R_3$ is hydrogen, alkyl, alkoxy, cycloalkyl, aryl, arylalkyl, heteroaryl, heteroarylalkyl, heterocyclyl or heterocyclylalkyl;

$R_6$ at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, $-NH_2$, $-CN$, $-NO_2$, $-C(=O)OH$, $-C(=O)OR_{10}$, $-OCF_3$, $-OR_{10}$, $-OH$, $-SH$, $-SR_{10}$, $-S(O)_3H$, $-P(O)_3H_2$, $-C(=O)NR_9R_9$, $-NR_9R_9$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2-NR_9C(=O)NR_9R_9$, $-C(=O)NR_9S(O)_2CF_3$, $-C(=O)R_{10}$, $-NR_9C(=O)H$, $-NR_9C(=O)R_{10}$, $-OC(=O)R_{10}$, $-C(=NR_{14})NR_9R_9$, $-NHC(=NR_{14})NR_{14}R_{14}$, $-S(=O)R_{10}$, $-S(O)_2R_{10}$, $=O$, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R$_{9a}$;

R$_8$, at each occurrence, is independently selected from the group consisting of alkyl, aryl, cycloalkyl, heteroaryl and heterocyclyl, each of which may be optionally substituted with one or more R$_{8a}$'s;

R$_{8a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, =O, —NR$_{14}$C(=O)OR$_{14}$ and NR$_{14}$S(O$_2$)R$_{14}$;

R$_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 R$_{9a}$;

R$_{9a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$, =O and arylalkyl;

R$_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may be optionally substituted with 0-3 R$_{10a}$;

R$_{10a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ and aryl alkyl;

R$_{14}$, at each occurrence, is independently selected from hydrogen, alkyl, cycloalkyl and aryl; and R$_{20}$ and R$_{21}$ are each independently selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O—R$_{10}$.

In a thirteenth embodiment, a method of modulating the activity of the GPR119 G protein-coupled receptor wherein for the compound of Formula I or Formula IA.

ring A is optionally substituted with one or more R's shown as R$_{20}$ and R$_{21}$;

G is CH or N;

Q is C or N;

X is CH or N, provided that Q and X are not both N;

Y is CH$_2$, N(R$_3$), C(=O), O, OCR$_9$R$_9$, S, S(=O) or S(O)$_2$;

n$_1$ is 0-2;

n$_2$ is 0-2;

n$_3$ is 1-2;

R$_1$ is a 6-membered monocyclic aryl, a 5-membered monocyclic heteroaryl or a 6-membered monocyclic heteroaryl, each of which may be optionally substituted with one or more members selected from R$_{1a}$, R$_{1b}$, R$_{1c}$, R$_{1d}$ and R$_{1e}$;

R$_{1a}$, R$_{1b}$, R$_{1c}$, R$_{1d}$ and R$_{1e}$ are each independently selected from the group consisting of hydrogen, alkyl, alkenyl, alkynyl, cycloalkyl, aryl, heteroaryl, heterocyclyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ and —NR$_9$S(O$_2$)R$_8$, wherein the alkyl alkenyl, alkynyl, cycloalkyl, aryl, heteroaryl and heterocyclyl may each be optionally substituted with one or more R$_6$'s; provided that at least one of R$_{1a}$, R$_{1b}$, R$_{1c}$, R$_{1d}$ and R$_{1e}$ is heteroaryl;

R$_2$ is pyrimidinyl which may be optionally substituted with one or more R$_6$'s;

R$_3$ is hydrogen, alkyl, alkoxy, cycloalkyl, aryl, arylalkyl, heteroaryl, heteroarylalkyl, heterocyclyl or heterocyclylalkyl;

R$_6$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R$_{9a}$;

R$_8$, at each occurrence, is independently selected from the group consisting of alkyl, aryl, cycloalkyl, heteroaryl and heterocyclyl, each of which may be optionally substituted with one or more R$_{8a}$'s;

R$_{8a}$, at each occurrence, is independently selected from alkyl, haloalkyl, aryl, alkenyl, alkynyl cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)

$NR_{14}R_{14}$, $-NHC(NR_{14})NR_{14}R_{14}$, $-S(=O)R_{14}$, $-S(O)_2 R_{14}$, $=O$, $-NR_{14}C(=O)OR_{14}$ and $NR_{14}S(O_2)R_{14}$;

$R_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 $R_{9a}$;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{14}$, $-OCF_3$, $-OR_{14}$, $-OH$, $-SH$, $-SR_{14}$, $-S(O)_3H$, $-P(O)_3H_2$, $-C(=O)NR_{14}R_{14}$, $-NR_{14}R_{14}$, $-S(O)_2 NR_{14}R_{14}$, $-NR_{14}S(O)_2CF_3$, $-C(=O)NR_{14}S(O)_2R_{10}$, $-S(O)_2NR_{14}C(=O)OR_{10}$, $-S(O)_2NR_{14}C(=O)NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=O)R_{14}$, $-C(=NR_{14}) NR_{14}R_{14}$, $-NHC(=NR_{14})NR_{14}R_{14}$, $-S(=O)R_{14}$, $-S(O)_2 R_{14}$, $-NR_{14}C(=O)OR_8$, $-NR_{14}S(O_2)R_8$, $=O$ and arylalkyl;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R_{10a}$;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=(O)OH$, $-C(=O)OR_{14}$, $-OCF_3$, $-OR_{14}$, $-OH$, $-SH$, $-SR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2CF_3$, $-C(=O)NR_{14}S(O)_2 R_9$, $-S(O)_2NR_{14}C(=O)OR_9$, $-S(O)_2NR_{14}C(=O) NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=O)R_{14}$, $-C(=NR_{14})NR_{14}R_{14}$, $-NHC(=NR_{14})NR_{14}R_{14}$, $-S(=O)R_{14}$, $-S(O)_2R_{14}$, $-NR_{14}C(=O)OR_8$, $-NR_{14}S (O_2)R_8$ and arylalkyl;

$R_{14}$, at each occurrence, is independently selected from hydrogen, alkyl, cycloalkyl and aryl; and $R_{20}$ and $R_{21}$ are each independently selected from the group consisting of hydrogen, alkyl, haloalkyl, cycloalkyl, halo, $-CN$, $-C(=O)OH$, $-C(=O)OR_{10}$, $-OCF_3$, $-OR_{10}$, $-OH$, $-C(=O)NR_9R_9$, $-C(=O)R_{10}$ and $-OC(=O)R_{10}$.

In a fourteenth embodiment, a method of modulating the activity of the GPR119 G protein-coupled receptor wherein for the compound of Formula I or Formula IA:

ring A is optionally substituted with one or more R's shown as $R_{20}$ and $R_{21}$;

G is CH or N;

Q is C or N;

X is CH or N, provided that Q and X are not both N;

Y is $CH_2$, $N(R_3)$, $C(=O)$, O, $OCR_9R_9$, S, $S(=O)$ or $S(O)_2$;

$n_1$ is 0-2;

$n_2$ is 0-2;

$n_3$ is 1-2;

$R_1$ is a 6-membered monocyclic aryl, a 5-membered monocyclic heteroaryl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1c}$, $R_{1d}$ and $R_{1e}$ are each independently selected from the group consisting of hydrogen, alkyl, alkenyl, alkynyl, cycloalkyl, aryl, heteroaryl, heterocyclyl, halo, $-NH_2$, $-CN$, $-NO_2$, $-C(=O)OH$, $-C(=O)OR_{10}$, $-OCF_3$, $-OR_{10}$, $-OH$, $-SH$, $-SR_{10}$, $-S(O)_3H$, $-P(O)_3H_2$, $-C(=O)NR_9R_9$, $-NR_9R_9$, $-S(O)_2NR_9R_9$, $-NR_9S(O)_2 CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{10}$, $-NR_9C(=O)H$, $-NR_9C(=O)R_{10}$, $-OC (=O)R_{10}$, $-OC(=O)NR_9R_9$, $-C(=NR_{14})NR_9R_9$, $-NHC(=NR_{14})NR_{14}R_{14}$, $-S(=O)R_{10}$, $-S(O)_2R_{10}$, $-NR_9C(=O)OR_8$ and $-NR_9S(O_2)R_8$, wherein the alkyl, alkenyl, alkynyl, cycloalkyl, aryl, heteroaryl and heterocyclyl may each be optionally substituted with one or more $R_6$'s; provided that at least one of $R_{1a}$, $R_{1b}$, $R_{1c}$, $R_{1d}$ and $R_{1e}$ is heteroaryl;

$R_2$ is $-C(=O)OR_5$;

$R_3$ is hydrogen, alkyl, alkoxy, cycloalkyl, aryl, arylalkyl, heteroaryl, heteroarylalkyl, heterocyclyl or heterocyclylalkyl;

$R_5$ is alkyl, alkenyl, aryl, cycloalkyl, heteroaryl or heterocyclyl, each of which may be optionally substituted with one or more $R_6$'s;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{10}$, $-OCF_3$, $-OR_{10}$, $-OH$, $-SH$, $-SR_{10}$, $-S(O)_3H$, $-P(O)_3H_2$, $-C(=O)NR_9R_9$, $-NR_9R_9$, $-S(O)_2NR_9R_9$, $-NR_9S(O)_2 CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{10}$, $-NR_9C(=O)H$, $-NR_9C(=O)R_{10}$, $-OC (=O)R_{10}$, $-OC(=O)NR_9R_9$, $-C(=NR_{14})NR_9R_9$, $-NHC(=NR_{14})NR_{14}R_{14}$, $-S(=O)R_{10}$, $-S(O)_2R_{10}$, $-NR_9C(=O)OR_8$ and $-NR_9S(O_2)R_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_8$, at each occurrence, is independently selected from the group consisting of alkyl, aryl, cycloalkyl, heteroaryl and heterocyclyl, each of which may be optionally substituted with one or more $R_{8a}$'s;

$R_{8a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{14}$, $-OCF_3$, $-OR_{14}$, $-OH$, $-SH$, $-SR_{14}$, $-S(O)_3H$, $-P(O)_3H_2$, $-C(=O)NR_{14}R_{14}$, $-NR_{14}R_{14}$, $-S(O)_2 NR_{14}R_{14}$, $-NR_{14}S(O)_2CF_3$, $-C(=O)NR_{14}S(O)_2R_{14}$, $-S(O)_2NR_{14}C(=O)OR_{14}$, $-S(O)_2NR_{14}C(=O)NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=O)R_{14}$, $-C(=NR_{14}) NR_{14}R_{14}$, $-NHC(=NR_{14})NR_{14}R_{14}$, $-S(=O)R_{14}$, $-S(O)_2 R_{14}$, $=O$, $-NR_{14}C(=O)OR_{14}$ and $-NR_{14}S(O_2) R_{14}$;

$R_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl aryl, arylalkyl, heteroaryl, heteroarylalkyl, heterocyclyl and heterocyclylalkyl may each be optionally substituted with 0-5 $R_{9a}$;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, $-NH_2$, $-CN$, $-NO_2$, $-C(=O)OH$, $-C(=O)OR_{14}$, $-OCF_3$, $-OR_{14}$, $-OH$, $-SH$, $-SR_{14}$, $-S(O)_3H$, $-P(O)_3H_2$, $-C(=O)NR_{14}R_{14}$, $-NR_{14}R_{14}$, $-S(O)_2 NR_{14}R_{14}$, $-NR_{14}S(O)CF_3$, $-C(=O)NR_{14}S(O)_2R_{10}$, $-S(O)_2NR_{14}C(=O)OR_{10}$, $-S(O)_2NR_{14}C(=O)NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=O)R_{14}$, $-C(=NR_{14})$ $NR_{14}R_{14}$, —$NHC(=NR_{14})NR_{14}R_{14}$, —$S(=O)R_{14}$, —$S(O)_2R_{14}$, —$NR_{14}C(=O)OR_9$, —$NR_{14}S(O_2)R_8$, =O and arylalkyl;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R_{10a}$;

$R_{10a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —$NH_2$, —CN, —$NO_2$, —$C(=O)OH$, —$C(=O)OR_{14}$, —$OCF_3$, —$OR_{14}$, —OH, —SH, —$SR_{14}$, —$S(O)_3H$, —$P(O)_3H_2$, —$C(=O)NR_{14}R_{14}$, —$NR_{14}R_{14}$, —$S(O)_2NR_{14}R_{14}$, —$NR_{14}S(O)_2CF_3$, —$C(=O)NR_{14}S(O)_2R_9$, —$S(O)_2NR_{14}C(=O)OR_9$, —$S(O)_2NR_{14}C(=O)NR_{14}R_{14}$, —$C(=O)NR_{14}S(O)_2CF_3$, —$C(=O)R_{14}$, —$NR_{14}C(=O)H$, —$NR_{14}C(=O)R_{14}$, —$OC(=O)R_{14}$, —$C(=NR_{14})NR_{14}R_{14}$, —$NHC(=NR_{14})NR_{14}R_{14}$, —$S(=O)R_{14}$, —$S(O)_2R_{14}$, —$NR_{14}C(=O)OR_8$, —$NR_{14}S(O_2)R_8$ and aryl alkyl;

$R_{14}$, at each occurrence, is independently selected from hydrogen, alkyl, cycloalkyl and aryl; and $R_{20}$ and $R_{21}$ are each independently selected from the group consisting of hydrogen, alkyl, haloalkyl, cycloalkyl, halo, —CN, —$C(=O)OH$, —$C(=O)OR_{10}$, —$OCF_3$, —$OR_{10}$, —OH, —$C(=O)NR_9R_9$, —$C(=O)R_{10}$ and —$OC(=O)R_{10}$.

In a fifteenth embodiment, a method of modulating the activity of the GPR119 G protein-coupled receptor wherein for the compound of Formula I or Formula IA:

ring A is optionally substituted with one or more R's shown as $R_{20}$ and $R_{21}$;

G is CH or N;

Q is C or N;

X is CH or N, provided that Q and X are not both N;

Y is $CH_2$, $N(R_3)$, $C(=O)$, O, $OCR_9R_9$, S, $S(=O)$ or $S(O)_2$;

$n_1$ is 0-2;

$n_2$ is 0-2;

$n_3$ is 1-2;

$R_1$ is a 6-membered monocyclic aryl, a 5-membered monocyclic heteroaryl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1c}$, $R_{1d}$ and $R_{1e}$ are each independently selected from the group consisting of hydrogen, alkyl, alkenyl, alkynyl, cycloalkyl, aryl, heteroaryl, heterocyclyl, halo, —$NH_2$, —CN, —$NO_2$, —$C(=O)OH$, —$C(=O)OR_{10}$, —$OCF_3$, —$OR_{10}$, —OH, —SH, —$SR_{10}$, —$S(O)_3H$, —$P(O)_3H_2$, —$C(=O)NR_9R_9$, —$NR_9R_9$, —$S(O)_2NR_9R_9$, —$NR_9S(O)_2CF_3$, —$C(=O)NR_9S(O)_2R_9$, —$S(O)_2NR_9C(=O)OR_9$, —$S(O)_2NR_9C(=O)NR_9R_9$, —$C(=O)NR_9S(O)_2CF_3$, —$C(=O)R_{10}$, —$NR_9C(=O)H$, —$NR_9C(=O)R_{10}$, —$OC(=O)R_{10}$, —$OC(=O)NR_9R_9$, —$C(=NR_{14})NR_9R_9$, —$NHC(=NR_{14})NR_{14}R_{14}$, —$S(=O)R_{10}$, —$S(O)_2R_{10}$, —$NR_9C(=O)OR_8$ and —$NR_9S(O_2)R_8$, wherein the alkyl alkenyl, alkynyl, cycloalkyl, aryl, heteroaryl and heterocyclyl may each be optionally substituted with one or more $R_6$'s; provided that at least one of $R_{1a}$, $R_{1b}$, $R_{1c}$, $R_{1d}$ and $R_{1e}$ is heteroaryl;

$R_2$ is —$C(=O)OR_5$;

$R_3$ is hydrogen, alkyl, alkoxy, cycloalkyl, aryl, arylalkyl, heteroaryl, heteroarylalkyl, heterocyclyl or heterocyclylalkyl;

$R_5$ is alkyl, alkenyl, aryl, cycloalkyl, heteroaryl or heterocyclyl, each of which may be optionally substituted with one or more $R_6$'s;

$R_6$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —CN, —$C(=O)OR_{10}$, —$OCF_3$, —$OR_{10}$, —OH, —SH, —$SR_{10}$, —$C(=O)NR_9R_9$, —$NR_9R_9$, —$S(O)_2NR_9R_9$, —$NR_9S(O)_2CF_3$, —$C(=O)R_{10}$, —$NR_9C(=O)H$, —$NR_9C(=O)R_{10}$, —$OC(=O)R_{10}$, —$S(=O)R_{10}$, —$S(O)_2R_{10}$, =O, —$NR_9C(=O)OR_8$ and —$NR_9S(O_2)R_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_8$, at each occurrence, is independently selected from the group consisting of alkyl, aryl, cycloalkyl, heteroaryl and heterocyclyl, each of which may be optionally substituted with one or more $R_{8a}$'s;

$R_{8a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —$NH_2$, —CN, —$NO_2$, —$C(=O)OH$, —$C(=O)OR_{14}$, —$OCF_3$, —$OR_{14}$, —OH, —SH, —$SR_{14}$, —$S(O)_3H$, —$P(O)_3H_2$, —$C(=O)NR_{14}R_{14}$, —$NR_{14}R_{14}$, —$S(O)_2NR_{14}R_{14}$, —$NR_{14}S(O)_2CF_3$, —$C(=O)NR_{14}S(O)_2R_9$, —$S(O)_2NR_{14}C(=O)OR_{14}$, —$S(O)_2NR_{14}C(=O)NR_{14}R_{14}$, —$C(=O)NR_{14}S(O)_2CF_3$, —$C(=O)R_{14}$, —$NR_{14}C(=O)H$, —$NR_{14}C(=O)R_{14}$, —$OC(=O)R_{14}$, —$C(=NR_{14})NR_{14}R_{14}$, —$NHC(=NR_{14})NR_{14}R_{14}$, —$S(=O)R_{14}$, —$S(O)_2R_{14}$, =O, —$NR_{14}C(=O)OR_{14}$ and —$NR_{14}S(O_2)R_{14}$;

$R_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 $R_{9a}$;

$R_{9a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —$NH_2$, —CN, —$NO_2$, —$C(=O)OH$, —$C(=O)OR_{14}$, —$OCF_3$, —$OR_{14}$, —OH, —SH, —$SR_{14}$, —$S(O)_3H$, —$P(O)_3H_2$, —$C(=O)NR_{14}R_{14}$, —$NR_{14}R_{14}$, —$S(O)_2NR_{14}R_{14}$, —$NR_{14}S(O)_2CF_3$, —$C(=O)NR_{14}S(O)_2R_{10}$, —$S(O)_2NR_{14}C(=O)OR_{10}$, —$S(O)_2NR_{14}C(=O)NR_{14}R_{14}$, —$C(=O)NR_{14}S(O)_2CF_3$ —$C(=O)R_{14}$, —$NR_{14}C(=O)H$, —$NR_{14}C(=O)R_{14}$, —$OC(=O)R_{14}$, —$C(=NR_{14})NR_{14}R_{14}$, —$NHC(=NR_{14})NR_{14}R_{14}$, —$S(=O)R_{14}$, —$S(O)_2R_{14}$, —$NR_{14}C(=O)OR_8$, —$NR_{14}S(O_2)R_8$, =O and arylalkyl;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R_{10a}$;

$R_{10a}$, at each occurrence, is independently selected from alkyl, haloalkyl, aryl, alkenyl, alkynyl cycloalkyl, cycloalkyl alkyl, heteroaryl, heteroarylalkyl, heterocyclyl, heterocyclyl alkyl, halo, —$NH_2$, —CN, —$NO_2$, —$C(=O)OH$, —$C(=O)OR_{14}$, —$OCF_3$, —$OR_{14}$, —OH, —SH, —$SR_{14}$, —$S(O)_3H$, —$P(O)_3H_2$, —$C(=O)NR_{14}R_{14}$, —$NR_{14}R_{14}$, —$S(O)_2NR_{14}R_{14}$, —$NR_{14}S(O)_2CF_3$, —$C(=O)NR_{14}S(O)_2R_9$, —$S(O)_2NR_{14}C(=O)OR_9$, —$S(O)_2NR_{14}C(=O)NR_{14}R_{14}$, —$C(=O)NR_{14}S(O)_2CF_3$, —$C(=O)R_{14}$, —$NR_{14}C(=O)H$, —$NR_{14}C(=O)R_{14}$, —$OC(=O)R_{14}$, —$C(=NR_{14})$ $NR_{14}R_{14}$, —$NHC(=NR_{14})NR_{14}R_{14}$, —$S(=O)R_{14}$, —$S(O)_2 R_{14}$, —$NR_{14}C(=O)OR_8$, —$NR_{14}S(O_2)R_8$ and arylalkyl;

$R_{14}$, at each occurrence, is independently selected from hydrogen, alkyl, cycloalkyl and aryl; and $R_{20}$ and $R_{21}$ are each independently selected from the group consisting of hydrogen, alkyl, haloalkyl, cycloalkyl, halo, —CN, —C(=O)OH, —C(=O)$OR_{10}$, —$OCF_3$, —$OR_{10}$, —OH, —C(=O)$NR_9R_9$, —C(=O)$R_{10}$ and —OC(=O)$R_{10}$.

In a sixteenth embodiment, a method of modulating the activity of the GPR119 G protein-coupled receptor wherein for the compound of Formula I or Formula IA:

ring A is optionally substituted with one or more R's shown as $R_{20}$ and $R_{21}$;

G is CH or N;

Q is C or N;

X is CH or N, provided that Q and X are not both N;

Y is $CH_2$, $N(R_3)$, C(=O), O, $OCR_9R_9$, S, S(=O) or $S(O)_2$;

$n_1$ is 0-2;

$n_2$ is 0-2;

$n_3$ is 1-2;

$R_1$ is a 6-membered monocyclic aryl, a 5-membered monocyclic heteroaryl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1c}$, $R_{1d}$ and $R_{1e}$ are each independently selected from the group consisting of hydrogen, alkyl, alkenyl, alkynyl, cycloalkyl, aryl, heteroaryl, heterocyclyl, halo, —$NH_2$—CN, —$NO_2$, —C(=O)OH, —C(=O)$OR_{10}$, —$OCF_3$, —$OR_{10}$, —OH, * —SH, —$SR_{10}$, —$S(O)_3H$, —$P(O)_3H_2$, —C(=O)$NR_9R_9$, —$NR_9R_9$, —$S(O)_2NR_9R_9$, —$NR_9S(O)_2CF_3$, —C(=O)$NR_9S(O)_2R_9$, —$S(O)_2NR_9C(=O)OR_9$, —$S(O)_2NR_9C(=O)NR_9R_9$, —C(=O)$NR_9S(O)_2CF_3$, —C(=O)$R_{10}$, —$NR_9C(=O)H$, —$NR_9C(=O)R_{10}$, —OC(=O)$R_{10}$, —OC(=O)$NR_9R_9$, —C(=$NR_{14}$)$NR_9R_9$, —NHC(=$NR_{14}$)$NR_{14}R_{14}$, —S(=O)$R_{10}$, —$S(O)_2R_{10}$, —$NR_9C(=O)OR_8$ and —$NR_9S(O_2)R_8$, wherein the alkyl, alkenyl, alkynyl, cycloalkyl, aryl, heteroaryl and heterocyclyl may each be optionally substituted with one or more $R_6$'s; provided that at least one of $R_{1a}$, $R_{1b}$, $R_{1c}$, $R_{1d}$ and $R_{1e}$ is heteroaryl;

$R_2$ is cycloalkyl, aryl, heteroaryl, heterocyclyl, —$S(O)_2R_5$, —C(=O)$NR_3R_5$, —C(=O)$R_5$ or —C(=O)$OR_5$, wherein the cycloalkyl, aryl, heteroaryl and heterocyclyl may each be optionally substituted with one or more $R_6$'s;

$R_3$ is hydrogen, alkyl, alkoxy, cycloalkyl, aryl, arylalkyl, heteroaryl, heteroarylalkyl, heterocyclyl or heterocyclylalkyl;

$R_5$ is alkyl, alkenyl, aryl, cycloalkyl, heteroaryl or heterocyclyl, each of which may be optionally substituted with one or more $R_6$'s;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$—CN, —$NO_2$, —C(=O)OH, —C(=O)$OR_{10}$, —$OCF_3$, —$OR_{10}$, —OH, —SH, —$SR_{10}$, —$S(O)_3H$, —$P(O)_3H_2$, —C(=O)$NR_9R_9$, —$NR_9R_9$, —$S(O)_2NR_9R_9$, —$NR_9S(O)_2CF_3$, —C(=O)$NR_9S(O)_2R_9$, —$S(O)_2NR_9C(=O)OR_9$, —$S(O)_2NR_9C(=O)NR_9R_9$, —C(=O)$NR_9S(O)_2 CF_3$, —C(=O)$R_{10}$, —$NR_9C(=O)H$, —$NR_9C(=O)R_{10}$, —OC(=O)$R_{10}$, —C(=$NR_{14}$)$NR_9R_9$, —NHC(=$NR_{14}$)$NR_{14}R_{14}$, —S(=O)$R_{10}$, —$S(O)_2R_{10}$, =O, —$NR_9C(=O)OR_8$ and —$NR_9S(O_2)R_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_8$, at each occurrence, is independently selected from the group consisting of alkyl, aryl, cycloalkyl, heteroaryl and heterocyclyl, each of which may be optionally substituted with one or more $R_{8a}$'s;

$R_{8a}$, at each occurrence, is independently selected from alkyl, haloalkyl aryl, alkenyl, alkynyl, cycloalkyl, cycloalkyl alkyl, heteroaryl, heteroarylalkyl, heterocyclyl, heterocyclyl alkyl, halo, —$NH_2$, —CN, —$NO_2$, —C(=O)OH, —C(=O)$OR_{14}$, —$OCF_3$, —$OR_{14}$, —OH, —SH, —$SR_{14}$, —$S(O)_3H$, —$P(O)_3H_2$, —C(=O)$NR_{14}R_{14}$, —$NR_{14}R_{14}$, —$S(O)_2NR_{14}R_{14}$, —$NR_{14}S(O)_2CF_3$, —C(=O)$NR_{14}S(O)_2R_{14}$, —$S(O)_2NR_{14}C(=O)OR_{14}$, —$S(O)_2NR_{14}C(=O)NR_{14}R_{14}$, —C(=O)$NR_{14}S(O)_2CF_3$, —C(=O)$R_{14}$, —$NR_{14}C(=O)H$, —$NR_{14}C(=O)R_{14}$, —OC(=O)$R_{14}$, —C(=$NR_{14}$)$NR_{14}R_{14}$, —NHC(=$NR_{14}$)$NR_{14}R_{14}$, —S(=O)$R_{14}$, —$S(O)_2 R_{14}$, =O, —$NR_{14}C(=O)OR_{14}$ and —$NR_{14}S(O_2)R_{14}$;

$R_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 $R_{9a}$;

$R_{9a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —$NH_2$, —CN, —$NO_2$, —C(=O)OH, —C(=O)$OR_{14}$, —$OCF_3$, —$OR_{14}$, —OH, —SH, —$SR_{14}$, —$S(O)_3H$, —$P(O)_3H_2$, —C(=O)$NR_{14}R_{14}$, —$NR_{14}R_{14}$, —$S(O)_2NR_{14}R_{14}$, —$NR_{14}S(O)_2CF_3$, —C(=O)$NR_{14}S(O)_2R_{10}$, —$S(O)_2NR_{14}C(=O)OR_{10}$, —$S(O)_2NR_{14}C(=O)NR_{14}R_{14}$, —C(=O)$NR_{14}S(O)_2CF_3$—C(=O)$R_{14}$, —$NR_{14}C(=O)H$, —$NR_{14}C(=O)R_{14}$, —OC(=O)$R_{14}$, —C(=$NR_{14}$)$NR_{14}R_{14}$, —NHC(=$NR_{14}$)$NR_{14}R_{14}$, —S(=O)$R_{14}$, —$S(O)_2 R_{14}$, —$NR_{14}C(=O)OR_8$, —$NR_{14}S(O_2)R_8$, =O and arylalkyl, $R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R_{10a}$;

$R_{10a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —$NH_2$, —CN, —$NO_2$, —C(=O)OH, —C(=O)$OR_{14}$, —$OCF_3$, —$OR_{14}$, —OH, —SH, —$SR_{14}$, —$S(O)_3H$, —$P(O)_3H_2$, —C(=O)$NR_{14}R_{14}$, —$NR_{14}R_{14}$, —$S(O)_2NR_{14}R_{14}$, —$NR_{14}S(O)_2CF_3$, —C(=O)$NR_{14}S(O)_2R_9$, —$S(O)_2NR_{14}C(=O)OR_9$, —$S(O)_2NR_{14}C(=O)NR_{14}R_{14}$, —C(=O)$NR_{14}S(O)_2CF_3$, —C(=O)$R_{14}$, —$NR_{14}C(=O)H$, —$NR_{14}C(=O)R_{14}$, —OC(=O)$R_{14}$, —C(=$NR_{14}$)$NR_{14}R_{14}$, —NHC(=$NR_{14}$)$NR_{14}R_{14}$, —S(=O)$R_{14}$, —$S(O)_2 R_{14}$, —$NR_{14}C(=O)OR_8$, —$NR_{14}S(O_2)R_8$ and arylalkyl;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, cycloalkyl, halo, —CN, —C(=O)OH, —C(=O)$OR_{10}$, —$OCF_3$, —$OR_{10}$, —OH, —C(=O)$NR_9R_9$, —C(=O)$R_{10}$ and —OC(=O)$R_{10}$.

In a seventeenth embodiment, a method of modulating the activity of the GPR119 G protein-coupled receptor wherein for the compound of Formula I or Formula IA:

ring A is optionally substituted with one or more R's shown as $R_{20}$ and $R_{21}$;

G is CH or N;
Q is C or N;
X is CH;
Y is $CH_2$, $N(R_3)$, $C(=O)$, O, $OCR_9R_9$, S, $S(=O)$ or $S(O)_2$;
$n_1$ is 0-2;
$n_2$ is 0-2;
$n_3$ is 1-2;
$R_1$ is a 6-membered monocyclic aryl, a 5-membered monocyclic heteroaryl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1c}$, $R_{1d}$ and $R_{1e}$ are each independently selected from the group consisting of hydrogen, alkyl, alkenyl, alkynyl, cycloalkyl, aryl, heteroaryl, heterocyclyl, halo, $-NH_2$, $-CN$, $-NO_2$, $-C(=O)OH$, $-C(=O)OR_{10}$, $-OCF_3$, $-OR_{10}$, $-OH$, $-SH$, $-SR_{10}$, $-S(O)_3H$, $-P(O)_3H_2$, $-C(=O)NR_9R_9$, $-NR_9R_9$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{10}$, $-NR_9C(=O)H$, $-NR_9C(=O)R_{10}$, $-OC(=O)R_{10}$, $-OC(=O)NR_9R_9$, $-C(=NR_{14})NR_9R_9$, $-NHC(=NR_{14})NR_{14}R_{14}$, $-S(=O)R_{10}$, $-S(O)_2R_{10}$, $-NR_9C(=O)OR_8$ and $-NR_9S(O_2)R_8$, wherein the alkyl, alkenyl, alkynyl, cycloalkyl, aryl, heteroaryl and heterocyclyl may each be optionally substituted with one or more $R_6$'s; provided that at least one of $R_{1a}$, $R_{1b}$, $R_{1c}$, $R_{1d}$ and $R_{1e}$ is heteroaryl;

$R_2$ is cycloalkyl, aryl, heteroaryl, heterocyclyl, $-S(O)_2R_5$, $-C(=O)NR_3R_5$, $-C(=O)R_5$ or $-C(=O)OR_5$, wherein the cycloalkyl, aryl, heteroaryl and heterocyclyl may each be optionally substituted with one or more $R_6$'s;

$R_3$ is hydrogen, alkyl, alkoxy, cycloalkyl, aryl, arylalkyl, heteroaryl, heteroarylalkyl, heterocyclyl or heterocyclylalkyl;

$R_5$ is alkyl, alkenyl, aryl, cycloalkyl, heteroaryl or heterocyclyl, each of which may be optionally substituted with one or more $R_6$'s;

$R_6$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, $-NH_2$, $-CN$, $-NO_2$, $-C(=O)OH$, $-C(=O)OR_{10}$, $-OCF_3$, $-OR_{10}$, $-OH$, $-SH$, $-SR_{10}$, $-S(O)_3H$, $-P(O)_3H_2$, $-C(=O)NR_9R_9$, $-NR_9R_9$, $-S(O)_2NR_9R_9$, $-NR_9S(O)_2CF_3$, $-C(=O)NR_9S(O)_2R_9$, $-S(O)_2NR_9C(=O)OR_9$, $-S(O)_2NR_9C(=O)NR_9R_9$, $-C(=O)NR_9S(O)_2CF_3$, $-C(=O)R_{10}$, $-NR_9C(=O)H$, $-NR_9C(=O)R_{10}$, $-OC(=O)R_{10}$, $-C(=NR_{14})NR_9R_9$, $-NHC(=NR_{14})NR_{14}R_{14}$, $-S(=O)R_{10}$, $-S(O)_2R_{10}$, $=O$, $-NR_9C(=O)OR_8$ and $-NR_9S(O_2)R_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_8$, at each occurrence, is independently selected from the group consisting of alkyl, aryl, cycloalkyl, heteroaryl and heterocyclyl, each of which may be optionally substituted with one or more $R_{8a}$'s;

$R_{8a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, $-NH_2$, $-CN$, $-NO_2$, $-C(=O)OH$, $-C(=O)OR_{14}$, $-OCF_3$, $-OR_{14}$, $-OH$, $-SH$, $-SR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2CF_3$, $-C(=O)NR_{14}S(O)_2R_{14}$, $-S(O)_2NR_{14}C(=O)OR_{14}$, $-S(O)_2NR_{14}C(=O)NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=O)R_{14}$, $-C(=NR_{14})NR_{14}R_{14}$, $-NHC(=NR_{14})NR_{14}R_{14}$, $-S(=O)R_{14}$, $-S(O)_2R_{14}$, $=O$, $-NR_{14}C(=O)OR_{14}$ and $-NR_{14}S(O_2)R_{14}$;

$R_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 $R_{9a}$;

$R_{9a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, $-NH_2$, $-CN$, $-NO_2$, $-C(=O)OH$, $-C(=O)OR_{14}$, $-OCF_3$, $-OR_{14}$, $-OH$, $-SH$, $-SR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2CF_3$, $-C(=O)NR_{14}S(O)_2R_{10}$, $-S(O)_2NR_{14}C(=O)OR_{10}$, $-S(O)_2NR_{14}C(=O)NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=O)R_{14}$, $-C(=NR_{14})NR_{14}R_{14}$, $-NHC(=NR_{14})NR_{14}R_{14}$, $-S(=O)R_{14}$, $-S(O)_2R_{14}$, $-NR_{14}C(=O)OR_8$, $-NR_{14}S(O_2)R_8$, $=O$ and arylalkyl;

$R_{10}$, at each occurrence, is independently selected from alkyl, alkenyl, alkynyl cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R_{10a}$;

$R_{10a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, $-NH_2$, $-CN$, $-NO_2$, $-C(=O)OH$, $-C(=O)OR_{14}$, $-OCF_3$, $-OR_{14}$, $-OH$, $-SH$, $-SR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2CF_3$, $-C(=O)NR_{14}S(O)_2R_9$, $-S(O)_2NR_{14}C(=O)OR_9$, $-S(O)_2NR_{14}C(=O)NR_{14}R_{14}$, $-C(=O)NR_{14}S(O)_2CF_3$, $-C(=O)R_{14}$, $-NR_{14}C(=O)H$, $-NR_{14}C(=O)R_{14}$, $-OC(=(O)R_{14}$, $-C(=NR_{14})NR_{14}R_{14}$, $-NHC(=NR_{14})NR_{14}R_{14}$, $-S(=O)R_{14}$, $-S(O)_2R_{14}$, $-NR_{14}C(=O)OR_8$, $-NR_{14}S(O_2)R_8$ and aryl alkyl;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, cycloalkyl, halo, $-CN$, $-C(=O)OH$, $-C(=O)OR_{10}$, $-OCF_3$, $-OR_{10}$, $-OH$, $-C(=O)NR_9R_9$, $-C(=O)R_{10}$ and $-OC(=O)R_{10}$.

In an eighteenth embodiment, a method of modulating the activity of the GPR119 G protein-coupled receptor wherein for the compound of Formula I or Formula IA:

ring A is optionally substituted with one or more R's shown as $R_{20}$ and $R_{21}$;
G is CH or N;
Q is C;
X is CH;
Y is $CH_2$, $N(R_3)$, $C(=O)$, O, $OCR_9R_9$, S, $S(=O)$ or $S(O)_2$;
$n_1$ is 0-2;
$n_2$ is 0-2;
$n_3$ is 1-2;
$R_1$ is a 6-membered monocyclic aryl, a 5-membered monocyclic heteroaryl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1c}$, $R_{1d}$ and $R_{1e}$ are each independently selected from the group consisting of hydrogen, alkyl, alkenyl, alkynyl, cycloalkyl, aryl, heteroaryl, heterocyclyl, halo, $-NH_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_7$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ and —NR$_9$S(O$_2$)R$_8$, wherein the alkyl alkenyl, alkynyl, cycloalkyl, aryl, heteroaryl and heterocyclyl may each be optionally substituted with one or more R$_6$'s; provided that at least one of R$_{1a}$, R$_{1b}$, R$_{1c}$, R$_{1d}$ and R$_{1e}$ is heteroaryl;

R$_2$ is cycloalkyl, aryl, heteroaryl, heterocyclyl, —S(O)$_2$R$_5$, —C(=O)NR$_3$R$_5$, —C(=O)R$_5$ or —C(=O)OR$_5$, wherein the cycloalkyl, aryl, heteroaryl and heterocyclyl may each be optionally substituted with one or more R$_6$'s;

R$_3$ is hydrogen, alkyl, alkoxy, cycloalkyl, aryl, arylalkyl, heteroaryl, heteroarylalkyl, heterocyclyl or heterocyclylalkyl;

R$_5$ is alkyl, alkenyl, aryl, cycloalkyl, heteroaryl or heterocyclyl, each of which may be optionally substituted with one or more R$_6$'s;

R$_6$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_9$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R$_{9a}$;

R$_8$, at each occurrence, is independently selected from the group consisting of alkyl, aryl, cycloalkyl, heteroaryl and heterocyclyl, each of which may be optionally substituted with one or more R$_{8a}$'s;

R$_{8a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$ R$_{14}$, =O, —NR$_{14}$C(=O)OR$_{14}$ and —NR$_{14}$S(O$_2$)R$_{14}$;

R$_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 R$_{9a}$;

R$_{9a}$, at each occurrence, is independently selected from alkyl, haloalkyl aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$ R$_{14}$, —NR$_{14}$C(=O)OR$_8$, —NR$_{14}$S(O$_2$)R$_8$, =O and arylalkyl;

R$_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 R$_{10a}$;

R$_{10a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$) NR$_{14}$R$_{14}$, —NHC(=NR$_{14}$)NR$_{14}$R$_{14}$, —S(=O)R$_{14}$, —S(O)$_2$ R$_{14}$, —NR$_{14}$C(=O)OR$_8$, —NR$_{14}$S(O$_2$)R$_8$ and aryl alkyl;

R$_{14}$, at each occurrence, is independently selected from hydrogen, alkyl, cycloalkyl and aryl;

R$_{20}$ is hydrogen; and

R$_{21}$ is selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

In a nineteenth embodiment, a method of modulating the activity of the GPR119 G protein-coupled receptor wherein for the compound of Formula IA:

ring A is optionally substituted with one or more R's shown as R$_{20}$ and R$_{21}$;

G is CH or N;

Q is C;

X is CH;

Y is CH$_2$, N(R$_3$), C(=O), O, OCR$_9$R$_9$, S, S(=O) or S(O)$_2$;

n$_1$ is 0-2;

n$_2$ is 0-2;

R$_1$ is a 6-membered monocyclic aryl, a 5-membered monocyclic heteroaryl or a 6-membered monocyclic heteroaryl, each of which may be optionally substituted with one or more members selected from R$_{1a}$, R$_{1b}$, R$_{1c}$, R$_{1d}$ and R$_{1e}$;

R$_{1a}$, R$_{1b}$, R$_{1c}$, R$_{1d}$ and R$_{1e}$ are each independently selected from the group consisting of hydrogen, alkyl, alkenyl, alkynyl, cycloalkyl, aryl, heteroaryl, heterocyclyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ and —NR$_9$S(O$_2$)R$_8$, wherein the alkyl alkenyl, alkynyl, cycloalkyl, aryl, heteroaryl and heterocyclyl may each be optionally substituted with one or more R$_6$'s; provided that at least one of R$_{1a}$, R$_{1b}$, R$_{1c}$, R$_{1d}$ and R$_{1e}$ is heteroaryl;

R$_2$ is cycloalkyl, aryl, heteroaryl, heterocyclyl, —S(O)$_2$R$_5$, —C(=O)NR$_3$R$_5$, —C(=O)R$_5$ or C(=O)OR$_5$, wherein the cycloalkyl, aryl, heteroaryl and heterocyclyl may each be optionally substituted with one or more $R_6$'s;

$R_3$ is hydrogen, alkyl, alkoxy, cycloalkyl, aryl, arylalkyl, heteroaryl, heteroarylalkyl, heterocyclyl or heterocyclylalkyl;

$R_5$ is alkyl, alkenyl, aryl, cycloalkyl, heteroaryl or heterocyclyl, each of which may be optionally substituted with one or more $R_6$'s;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —C(=O)OH, —C(=O)$OR_{10}$, —$OCF_3$, —$OR_{10}$, —OH, —SH, —$SR_{10}$, —S(O)$_3$H, —P(O)$_3H_2$, —C(=O)$NR_9R_9$, —$NR_9R_9$, —S(O)$_2NR_9R_9$, —$NR_9S(O)_2CF_3$, —C(=O)$NR_9S(O)_2R_9$, —S(O)$_2NR_9C(=O)OR_9$, —S(O)$_2NR_9C(=O)NR_9R_9$, —C(=O)$NR_9S(O)_2$ $CF_3$, —C(=O)$R_{10}$, —$NR_9C(=O)H$, —$NR_9C(=O)R_{10}$, —OC(=O)$R_{10}$, —C(=$NR_{14}$)$NR_9R_9$, —NHC(=$NR_{14}$)$NR_{14}R_{14}$, —S(=O)$R_{10}$, —S(O)$_2R_{10}$, =O, —$NR_9C(=O)OR_8$ and —$NR_9S(O_2)R_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_8$, at each occurrence, is independently selected from the group consisting of alkyl, aryl, cycloalkyl, heteroaryl and heterocyclyl, each of which may be optionally substituted with one or more $R_{8a}$'s;

$R_{8a}$, at each occurrence, is independently selected from alkyl, haloalkyl, aryl, alkenyl, alkynyl cycloalkyl, cycloalkylalkyl, heteroaryl, heteroarylalkyl, heterocyclyl, heterocyclylalkyl, halo, —$NH_2$, —CN, —$NO_2$, —C(=O)OH, —C(=O)$OR_{14}$, —$OCF_3$, —$OR_{14}$, —OH, —SH, —$SR_{14}$, —S(O)$_3$H, —P(O)$_3H_2$, —C(=O)$NR_{14}R_{14}$, —$NR_{14}R_{14}$, —S(O)$_2$$NR_{14}R_{14}$, —$NR_{14}S(O)_2CF_3$, —C(=O)$NR_{14}S(O)_2R_{14}$, —S(O)$_2NR_{14}C(=O)OR_{14}$, —S(O)$_2NR_{14}C(=O)NR_{14}R_{14}$, —C(=O)$NR_{14}S(O)_2CF_3$, —C(=O)$R_{14}$, —$NR_{14}C(=O)H$, —$NR_{14}C(=O)R_{14}$, —OC(=O)$R_{14}$, —C(=$NR_{14}$)$NR_{14}R_{14}$, —NHC(=$NR_{14}$)$NR_{14}R_{14}$, —S(=O)$R_{14}$, —S(O)$_2$ $R_{14}$, =O, —$NR_{14}C(=O)OR_{14}$ and —$NR_{14}S(O_2)R_{14}$;

$R_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 $R_{9a}$;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —C(=O)OH, —C(=O)$OR_{14}$, —$OCF_3$, —$OR_{14}$, —OH, —SH, —$SR_{14}$, —S(O)$_3$H, —P(O)$_3H_2$—C(=O)$NR_{14}R_{14}$, —$NR_{14}R_{14}$, —S(O)$_2$$NR_{14}R_{14}$, —$NR_{14}S(O)_2CF_3$, —C(=O)$NR_{14}S(O)_2R_{10}$, —S(O)$_2NR_{14}C(=O)OR_{10}$, —S(O)$_7NR_{14}C(=O)NR_{14}R_{14}$, —C(=O)$NR_{14}S(O)_2CF_3$, —C(=O)$R_{14}$, —$NR_{14}C(=O)H$, —$NR_{14}C(=O)R_{14}$, —OC(=O)$R_{14}$, —C($NR_{14}$)$NR_{14}R_{14}$, —NHC(=$NR_{14}$)$NR_{14}R_{14}$, —S(=O)$R_{14}$, —S(O)$_2R_{14}$, —$NR_{14}C(=O)OR_8$, —$NR_{14}S(O_2)R_8$, =O and arylalkyl;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R_{10a}$;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclyl alkyl, halo, —$NH_2$, —CN, —$NO_2$, —C(=O)OH, —C(=O)$OR_{14}$, —$OCF_3$, —$OR_{14}$, —OH, —SH, —$SR_{14}$, —S(O)$_3$H, —P(O)$_3H_2$, —C(=O)$NR_{14}R_{14}$, —$NR_{14}R_{14}$, —S(O)$_2$$NR_{14}R_{14}$, —$NR_{14}S(O)_2CF_3$, —C(=O)$NR_{14}S(O)_2R_9$, —S(O)$_2NR_{14}C(=O)OR_9$, —S(O)$_2NR_{14}C(=O)NR_{14}R_{14}$, —C(=O)$NR_{14}S(O)_2CF_3$, —C(=O)$R_{14}$, —$NR_{14}C(=O)H$, —$NR_{14}C(=O)R_{14}$, —OC(=O)$R_{14}$, —C(=$NR_{14}$)$NR_{14}R_{14}$, —NHC(=$NR_{14}$)$R_{14}R_{14}$, —S(=O)$R_{14}$, —S(O)$_2$ $R_{14}$, —$NR_{14}C(=O)OR_8$, —$NR_{14}S(O_2)R_8$ and arylalkyl;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, cycloalkyl, halo, —CN, —C(=O)OH, —C(=O)$OR_{10}$, —$OCF_3$, —$OR_{10}$, —OH, —C(=O)$NR_9R_9$, —C(=O)$R_{10}$ and —OC(=O)$R_{10}$.

In a twentieth embodiment, a method of modulating the activity of the GPR119 G protein-coupled receptor wherein for the compound of Formula I:

ring A is optionally substituted with one or more R's shown as $R_{20}$ and $R_{21}$;

G is CH or N;

Q is C;

X is CH;

Y is $CH_2$, N($R_3$), C(=O), O, OCR$_9R_9$, S, S(=O) or S(O)$_2$;

$n_1$ is 0-2;

$n_2$ is 0-2;

$n_3$ is 2;

$R_1$ is a 6-membered monocyclic aryl, a 5-membered monocyclic heteroaryl or a 6-membered monocyclic heteroaryl, each of which may be optionally substituted with one or more members selected from $R_{1c}$, $R_{1b}$, $R_{1c}$, $R_{1d}$ and $R_{1e}$;

$R_{1a}$, $R_{1b}$, $R_{1c}$, $R_{1d}$ and $R_{1e}$ are each independently selected from the group consisting of hydrogen, alkyl, alkenyl, alkynyl, cycloalkyl, aryl, heteroaryl, heterocyclyl, halo, —$NH_2$, —CN, —$NO_2$, —C(=O)OH, —C(=O)$OR_{10}$, —$OCF_3$, —$OR_{10}$, —OH, —SH, —$SR_{10}$, —S(O)$_3$H, —P(O)$_3H_2$, —C(=O)$NR_9R_9$, —$NR_9R_9$, —S(O)$_2NR_9R_9$, —$NR_9S(O)_2CF_3$, —C(=O)$NR_9S(O)_2R_9$, —S(O)$_2NR_9C(=O)OR_9$, —S(O)$_2NR_9C(=O)NR_9R_9$, —C(=O)$NR_9S(O)_2CF_3$, —C(=O)$R_{10}$, —$NR_9C(=O)H$, —$NR_9C(=O)R_{10}$, —OC(=O)$R_{10}$, —OC(=O)$NR_9R_9$, —C(=$NR_{14}$)$NR_9R_9$, —NHC(=$NR_{14}$)$NR_{14}R_{14}$, —S(=O)$R_{10}$, —S(O)$_2R_{10}$, —$NR_9C(=O)OR_8$ and —$NR_9S(O_2)R_8$, wherein the alkyl alkenyl, alkynyl, cycloalkyl, aryl, heteroaryl and heterocyclyl may each be optionally substituted with one or more $R_6$'s; provided that at least one of $R_{1a}$, $R_{1b}$, $R_{1c}$, $R_{1d}$ and $R_{1e}$ is heteroaryl;

$R_2$ is cycloalkyl, aryl, heteroaryl, heterocyclyl, —S(O)$_2R_5$, —C(=O)$NR_3R_5$, —C(=O)$R_5$ or —C(=O)$OR_5$, wherein the cycloalkyl, aryl, heteroaryl and heterocyclyl may each be optionally substituted with one or more $R_6$'s;

$R_3$ is hydrogen, alkyl, alkoxy, cycloalkyl, aryl, arylalkyl, heteroaryl, heteroarylalkyl, heterocyclyl or heterocyclylalkyl;

$R_5$ is alkyl, alkenyl, aryl, cycloalkyl, heteroaryl or heterocyclyl, each of which may be optionally substituted with one or more $R_6$'s;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —$NH_2$, —CN, —$NO_2$, —C(=O)OH, —C(=O)$OR_{10}$, —$OCF_3$, —$OR_{10}$, —OH, —SH, —$SR_{10}$, —S(O)$_3$H, —P(O)$_3H_2$, —C(=O)$NR_9R_9$, —$NR_9R_9$, —S(O)$_2NR_9R_9$, —$NR_9S(O)_2CF_3$, —C(=O)$NR_9S(O)_2R_9$, —S(O)$_2NR_9C(=O)OR_9$, —S(O)$_2NR_9C(=O)NR_9R_9$, —C(=O)$NR_9S(O)_2CF_3$, —C(=O)$R_{10}$, —$NR_9C(=O)H$, —$NR_9C(=O)$ $R_{10}$, —OC(=O)$R_{10}$, —C(=N$R_{14}$)N$R_9R_9$, —NHC(=N$R_{14}$)N$R_{14}R_{14}$, —S(=O)$R_{10}$, —S(O)$_2R_{10}$, =O, —N$R_9$C(=O)O$R_8$ and —N$R_9$S(O$_2$)$R_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_8$, at each occurrence, is independently selected from the group consisting of alkyl, aryl, cycloalkyl, heteroaryl and heterocyclyl, each of which may be optionally substituted with one or more $R_{8a}$'s;

$R_{8a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)O$R_{14}$, —OCF$_3$, —O$R_{14}$, —OH, —SH, —S$R_{14}$, —S(O)$_3$H, —P(O)$_3$H$_2$, —C(=O)N$R_{14}R_{14}$, —N$R_{14}R_{14}$, —S(O)$_2$N$R_{14}R_{14}$, —N$R_{14}$S(O)$_2$CF$_3$, —C(=O)N$R_{14}$S(O)$_2R_{14}$, —S(O)$_2$N$R_{14}$C(=O)O$R_{14}$, —S(O)$_2$N$R_{14}$C(=O)N$R_{14}R_{14}$, —C(=O)N$R_{14}$S(=O)CF$_3$, —C(=O)$R_{14}$, —N$R_{14}$C(=O)H, —N$R_{14}$C(=O)$R_{14}$, —OC(=O)$R_{14}$, —C(=N$R_{14}$)N$R_{14}R_{14}$, —NHC(=N$R_{14}$)N$R_{14}R_{14}$, —S(=O)$R_{14}$, —S(O)$_2 R_{14}$, =O, —N$R_{14}$C(=O)O$R_{14}$ and —N$R_{14}$S(O$_2$)$R_{14}$;

$R_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 $R_{9a}$;

$R_{9a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)O$R_{14}$, —OCF$_3$, —O$R_{14}$, —OH, —SH, —S$R_{14}$, —S(O)$_3$H, —P(O)$_3$H$_2$, —C(=O)N$R_{14}R_{14}$, —N$R_{14}R_{14}$, —S(O)$_2$N$R_{14}R_{14}$, —N$R_{14}$S(O)$_2$CF$_3$, —C(=O)N$R_{14}$S(O)—$R_{10}$, —S(O)$_2$N$R_{14}$C(=O)O$R_{10}$, —S(O)$_2$N$R_{14}$C(=O)N$R_{14}R_{14}$, —C(=O)N$R_{14}$S(O)$_2$CF$_3$, —C(=O)$R_{14}$, —N$R_{14}$C(=O)H, —N$R_{14}$C(=O)$R_{14}$, —OC(=O)$R_{14}$, —C(=N$R_{14}$)N$R_{14}R_{14}$, —NHC(=N$R_{14}$)N$R_{14}R_{14}$, —S(=O)$R_{14}$, —S(O)$_2 R_{14}$, —N$R_{14}$C(=O)O$R_8$, —N$R_{14}$S(O$_2$)$R_8$, =O and arylalkyl;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R_{10a}$;

$R_{10a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)O$R_{14}$, —OCF$_3$, —O$R_{14}$, —OH, —SH, —S$R_{14}$, —S(O)$_3$H, —P(O)$_3$H$_2$, —C(=O)N$R_{14}R_{14}$, —N$R_{14}R_{14}$, —S(O)$_2$N$R_{14}R_{14}$, —N$R_{14}$S(O)$_2$CF$_3$, —C(=O)N$R_{14}$S(O)$_2R_9$, —S(O)$_2$N$R_{14}$C(=O)O$R_9$, —S(O)$_2$N$R_{14}$C(=O)N$R_{14}R_{14}$, —C(=O)N$R_{14}$S(O)$_2$CF$_3$, —C(=O)$R_{14}$, —N$R_{14}$C(=O)H, —N$R_{14}$C(=O)$R_{14}$, —OC(=O)$R_{14}$, —C(=N$R_{14}$)N$R_{14}R_{14}$, —NHC(=N$R_{14}$)N$R_{14}R_{14}$, —S(=O)$R_{14}$, —S(O)$_2 R_{14}$, —N$R_{14}$C(=O)O$R_8$, —N$R_{14}$S(O$_2$)$R_8$ and arylalkyl;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, cycloalkyl, halo, —CN, —C(=O)OH, —C(=O)O$R_{10}$, —OCF$_3$, —O$R_{10}$, —OH, —C(=O)N$R_9R_9$, —C(=O)$R_{10}$ and —OC(=O)$R_{10}$.

In a twenty-first embodiment, a method of modulating the activity of the GPR119 G protein-coupled receptor wherein for the compound of Formula IA:

ring A is optionally substituted with one or more R's shown as $R_{20}$ and $R_{21}$;

G is CH or N;

Q is C;

X is CH;

Y is CH$_2$, N(R$_3$), C(=O), O, OCR$_9R_9$, S, S(=O) or S(O)$_2$;

$n_1$ is 1;

$n_2$ is 1;

$R_1$ is a 6-membered monocyclic aryl, a 5-membered monocyclic heteroaryl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1c}$, $R_{1d}$ and $R_{1e}$ are each independently selected from the group consisting of hydrogen, alkyl, alkenyl, alkynyl, cycloalkyl, aryl, heteroaryl, heterocyclyl, halo, —NH$_2$, —CN, —NO$_2$, —C(=O)OH, —C(=O)O$R_{10}$, —OCF$_3$, —O$R_{10}$, —OH, —SH, —S$R_{10}$, —S(O)$_3$H, —P(O)$_3$H$_2$, —C(=O)N$R_9R_9$, —N$R_9R_9$, —S(O)$_2$N$R_9R_9$, —N$R_9$S(O)$_2$CF$_3$, —C(=O)N$R_9$S(O)$_2R_9$, —S(O)$_2$N$R_9$C(=O)O$R_9$, —S(O)$_2$N$R_9$C(=O)N$R_9R_9$, —C(=O)N$R_9$S(O)$_2$CF$_3$, —C(=O)$R_{10}$, —N$R_9$C(=O)H, —N$R_9$C(=O)$R_{10}$, —OC(=O)$R_{10}$, —OC(=O)N$R_9R_9$, —C(=N$R_{14}$)N$R_9R_9$, —NHC(=N$R_{14}$)N$R_{14}R_{14}$, —S(=O)$R_{10}$, —S(O)$_2R_{10}$, —N$R_9$C(=HO)O$R_8$ and —N$R_9$S(O$_2$)$R_8$, wherein the alkyl alkenyl, alkynyl, cycloalkyl, aryl, heteroaryl and heterocyclyl may each be optionally substituted with one or more $R_6$'s; provided that at least one of $R_{1a}$, $R_{1b}$, $R_{1c}$, $R_{1d}$ and $R_{1e}$ is heteroaryl;

$R_2$ is cycloalkyl, aryl, heteroaryl, heterocyclyl, —S(O)$_2R_5$, —C(=O)N$R_3R_5$, —C(=O)$R_5$ or C(=O)O$R_5$, wherein the cycloalkyl, aryl, heteroaryl and heterocyclyl may each be optionally substituted with one or more $R_6$'s;

$R_3$ is hydrogen, alkyl, alkoxy, cycloalkyl, aryl, arylalkyl, heteroaryl, heteroarylalkyl, heterocyclyl or heterocyclylalkyl;

$R_5$ is alkyl, alkenyl, aryl, cycloalkyl, heteroaryl or heterocyclyl, each of which may be optionally substituted with one or more $R_6$;

$R_6$, at each occurrence, is independently selected from alkyl, haloalkyl aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)O$R_{10}$, —OCF$_3$, —O$R_{10}$, —OH, —SH, —S$R_{10}$, —S(O)$_3$H, —P(O)$_3$H$_2$, —C(=O)N$R_9R_9$, —N$R_9R_9$, —S(O)$_2$N$R_9R_9$, —N$R_9$S(O)$_2$CF$_3$, —C(=O)N$R_9$S(O)$_2R_9$, —S(O)$_2$N$R_9$C(=O)O$R_9$, —S(O)$_2$N$R_9$C(=O)N$R_9R_9$, —C(=O)N$R_9$S(O)$_2$ CF$_3$, —C(=O)$R_{10}$, —N$R_9$C(=O)H, —N$R_9$C(=O)$R_{10}$, —OC(=O)$R_{10}$, —C(=N$R_{14}$)N$R_9R_9$, —NHC(=N$R_{14}$)N$R_{14}R_{14}$, —S(=O)$R_{10}$, —S(O)$_2R_{10}$, =O, —N$R_9$C(=O)O$R_8$ and —N$R_9$S(O$_2$)$R_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_8$, at each occurrence, is independently selected from the group consisting of alkyl, aryl, cycloalkyl, heteroaryl and heterocyclyl, each of which may be optionally substituted with one or more $R_{8a}$'s;

$R_{8a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)O$R_{14}$, —OCF$_3$, —O$R_{14}$, —OH, —SH, —S$R_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, =O, —NR$_{14}$C(=O)OR$_{14}$ and —NR$_{14}$S(O)$_2$R$_{14}$;

R$_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 R$_{9a}$;

R$_{9a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O)$_2$R$_8$, =O and arylalkyl;

R$_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 R$_{10a}$;

R$_{10a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O)$_2$R$_8$ and arylalkyl;

R$_{14}$, at each occurrence, is independently selected from hydrogen, alkyl, cycloalkyl and aryl;

R$_{20}$ is hydrogen; and

R$_{21}$ is selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

In a twenty-second embodiment, a method of modulating the activity of the GPR119 G protein-coupled receptor wherein for the compound of Formula I:

ring A is optionally substituted with one or more R's shown as R$_{20}$ and R$_{21}$;

G is CH or N;

Q is C;

X is CH;

Y is CH$_2$, N(R$_3$), C(=O), O, OCR$_9$R$_9$, S, S(=O) or S(O)$_2$;

n$_1$ is 1;

n$_2$ is 1;

n$_3$ is 2;

R$_1$ is a 6-membered monocyclic aryl, a 5-membered monocyclic heteroaryl or a 6-membered monocyclic heteroaryl, each of which may be optionally substituted with one or more members selected from R$_{1a}$, R$_{1b}$, R$_{1c}$, R$_{1d}$ and R$_{1e}$;

R$_{1a}$, R$_{1b}$, R$_{1c}$, R$_{1d}$ and R$_{1e}$ are each independently selected from the group consisting of hydrogen, alkyl, alkenyl, alkynyl, cycloalkyl, aryl, heteroaryl, heterocyclyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ and —NR$_9$S(O$_2$)R$_8$, wherein the alkyl alkenyl, alkynyl, cycloalkyl, aryl, heteroaryl and heterocyclyl may each be optionally substituted with one or more R$_6$'s; provided that at least one of R$_{1a}$, R$_{1b}$, R$_{1c}$, R$_{1d}$ and R$_{1e}$ is heteroaryl;

R$_2$ is cycloalkyl, aryl, heteroaryl heterocyclyl, —S(O)$_2$R$_5$, —C(=O)NR$_3$R$_5$, —C(=O)R$_5$ or —C(=O)OR$_5$, wherein the cycloalkyl, aryl, heteroaryl and heterocyclyl may each be optionally substituted with one or more R$_6$'s;

R$_3$ is hydrogen, alkyl, alkoxy, cycloalkyl, aryl, arylalkyl, heteroaryl, heteroarylalkyl, heterocyclyl or heterocyclylalkyl;

R$_5$ is alkyl, alkenyl, aryl, cycloalkyl, heteroaryl or heterocyclyl, each of which may be optionally substituted with one or more R$_6$'s;

R$_6$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R$_{9a}$;

R$_8$, at each occurrence, is independently selected from the group consisting of alkyl, aryl, cycloalkyl, heteroaryl and heterocyclyl, each of which may be optionally substituted with one or more R$_{8a}$'s;

R$_{8a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, =O, —NR$_{14}$C(=O)OR$_{14}$ and —NR$_{14}$S(O)$_2$R$_{14}$;

R$_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 R$_{9a}$;

$R_{9a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —$NH_2$, —CN, —$NO_2$, —C(=O)OH, —C(=O)OR$_{14}$, —OCF$_3$, —OR$_{14}$, —OH, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$, =O and arylalkyl;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R_{10a}$;

$R_{10a}$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —$NH_2$, —CN, —$NO_2$, —C(=O)OH, —C(=O)OR$_{14}$, —OCF$_3$, —OR$_{14}$, —O, —SH, —SR$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_9$, —S(O)$_2$NR$_{14}$C(=O)OR$_9$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —C(NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ and arylalkyl;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

In a twenty-third embodiment, a method of modulating the activity of the GPR119 G protein-coupled receptor wherein for the compound of Formula IA:

ring A is optionally substituted with one or more R's shown as $R_{20}$ and $R_{21}$;

G is CH or N;

Q is C;

X is CH;

Y is CH$_2$, N(R$_3$), C(=O), O, OCR$_9$R$_9$, S, S(=O) or S(O)$_2$;

$n_1$ is 1;

$n_2$ is 1;

$R_1$ is a 6-membered monocyclic aryl, a 5-membered monocyclic heteroaryl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1c}$, $R_{1d}$ and $R_{1e}$ are each independently selected from the group consisting of hydrogen, alkyl, alkenyl, alkynyl, cycloalkyl, aryl, heteroaryl, heterocyclyl, halo, —$NH_2$, —CN, —$NO_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$—C(=O)R$_{10}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ and —NR$_9$S(O$_2$)R$_8$, wherein the alkyl alkenyl, alkynyl, cycloalkyl, aryl, heteroaryl and heterocyclyl may each be optionally substituted with one or more $R_6$'s; provided that at least one of $R_{1a}$, $R_{1b}$, $R_{1c}$, $R_{1d}$ and $R_{1e}$ is heteroaryl;

$R_2$ is cycloalkyl, aryl, heteroaryl, heterocyclyl, —S(O)$_2$R$_5$, —C(=O)NR$_3$R$_5$, —C(=O)R$_5$ or —C(=O)OR$_5$, wherein the cycloalkyl, aryl, heteroaryl and heterocyclyl may each be optionally substituted with one or more $R_6$'s;

$R_3$ is hydrogen, alkyl, alkoxy, cycloalkyl, aryl, arylalkyl, heteroaryl, heteroarylalkyl, heterocyclyl or heterocyclylalkyl;

$R_5$ is alkyl, alkenyl, aryl, cycloalkyl, heteroaryl or heterocyclyl, each of which may be optionally substituted with one or more $R_6$'s;

$R_6$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —$NH_2$, —CN, —$NO_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$ CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_8$, at each occurrence, is independently selected from the group consisting of alkyl, aryl, cycloalkyl, heteroaryl and heterocyclyl, each of which may be optionally substituted with one or more $R_{8a}$'s;

$R_{8a}$, at each occurrence, is independently selected from alkyl, haloalkyl, aryl alkenyl, alkynyl, cycloalkyl, halo, —$NH_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, =O, —NR$_{14}$C(=O)OR$_{14}$ and —NR$_{14}$S(O$_2$)R$_{14}$;

$R_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 $R_{9a}$;

$R_{9a}$, at each occurrence, is independently selected from alkyl, haloalkyl, aryl, alkenyl, alkynyl, cycloalkyl, halo, —$NH_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$, =O;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R_{10a}$;

$R_{10a}$, at each occurrence, is independently selected from alkyl, haloalkyl, aryl, alkenyl, alkynyl, halo, —$NH_2$, —CN, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

In a twenty-fourth embodiment, a method of modulating the activity of the GPR119 G protein-coupled receptor wherein for the compound of Formula I:

ring A is optionally substituted with one or more R's shown as $R_{20}$ and $R_{21}$;

G is CH or N;

Q is C;

X is CH;

Y is CH$_2$, N(R$_3$), C(=O), O, OCR$_9$R$_9$, S, S(=O) or S(O)$_2$;

$n_1$ is 1;

$n_2$ is 1;

$n_3$ is 2;

$R_1$ is a 6-membered monocyclic aryl, a 5-membered monocyclic heteroaryl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1c}$, $R_{1d}$ and $R_{1e}$ are each independently selected from the group consisting of hydrogen, alkyl, alkenyl, alkynyl, cycloalkyl, aryl, heteroaryl, heterocyclyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —CO(NR$_{14}$)NR$_9$R$_9$, —NHC(NR$_{14}$)NR$_{14}$R$_{14}$, —S(=O)R$_{10}$, —S(O)$_2$R$_{10}$, —NR$_9$C(=O)OR$_8$ and —NR$_9$S(O$_2$)R$_8$, wherein the alkyl, alkenyl, alkynyl, cycloalkyl, aryl, heteroaryl and heterocyclyl may each be optionally substituted with one or more $R_6$'s; provided that at least one of $R_{1a}$, $R_{1b}$, $R_{1c}$, $R_{1d}$ and $R_{1e}$ is heteroaryl;

$R_2$ is cycloalkyl, aryl, heteroaryl, heterocyclyl, —S(O)$_2$R$_5$, —C(=O)NR$_3$R$_5$, —C(=O)R$_5$ or —C(=O)OR$_5$, wherein the cycloalkyl, aryl, heteroaryl and heterocyclyl may each be optionally substituted with one or more $R_6$'s;

$R_3$ is hydrogen, alkyl, alkoxy, cycloalkyl, aryl, arylalkyl, heteroaryl, heteroarylalkyl, heterocyclyl or heterocyclylalkyl;

$R_5$ is alkyl, alkenyl, aryl, cycloalkyl, heteroaryl or heterocyclyl, each of which may be optionally substituted with one or more $R_6$'s;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$COO)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_8$, at each occurrence, is independently selected from the group consisting of alkyl, aryl, cycloalkyl, heteroaryl and heterocyclyl, each of which may be optionally substituted with one or more $R_{8a}$'s;

$R_{8a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$, —S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, =O, —NR$_{14}$C(=O)OR$_{14}$ and —NR$_{14}$S(O$_2$)R$_{14}$;

$R_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 $R_{9a}$;

$R_{9a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$, =O;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R_{10a}$;

$R_{10a}$, at each occurrence, is independently selected from alkyl, haloalkyl, aryl, alkenyl, alkynyl, halo, —NH$_2$, —CN, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

In a twenty-fifth embodiment, a method of modulating the activity of the GPR119 G protein-coupled receptor wherein for the compound of Formula IA:

ring A is optionally substituted with one or more R's shown as $R_{20}$ and $R_{21}$;

G is CH or N;

Q is C;

X is CH;

Y is O, OCR$_9$R$_9$, or S;

$n_1$ is 1;

$n_2$ is 1;

$R_1$ is a 6-membered monocyclic aryl, a 5-membered monocyclic heteroaryl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1c}$, $_{R1d}$ and $R_{1e}$ are each independently selected from the group consisting of hydrogen, alkyl, alkenyl, alkynyl, cycloalkyl, aryl, heteroaryl, heterocyclyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_9$ and —NR$_9$S(O$_2$)R$_9$, wherein the alkyl alkenyl, alkynyl, cycloalkyl, aryl, heteroaryl and heterocyclyl may each be optionally substituted with one or more R$_6$'s; provided that at least one of R$_{1a}$, R$_{1b}$, R$_{1c}$, R$_{1d}$ and R$_{1e}$ is heteroaryl;

R$_2$ is cycloalkyl, aryl, heteroaryl, heterocyclyl, —S(O)$_2$R$_5$, —C(=O)NR$_3$R$_5$, —C(=O)R$_5$ or —C(=O)OR$_5$, wherein the cycloalkyl, aryl, heteroaryl and heterocyclyl may each be optionally substituted with one or more R$_6$'s;

R$_3$ is hydrogen, alkyl, alkoxy, cycloalkyl, aryl, arylalkyl, heteroaryl, heteroarylalkyl, heterocyclyl or heterocyclylalkyl;

R$_5$ is alkyl, alkenyl, aryl, cycloalkyl, heteroaryl or heterocyclyl, each of which may be optionally substituted with one or more R$_6$'s;

R$_6$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$ CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R$_{9a}$;

R$_8$, at each occurrence, is independently selected from the group consisting of alkyl, aryl, cycloalkyl, heteroaryl and heterocyclyl, each of which may be optionally substituted with one or more R$_{8a}$'s;

R$_{8a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, =O, —NR$_{14}$C(=O)OR$_{14}$ and —NR$_{14}$S(O$_2$)R$_{14}$;

R$_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 R$_{9a}$;

R$_{9a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$, =O;

R$_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 R$_{10a}$;

R$_{10a}$, at each occurrence, is independently selected from alkyl, haloalkyl, aryl, alkenyl, alkynyl, halo, —NH$_2$, —CN, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$;

R$_{14}$, at each occurrence, is independently selected from hydrogen, alkyl, cycloalkyl and aryl;

R$_{20}$ is hydrogen; and

R$_{21}$ is selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

In a twenty-sixth embodiment, a method of modulating the activity of the GPR119 G protein-coupled receptor wherein for the compound of Formula I:

ring A is optionally substituted with one or more R's shown as R$_{20}$ and R$_{21}$;

G is CH or N;

Q is C;

X is CH;

Y is O, OCR$_9$R$_9$ or S;

n$_1$ is 1;

n$_2$ is 1;

n$_3$ is 2;

R$_1$ is a 6-membered monocyclic aryl, a 5-membered monocyclic heteroaryl or a 6-membered monocyclic heteroaryl, each of which may be optionally substituted with one or more members selected from R$_{1a}$, R$_{1b}$, R$_{1c}$, R$_{1d}$ and R$_{1e}$;

R$_{1a}$, R$_{1b}$, R$_{1c}$, R$_{1d}$ and R$_{1e}$ are each independently selected from the group consisting of hydrogen, alkyl, alkenyl, alkynyl, cycloalkyl, aryl, heteroaryl, heterocyclyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ and —NR$_9$S(O$_2$)R$_8$, wherein the alkyl alkenyl, alkynyl, cycloalkyl, aryl, heteroaryl and heterocyclyl may each be optionally substituted with one or more R$_6$'s; provided that at least one of R$_{1a}$, R$_{1b}$, R$_{1c}$, R$_{1d}$ and R$_{1e}$ is heteroaryl;

R$_2$ is cycloalkyl, aryl, heteroaryl, heterocyclyl, —S(O)$_2$R$_5$, —C(=O)NR$_3$R$_5$, —C(=O)R$_5$ or —C(=O)OR$_5$, wherein the cycloalkyl, aryl, heteroaryl and heterocyclyl may each be optionally substituted with one or more R$_6$'s;

R$_3$ is hydrogen, alkyl, alkoxy, cycloalkyl, aryl, arylalkyl, heteroaryl, heteroarylalkyl, heterocyclyl or heterocyclylalkyl;

R$_5$ is alkyl, alkenyl, aryl, cycloalkyl, heteroaryl or heterocyclyl, each of which may be optionally substituted with one or more R$_6$'s;

R$_6$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$ CF$_3$—C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R$_{9a}$;

$R_8$, at each occurrence, is independently selected from the group consisting of alkyl, aryl, cycloalkyl, heteroaryl and heterocyclyl, each of which may be optionally substituted with one or more $R_{8a}$'s;

$R_{8a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, =O, —NR$_{14}$C(=O)OR$_{14}$ and —NR$_{14}$S(O)$_2$R$_{14}$;

$R_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 $R_{9a}$;

$R_{9a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O)$_2$R$_8$, =O;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R_{10a}$;

$R_{10a}$, at each occurrence, is independently selected from alkyl, haloalkyl, aryl, alkenyl, alkynyl, halo, —NH$_2$, —CN, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O)$_2$R$_8$;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

In a twenty-seventh embodiment, a method of modulating the activity of the GPR119 G protein-coupled receptor wherein for the compound of Formula IA:

ring A is optionally substituted with one or more R's shown as $R_{20}$ and $R_{21}$;

G is CH or N;

Q is C;

X is CH;

Y is O, OCR$_9$R$_9$ or S;

$n_1$ is 1;

$n_2$ is 1;

$R_1$ is phenyl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1c}$, $R_{1d}$ and $R_{1e}$ are each independently selected from the group consisting of hydrogen, alkyl, alkenyl, alkyl, cycloalkyl, aryl, heteroaryl, heterocyclyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —C(=NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ and —NR$_9$S(O)$_2$R$_8$, wherein the alkyl alkenyl, alkynyl, cycloalkyl, aryl, heteroaryl and heterocyclyl may each be optionally substituted with one or more $R_6$'s; provided that at least one of $R_{1a}$, $R_{1b}$, $R_{1c}$, $R_{1d}$ and $R_{1e}$ is heteroaryl;

$R_2$ is heteroaryl or —C(=O)OR$_5$, wherein the heteroaryl may be optionally substituted with one or more $R_6$'s;

$R_5$ is alkyl, alkenyl, aryl, cycloalkyl, heteroaryl or heterocyclyl, each of which may be optionally substituted with one or more $R_6$'s;

$R_6$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$ CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O)$_2$R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_8$, at each occurrence, is independently selected from the group consisting of alkyl, aryl, cycloalkyl, heteroaryl and heterocyclyl, each of which may be optionally substituted with one or more $R_{8a}$'s;

$R_{8a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, =O, —NR$_{14}$C(=O)OR$_{14}$ and —NR$_{14}$S(O)$_2$R$_{14}$;

$R_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 $R_{9a}$;

$R_{9a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O)$_2$R$_8$, =O;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R_{10a}$;

$R_{10a}$, at each occurrence, is independently selected from alkyl, haloalkyl, aryl, alkenyl, alkynyl, halo, —NH$_2$, —CN, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O)$_2$R$_8$;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

In a twenty-eighth embodiment, a method of modulating the activity of the GPR119 G protein-coupled receptor wherein for the compound of Formula I:

ring A is optionally substituted with one or more R's shown as $R_{20}$ and $R_{21}$;

C is CH or N;

Q is C;

X is CH;

Y is O, OCR$_9$R$_9$ or S;

$n_1$ is 1;

$n_2$ is 1;

$n_3$ is 2;

$R_1$ is phenyl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1c}$, $R_{1d}$ and $R_{1e}$ are each independently selected from the group consisting of hydrogen, alkyl, alkenyl, alkynyl, cycloalkyl, aryl, heteroaryl heterocyclyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$—C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(=O)NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —C(NR$_{14}$)NR$_9$R$_9$, —NHC(=NR$_{14}$)NR$_{14}$R$_{14}$, —S(=O)R$_{10}$, —S(O)$_2$R$_{10}$, —NR$_9$C(=O)OR$_8$ and —NR$_9$S(O$_2$)R$_8$, wherein the alkyl alkenyl, alkynyl, cycloalkyl, aryl, heteroaryl and heterocyclyl may each be optionally substituted with one or more R$_6$'s; provided that at least one of $R_{1a}$, $R_{1b}$, $R_{1c}$, $R_{1d}$ and $R_{1e}$ is heteroaryl;

$R_2$ is heteroaryl or —C(=O)OR$_5$, wherein the heteroaryl may be optionally substituted with one or more R$_6$'s;

$R_5$ is alkyl, alkenyl, aryl, cycloalkyl, heteroaryl or heterocyclyl, each of which may be optionally substituted with one or more R$_6$'s;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —NH$_2$, —CN, —NO$_2$, —C(=O)OH, —C(=O)OR$_{10}$, —OCF$_3$, —OR$_{10}$, —OH, —SH, —SR$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$CF$_3$, —C(=O)NR$_9$S(O)$_2$R$_9$, —S(O)$_2$NR$_9$C(=O)OR$_9$, —S(O)$_2$NR$_9$C(=O)NR$_9$R$_9$, —C(HO)NR$_9$S(O)$_2$CF$_3$, —C(=O)R$_{10}$, —NR$_9$C(=O)H, —NR$_9$C(=O)R$_{10}$, —OC(=O)R$_{10}$, —C(=NR$_{14}$)NR$_9$R$_9$, —NHC(=NR$_{14}$)NR$_{14}$R$_{14}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R$_{9a}$;

$R_8$, at each occurrence, is independently selected from the group consisting of alkyl, aryl, cycloalkyl, heteroaryl and heterocyclyl, each of which may be optionally substituted with one or more R$_{8a}$'s;

$R_{8a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O) H, —NR$_{14}$C(=O)R$_{14}$, —OC(=O)R$_{14}$, —S(=O)R$_{14}$, —S(O)$_2$R$_{14}$, =O, —NR$_{14}$C(=O)OR$_{14}$ and —NR$_{14}$S(O$_2$) R$_{14}$;

$R_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 R$_{9a}$;

$R_{9a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O) H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$ and =O;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 R$_{10a}$;

$R_{10a}$, at each occurrence, is independently selected from alkyl, haloalkyl, aryl, alkenyl, alkynyl, halo, —NH$_2$, —CN, —C(=O)OR$_{14}$, —OCF$_3$, —OR$_{14}$, —OH, —C(=O) NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$ and —NR$_{14}$S(O$_2$)R$_8$;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

In a twenty-ninth embodiment, a method of modulating the activity of the GPR119 G protein-coupled receptor wherein for the compound of Formula IA ring A is optionally substituted with one or more R's shown as $R_{20}$ and $R_{21}$;

G is CH or N;

Q is C;

X is CH;

Y is O, OCR$_9$R$_9$, or S;

$n_1$ is 1;

$n_2$ is 1;

$R_1$ is phenyl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1d}$ and $R_{1e}$ are each independently selected from the group consisting of hydrogen, alkyl, alkenyl, alkynyl, cycloalkyl, halo, —CN, —OCF$_3$, —OR$_{10}$, —OH, —C(=O) NR$_9$R$_9$, —NR$_9$R$_9$, —S(O)$_2$NR$_9$R$_9$, —NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —S(=O)R$_{10}$, —S(O)$_2$R$_{10}$, —NR$_9$C(=O)OR$_8$ and —NR$_9$S(O$_2$)R$_8$, wherein the alkyl, alkenyl, alkynyl and cycloalkyl may each be optionally substituted with one or more R$_6$'s;

$R_{1c}$ is a 5-6 membered monocyclic heteroaryl which may be optionally substituted with one or more R$_6$'s;

$R_2$ is heteroaryl or —C(=O)OR$_5$, wherein the heteroaryl may be optionally substituted with one or more R$_6$'s;

$R_5$ is alkyl, alkenyl, aryl, cycloalkyl, heteroaryl or heterocyclyl, each of which may be optionally substituted with one or more R$_6$'s;

$R_6$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —CN, —C(=O)$OR_{10}$, —$OCF_3$, —$OR_{10}$, —OH, —SH, —$SR_{10}$, —C(=O)$NR_9R_9$, —$NR_9R_9$, —$S(O)_2NR_9R_9$, —$NR_9S(O)_2CF_3$, —C(=O)$R_{10}$, —$NR_9C$(=O)H, —$NR_9C$(=O)$R_{10}$, —OC(=O)$R_{10}$, —S(=O)$R_{10}$, —$S(O)_2R_{10}$, =O, —$NR_9C$(=O)$OR_8$ and —$NR_9S(O)_2R_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_8$, at each occurrence, is independently selected from the group consisting of alkyl, aryl, cycloalkyl, heteroaryl and heterocyclyl, each of which may be optionally substituted with one or more $R_{8a}$'s;

$R_{8a}$, at each occurrence, is independently selected from alkyl, haloalkyl, aryl, alkenyl, alkynyl, cycloalkyl, halo, —$NH_2$, —CN, —C(=O)OH, —C(=O)$R_{14}$, —$OCF_3$, —$OR_{14}$, —OH, —C(=O)$NR_{14}R_{14}$, —$NR_{14}R_{14}$, —$S(O)_2NR_{14}R_{14}$, —$NR_{14}S(O)_2CF_3$, —C(=O)$R_{14}$, —$NR_{14}C$(=O)H, —$NR_{14}C$(=O)$R_{14}$, —OC(=O)$R_{14}$, —S(=O)$R_{14}$, —$S(O)_2R_{14}$, =O, —$NR_{14}C$(=O)$OR_{14}$ and —$NR_{14}S(O)_2R_{14}$;

$R_9$, at each occurrence, is independently selected from hydrogen, alkyl alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 $R_{9a}$;

$R_{9a}$, at each occurrence, is independently selected from alkyl, haloalkyl, aryl, alkenyl, alkynyl, cycloalkyl, halo, —$NH_2$, —CN, —C(=O)OH, —C(=O)$OR_{14}$, —$OCF_3$, —$OR_{14}$, —OH, —C(=O)$NR_{14}R_{14}$, —$NR_{14}R_{14}$, —$S(O)_2NR_{14}R_{14}$, —$NR_{14}S(O)_2CF_3$, —C(=O)$R_{14}$, —$NR_{14}C$(=O)H, —$NR_{14}C$(=O)$R_{14}$, —OC(=O)$R_{14}$, —S(=O)$R_{14}$, —$S(O)_2R_{14}$, —$NR_{14}C$(=O)$OR_8$, —$NR_{14}S(O)_2R_8$ and =O;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R_{10a}$;

$R_{10a}$, at each occurrence, is independently selected from alkyl, haloalkyl, aryl, alkenyl, alkynyl, halo, —$NH_2$, —CN, —C(=O)$OR_{14}$, —$OCF_3$, —$OR_{14}$, —OH, —C(=O)$NR_{14}R_{14}$, —$NR_{14}R_{14}$, —$S(O)_2NR_{14}R_{14}$, —$NR_{14}S(O)_2CF_3$, —C(=O)$R_{14}$, —$NR_{14}C$(=O)H, —$NR_{14}C$(=O)$R_{14}$, —OC(=O)$R_{14}$, —S(=O)$R_{14}$, —$S(O)_2R_{14}$, —$NR_{14}C$(=O)$OR_8$ and —$NR_{14}S(O)_2R_8$;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, cycloalkyl, halo, —CN, —C(=O)OH, —C(=O)$OR_{10}$, —$OCF_3$, —$OR_{10}$, —OH, —C(=O)$NR_9R_9$, —C(=O)$R_{10}$ and —OC(=O)$R_{10}$.

In a thirtieth embodiment, a method of modulating the activity of the GPR119 G protein-coupled receptor wherein for the compound of Formula I:

ring A is optionally substituted with one or more R's shown as $R_{20}$ and $R_{21}$;

G is CH or N;

Q is C;

X is CH;

Y is O, $OCR_9R_9$, or S;

$n_1$ is 1;

$n_2$ is 1;

$n_3$ is 2;

$R_1$ is phenyl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1d}$ and $R_{1e}$ are each independently selected from the group consisting of hydrogen, alkyl, alkenyl, alkynyl, cycloalkyl, halo, —CN, —$OCF_3$, —$OR_{10}$, —OH, —C(=O)$NR_9R_9$, —$NR_9R_9$, —$S(O)_2NR_9R_9$, —$NR_9S(O)_2CF_3$, —C(=O)$R_{10}$, —$NR_9C$(=O)H, —$NR_9C$(=O)$R_{10}$, —OC(=O)$R_{10}$, —OC(=O)$NR_9R_9$, —S(=O)$R_{10}$, —$S(O)_2R_{10}$, —$NR_9C$(=O)$OR_8$ and —$NR_9S(O)_2R_8$, wherein the alkyl, alkenyl, alkynyl and cycloalkyl may each be optionally substituted with one or more $R_6$'s;

$R_{1c}$ is a 5-6 membered monocyclic heteroaryl which may be optionally substituted with one or more $R_6$'s;

$R_2$ is heteroaryl or —C(=O)$OR_5$, wherein the heteroaryl may be optionally substituted with one or more $R_6$'s;

$R_5$ is alkyl, alkenyl, aryl, cycloalkyl, heteroaryl or heterocyclyl, each of which may be optionally substituted with one or more $R_6$'s;

$R_6$, at each occurrence, is independently selected from alkyl, haloalkyl aryl, alkenyl, alkynyl, cycloalkyl, cycloalkyl alkyl, heteroaryl, heteroarylalkyl, heterocyclyl, heterocyclyl alkyl, halo, —CN, —C(=O)$OR_{10}$, —$OCF_3$, —$OR_{10}$, —OH, —SH, —$SR_{10}$, —C(=O)$NR_9R_9$, —$NR_9R_9$, —$S(O)_2NR_9R_9$, —$NR_9S(O)_2CF_3$, —C(=O)$R_{10}$, —$NR_9C$(=O)H, —$NR_9C$(=O)$R_{10}$, —OC(=O)$R_{10}$, —S(=O)$R_{10}$, —$S(O)_2R_{10}$, =O, —$NR_9C$(=O)$OR_8$ and —$NR_9S(O)_2R_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_8$, at each occurrence, is independently selected from the group consisting of alkyl, aryl, cycloalkyl, heteroaryl and heterocyclyl, each of which may be optionally substituted with one or more $R_{8a}$'s;

$R_{8a}$, at each occurrence, is independently selected from alkyl, haloalkyl, aryl, alkenyl, alkynyl, cycloalkyl, halo, —$NH_2$, —CN, —C(=O)OH, —C(=O)$OR_{14}$, —$OCF_3$, —$OR_{14}$, —OH, —C(=O)$NR_{14}R_{14}$, —$NR_{14}R_{14}$, —$S(O)_2NR_{14}R_{14}$, —$NR_{14}S(O)_2CF_3$, —C(=O)$R_{14}$, —$NR_{14}C$(=O)H, —$NR_{14}C$(=O)$R_{14}$, —OC(=O)$R_{14}$, —S(=O)$R_{14}$, —$S(O)_2R_{14}$, =O, —$NR_{14}C$(=O)$OR_{14}$ and —$NR_{14}S(O)_2R_{14}$;

$R_9$, at each occurrence, is independently selected from hydrogen, alkyl, alkoxy, cycloalkyl, aryl, arylalkyl, heteroaryl, heteroarylalkyl, heterocyclyl and heterocyclylalkyl, wherein the alkyl, cycloalkyl, aryl, arylalkyl, heteroaryl, heteroarylalkyl, heterocyclyl and heterocyclylalkyl may each be optionally substituted with 0-5 $R_{9a}$;

$R_{9a}$, at each occurrence, is independently selected from alkyl, haloalkyl, aryl, alkenyl, alkynyl, cycloalkyl, halo, —$NH_2$, —CN, —C(=O)OH, —C(=O)$OR_{14}$, —$OCF_3$, —$OR_{14}$, —OH, —C(=O)$NR_{14}R_{14}$, —$NR_{14}R_{14}$, —$S(O)_2NR_{14}R_{14}$, —$NR_{14}S(O)_2CF_3$, —C(=O)$R_{14}$, —$NR_{14}C$(=O)H, —$NR_{14}C$(=O)$R_{14}$, —OC(=O)$R_{14}$, —S(=O)$R_{14}$, —$S(O)_2R_{14}$, —$NR_{14}C$(=O)$OR_8$, —$NR_{14}S(O)_2R_8$ and =O;

$R_{10}$, at each occurrence, is independently selected from alkyl, alkenyl, alkynyl, cycloalkyl, aryl, arylalkyl, heteroaryl, heteroarylalkyl, heterocyclyl and heterocyclylalkyl, wherein the cycloalkyl, aryl, arylalkyl, heteroaryl, heteroarylalkyl, heterocyclyl and heterocyclylalkyl may each be optionally substituted with 0-3 $R_{10a}$;

$R_{10a}$, at each occurrence, is independently selected from alkyl, haloalkyl, aryl, alkenyl, alkynyl, halo, —$NH_2$, —CN, —C(=O)$OR_{14}$, —$OCF_3$, —$OR_{14}$, —OH, —C(=O)$NR_{14}R_{14}$, —$NR_{14}R_{14}$, —$S(O)_2NR_{14}R_{14}$, —$NR_{14}S(O)_2CF_3$, —C(=O)$R_{14}$, —$NR_{14}$C(=O)H, —$NR_{14}$C(=O)$R_{14}$, —OC(=O)$R_{14}$, —S(=O)$R_{14}$, —S(O)$_2$$R_{14}$, —$NR_{14}$C(=O)$OR_8$ and —$NR_{14}$S(O)$_2$$R_8$;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, cycloalkyl, halo, —CN, —C(=O)OH, —C(=O)$OR_{10}$, —$OCF_3$, —$OR_{10}$, —OH, —C(=O)$NR_9R_9$, —C(=O)$R_{10}$ and —OC(=O)$R_{10}$.

In a thirty-first embodiment, a method of modulating the activity of the GPR119 G protein-coupled receptor wherein for the compound of Formula IA:

ring A is optionally substituted with one or more R's shown as $R_{20}$ and $R_{21}$;

G is CH or N;

Q is C;

X is CH;

Y is O, OCR$_9$R$_9$ or S;

$n_1$ is 1;

$n_2$ is 1;

$R_1$ is phenyl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1d}$ and $R_{1e}$ are each independently selected from the group consisting of hydrogen, alkyl, alkenyl, alkynyl, cycloalkyl, halo, —CN, —$OCF_3$, —$OR_{10}$, —OH, —C(=O)$NR_9R_9$, —$NR_9R_9$, —S(O)$_2$$NR_9R_9$, —$NR_9$S(O)$_2$$CF_3$, —C(=O)$R_{10}$, —$NR_9$C(=O)H, —$NR_9$C(=O)$R_{10}$, —OC(=O)$R_{10}$, —OC(=O)$NR_9R_9$, —S(=O)$R_{10}$, —S(O)$_2$$R_{10}$, —$NR_9$C(=O)$OR_8$ and —$NR_9$S(O$_2$)$R_8$, wherein the alkyl, alkenyl, alkynyl and cycloalkyl may each be optionally substituted with one or more $R_6$'s;

$R_{1c}$ is a 5-6 membered monocyclic heteroaryl which may be optionally substituted with one or more $R_6$'s;

$R_7$ is heteroaryl or —C(=O)$OR_5$, wherein the heteroaryl may be optionally substituted with one or more $R_6$'s;

$R_5$ is alkyl, alkenyl, aryl, cycloalkyl, heteroaryl or heterocyclyl, each of which may be optionally substituted with one or more $R_6$'s;

$R_6$, at each occurrence, is independently selected from alkyl, haloalkyl, aryl, alkenyl alkynyl, cycloalkyl, cycloalkyl alkyl, heteroaryl, heteroarylalkyl, heterocyclyl, heterocyclyl alkyl, halo, —CN, —C(=O)$OR_{10}$, —$OCF_3$, —$OR_{10}$, —OH, —SH, —$SR_{10}$, —C(=O)$NR_9R_9$, —$NR_9R_9$, —S(O)$_2$$NR_9R_9$, —$NR_9$S(O)$_2$$CF_3$, —C(=O)$R_{10}$, —$NR_9$C(=O)H, —$NR_9$C(=O)$R_{10}$, —OC(=O)$R_{10}$, —S(=O)$R_{10}$, —S(O)$_2$$R_{10}$, =O, —$NR_9$C(=O)$OR_8$ and —$NR_9$S(O$_2$)$R_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_8$, at each occurrence, is independently selected from the group consisting of alkyl and cycloalkyl, each of which may be optionally substituted with one or more $R_{8a}$'s;

$R_{8a}$, at each occurrence, is independently selected from alkyl, haloalkyl, aryl, alkenyl, alkynyl, cycloalkyl, halo, —$NH_2$, —CN, —C(=O)OH, —C(=O)$OR_{14}$, —$OCF_3$, —$OR_{14}$, —OH, —C(=O)$NR_{14}R_{14}$, —$NR_{14}R_{14}$, —S(O)$_2$$NR_{14}R_{14}$, —$NR_{14}$S(O)$_2$$CF_3$, —C(=O)$R_{14}$, —$NR_{14}$C(=O)H, —$NR_{14}$C(=O)$R_{14}$, —OC(=O)$R_{14}$, —S(=O)$R_{14}$, —S(O)$_2$$R_{14}$, =O, —$NR_{14}$C(=O)$OR_{14}$ and —$NR_{14}$S(O$_2$)$R_{14}$;

$R_9$, at each occurrence, is independently selected from hydrogen, alkyl, cycloalkyl, and aryl, wherein the alkyl, cycloalkyl, and aryl may each be optionally substituted with 0-5 $R_{9a}$;

$R_{9a}$, at each occurrence, is independently selected from alkyl, haloalkyl, aryl, alkenyl, alkynyl, cycloalkyl, halo, —$NH_2$, —CN, —C(=O)OH, —C(=O)$OR_{14}$, —$OCF_3$, —$OR_{14}$, —OH, —C(=O)$NR_{14}R_{14}$, —$NR_{14}R_{14}$, —S(O)$_2$$NR_{14}R_{14}$, —$NR_{14}$S(O)$_2$$CF_{37}$—C(=O)$R_{14}$, —$NR_{14}$C(=O)H, —$NR_{14}$C(=O)$R_{14}$, —OC(=O)$R_{14}$, —S(=O)$R_{14}$, —S(O)$_2$$R_{14}$, —$NR_{14}$C(=O)$OR_8$, —$NR_{14}$S(O)$_2$$R_8$ and =O;

$R_{10}$, at each occurrence, is independently selected from alkyl, cycloalkyl, and aryl, which may each be optionally substituted with 0-3 $R_{10a}$;

$R_{10a}$, at each occurrence, is independently selected from alkyl, haloalkyl, aryl, alkenyl, alkynyl, halo, —$NH_2$, —CN, —C(=O)$OR_{14}$, —$OCF_3$, —$OR_{14}$, —OH, —C(=O)$NR_{14}R_{14}$, —$NR_{14}R_{14}$, —S(O)$_2$$NR_{14}R_{14}$, —$NR_{14}$S(O)$_2$$CF_3$, —C(=O)$R_{14}$, —$NR_{14}$C(=O)H, —$NR_{14}$C(=O)$R_{14}$, —OC(=O)$R_{14}$, —S(=O)$R_{14}$, —S(O)$_2$$R_{14}$, —$NR_{14}$C(=O)$OR_8$ and —$NR_{14}$S(O$_2$)$R_8$;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, cycloalkyl, halo, —CN, —C(=O)OH, —C(=O)$OR_{10}$, —$OCF_3$, —$OR_{10}$, —OH, —C(=O)$NR_9R_9$, —C(=O)$R_{10}$ and —OC(=O)$R_{10}$.

In a thirty-second embodiment, a method of modulating the activity of the GPR119 G protein-coupled receptor wherein for the compound of Formula I:

ring A is optionally substituted with one or more R's shown as $R_{20}$ and $R_{12}$;

G is CH or N;

Q is C;

X is CH;

Y is O, OCR$_9$R$_9$ or S;

$n_1$ is 1;

$n_2$ is 1;

$n_3$ is 2;

$R_1$ is phenyl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1d}$ and $R_{1e}$ are each independently selected from the group consisting of hydrogen, alkyl, alkenyl, alkynyl, cycloalkyl, halo, —CN, —$OCF_3$, —$OR_{10}$, —OH, —C(=O)$NR_9R_9$, —$NR_9R_9$, —S(O)$_2$$NR_9R_9$, —$NR_9$S(O)$_2$$CF_3$, —C(=O)$R_{10}$, —$NR_9$C(=O)H, —$NR_9$C(=O)$R_{10}$, —OC(=O)$R_{10}$, —OC(=O)$NR_9R_9$, —S(=O)$R_{10}$, —S(O)$_2$$R_{10}$, —$NR_9$C(=O)$OR_8$ and —$NR_9$S(O$_2$)$R_8$, wherein the alkyl, alkenyl, alkynyl and cycloalkyl may each be optionally substituted with one or more $R_6$'s;

$R_{1c}$ is a 5-6 membered monocyclic heteroaryl which may be optionally substituted with one or more $R_6$'s;

$R_2$ is heteroaryl or —C(=O)$OR_5$, wherein the heteroaryl may be optionally substituted with one or more $R_6$'s;

$R_5$ is alkyl, alkenyl, aryl, cycloalkyl, heteroaryl or heterocyclyl, each of which may be optionally substituted with one or more $R_6$'s;

$R_6$, at each occurrence, is independently selected from alkyl, haloalkyl, aryl, alkenyl, alkynyl, cycloalkyl, cycloalkyl alkyl heteroaryl, heteroarylalkyl, heterocyclyl, heterocyclyl alkyl, halo, —CN, —C(=O)$OR_{10}$, —$OCF_3$, —$OR_{10}$, —OH, —SH, —$SR_{10}$, —C(=O)$NR_9R_9$, —$NR_9R_9$, —S(O)$_2$$NR_9R_9$, —$NR_9$S(O)$_2$$CF_3$, —C(=O)$R_{10}$, —$NR_9$C(=O)H, —$NR_9$C(=O)$R_{10}$, —OC(=O)$R_{10}$, —S(=O)$R_{10}$, —S(O)$_7$$R_{10}$, =O, —$NR_9$C(=O)$OR_8$ and —$NR_9$S(O$_2$)$R_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_8$, at each occurrence, is independently selected from the group consisting of alkyl and cycloalkyl, each of which may be optionally substituted with one or more $R_{8a}$'s;

$R_{8a}$, at each occurrence, is independently selected from alkyl, haloalkyl, aryl, alkenyl, alkynyl, cycloalkyl, halo, —$NH_2$, —CN, —C(=O)OH, —C(=O)$OR_{14}$, —$OCF_3$, —$OR_{14}$, —OH, —C(=O)$NR_{14}R_{14}$, —$NR_{14}R_{14}$, —S(O)$_2$$NR_{14}R_{14}$, —$NR_{14}S(O)_2CF_3$, —C(=O)$R_{14}$, —$NR_{14}C(=O)$H, —$NR_{14}C(=O)R_{14}$, —OC(=O)$R_{14}$, —S(=O)$R_{14}$, —S(O)$_2R_{14}$, =O, —$NR_{14}C(=O)OR_{14}$ and —$NR_{14}S(O_2)R_{14}$;

$R_9$, at each occurrence, is independently selected from hydrogen, alkyl, cycloalkyl and aryl, wherein the alkyl, cycloalkyl and aryl may each be optionally substituted with 0-5 $R_{9a}$;

$R_{9a}$, at each occurrence, is independently selected from alkyl, haloalkyl, aryl, alkenyl, alkynyl, cycloalkyl, halo, —$NH_2$, —CN, —C(=O)OH, —C(=O)$OR_{14}$, —$OCF_3$, —$OR_{14}$, —OH, —C(=O)$NR_{14}R_{14}$, —$NR_{14}R_{14}$, —S(O)$_2$$NR_{14}R_{14}$, —$NR_{14}S(O)_2CF_3$, —C(=O)$R_{14}$, —$NR_{14}C(=O)$H, —$NR_{14}C(=O)R_{14}$, —OC(=O)$R_{14}$, —S(=O)$R_{14}$, —S(O)$_2R_{14}$, —$NR_{14}C(=O)OR_8$, —$NR_{14}S(O_2)R_8$ and =O;

$R_{10}$, at each occurrence, is independently selected from alkyl, cycloalkyl and aryl, which may each be optionally substituted with 0-3 $R_{10a}$;

$R_{10a}$, at each occurrence, is independently selected from alkyl, haloalkyl, aryl, alkenyl, alkynyl, halo, —$NH_2$, —CN, —C(=O)$OR_{14}$, —$OCF_3$, —$OR_{14}$, —OH, —C(=O)$NR_{14}R_{14}$, —$NR_{14}R_{14}$, —S(O)$_2NR_{14}R_{14}$, —$NR_{14}S(O)_2CF_3$, —C(=O)$R_{14}$, —$NR_{14}C(=O)$H, —$NR_{14}C(=O)R_{14}$, —OC(=O)$R_{14}$, —S(=O)$R_{14}$, —S(O)$_2R_{14}$, —$NR_{14}C(=O)OR_8$ and —$NR_{14}S(O_2)R_8$;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, cycloalkyl, halo, —CN, —C(=O)OH, —C(=O)$OR_{10}$, —$OCF_3$, —$OR_{10}$, —OH, —C(=O)$NR_9R_9$, —C(=O)$R_{10}$ and —OC(=O)$R_{10}$.

In a thirty-third embodiment, a method of modulating the activity of the GPR119 G protein-coupled receptor wherein for the compound of Formula IA:

ring A is optionally substituted with one or more R's shown as $R_{20}$ and $R_{21}$;

G is N;

Q is C;

X is CH;

Y is O, OCR$_9R_9$ or S;

$n_1$ is 1;

$n_2$ is 1

$R_1$ is phenyl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1d}$ and $R_{1e}$ are each independently selected from the group consisting of hydrogen, alkyl, alkenyl, alkynyl, cycloalkyl, halo, —CN, —$OCF_3$, —$OR_{10}$, —OH, —C(=O)$NR_9R_9$, —$NR_9R_9$, —S(O)$_2NR_9R_9$, —$NR_9S(O)_2CF_3$, —C(=O)$R_{10}$, —$NR_9C(=O)$H, —$NR_9C(=O)R_{10}$, —OC(=O)$R_{10}$, —OC(=O)$NR_9R_9$, —S(=O)$R_{10}$, —S(O)$_2R_{10}$, —$NR_9C(=O)OR_8$ and —$NR_9S(O_2)R_8$, wherein the alkyl, alkenyl, alkynyl and cycloalkyl may each be optionally substituted with one or more $R_6$'s;

$R_{1c}$ is a 5-6 membered monocyclic heteroaryl which may be optionally substituted with one or more $R_6$'s;

$R_2$ is heteroaryl or —C(=O)$OR_5$, wherein the heteroaryl may be optionally substituted with one or more $R_6$'s;

$R_5$ is alkyl, alkenyl, aryl, cycloalkyl, heteroaryl or heterocyclyl, each of which may be optionally substituted with one or more $R_6$'s;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —C(=O)$OR_{10}$, —$OCF_3$, —$OR_{10}$, —OH, —SH, —$SR_{10}$, —C(=O)$NR_9R_9$, —$NR_9R_9$, —S(O)$_2NR_9R_9$, —$NR_9S(O)_2CF_3$, —C(=O)$R_{10}$, —$NR_9C(=O)$H, —$NR_9C(=O)R_{10}$, —OC(=O)$R_{10}$, —S(=O)$R_{10}$, —S(O)$_2R_{10}$, =O, —$NR_9C(=O)OR_8$ and —$NR_9S(O_2)R_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_8$, at each occurrence, is independently selected from the group consisting of alkyl and cycloalkyl, each of which may be optionally substituted with one or more $R_{8a}$'s;

$R_{8a}$, at each occurrence, is independently selected from alkyl, haloalkyl, aryl, alkenyl, alkynyl, cycloalkyl, halo, —$NH_2$, —CN, —C(=O)OH, —C(=O)$OR_{14}$, —$OCF_3$, —$OR_{14}$, —OH, —C(=O)$NR_{14}R_{14}$, —$NR_{14}R_{14}$, —S(O)$_2$$NR_{14}R_{14}$, —$NR_{14}S(O)_2CF_3$, —C(=O)$R_{14}$, —$NR_{14}C(=O)$H, —$NR_{14}C(=O)R_{14}$, —OC(=O)$R_{14}$, —S(=O)$R_{14}$, —S(O)$_2R_{14}$, =O, —$NR_{14}C(=O)OR_{14}$ and —$NR_{14}S(O_2)R_{14}$;

$R_9$, at each occurrence, is independently selected from hydrogen, alkyl, cycloalkyl and aryl, wherein the alkyl, cycloalkyl and aryl may each be optionally substituted with 0-5 $R_{9a}$;

$R_{9a}$, at each occurrence, is independently selected from alkyl, haloalkyl, aryl, alkenyl, alkynyl, cycloalkyl, halo, —$NH_2$, —CN, —C(=O)OH, —C(=O)$OR_{14}$, —$OCF_3$, —$OR_{14}$, —OH, —C(=O)$NR_{14}R_{14}$, —$NR_{14}R_{14}$, —S(O)$_2$$NR_{14}R_{14}$, —$NR_{14}S(O)_2CF_3$, —C(=O)$R_{14}$, —$NR_{14}C(=O)$H, —$NR_{14}C(=O)R_{14}$, —OC(=O)$R_{14}$, —S(=O)$R_{14}$, —S(O)$_2R_{14}$, —$NR_{14}C(=O)OR_8$, —$NR_{14}S(O_2)R_8$ and =O;

$R_{10}$, at each occurrence, is independently selected from alkyl, cycloalkyl, and aryl, which may each be optionally substituted with 0-3 $R_{10a}$;

$R_{10a}$, at each occurrence, is independently selected from alkyl, haloalkyl, aryl, alkenyl, alkynyl, halo, —$NH_2$, —CN, —C(=O)$OR_{14}$, —$OCF_3$, —$OR_{14}$, —OH, —C(=O)$NR_{14}R_{14}$, —$NR_{14}R_{14}$, —S(O)$NR_{14}R_{14}$, —$NR_{14}S(O)_2CF_3$, —C(=O)$R_{14}$, —$NR_{14}C(=O)$H, —$NR_{14}C(=O)R_{14}$, —OC(=O)$R_{14}$, —S(=O)$R_{14}$, —S(O)$_2R_{14}$, —$NR_{14}C(=O)OR_8$ and —$NR_{14}S(O_2)R_8$;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, cycloalkyl, halo, —CN, —C(=O)OH, —C(=O)$OR_{10}$, —$OCF_3$, —$OR_{10}$, —OH, —C(=O)$NR_9R_9$, —C(=O)$R_{10}$ and —OC(=O)$R_{10}$.

In a thirty-fourth embodiment, a method of modulating the activity of the GPR119 G protein-coupled receptor wherein for the compound of Formula I:

ring A is optionally substituted with one or more R's shown as $R_{20}$ and $R_{21}$;

G is N;

Q is C;

X is CH;

Y is O, OCR$_9R_9$ or S;

$n_1$ is 1;

$n_2$ is 1;

$n_3$ is 2;

$R_1$ is phenyl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1d}$ and $R_{1e}$ are each independently selected from the group consisting of hydrogen, alkyl, alkenyl, alkynyl, cycloalkyl, halo, —CN, —OCF$_3$, —OR$_{10}$, —OH, —C(=O)NR$_9$R$_9$, —NR$_9$R$_9$, —S(O)$_2$NR$_9$R$_9$, —NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —S(=O)R$_{10}$, —S(O)$_2$R$_{10}$, —NR$_9$C(=O)OR$_8$ and —NR$_9$S(O$_2$)R$_8$, wherein the alkyl, alkenyl, alkynyl and cycloalkyl may each be optionally substituted with one or more R$_6$'s;

$R_{1c}$ is a 5-6 membered monocyclic heteroaryl which may be optionally substituted with one or more R$_6$'s;

$R_2$ is heteroaryl or —C(=O)OR$_5$, wherein the heteroaryl may be optionally substituted with one or more R$_6$'s;

$R_5$ is alkyl, alkenyl, aryl, cycloalkyl, heteroaryl or heterocyclyl, each of which may be optionally substituted with one or more R$_6$'s;

$R_6$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —CN, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)R$_{10}$, —NR$_9$C(=O)H, —NR$_9$C(=O)R$_{10}$, —OC(=O)R$_{10}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkyl, aryl, cycloalkyl, cycloalkylalkyl, heteroaryl, heteroarylalkyl, heterocyclyl and heterocyclylalkyl may each be optionally substituted with 0-5 R$_{9a}$;

$R_8$, at each occurrence, is independently selected from the group consisting of alkyl and cycloalkyl, each of which may be optionally substituted with one or more R$_{8a}$'s;

$R_{8a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, =O, —NR$_{14}$C(=O)OR$_{14}$ and —NR$_{14}$S(O$_2$)R$_{14}$;

$R_9$, at each occurrence, is independently selected from hydrogen, alkyl, cycloalkyl and aryl, wherein the alkyl, cycloalkyl and aryl may each be optionally substituted with 0-5 R$_{9a}$;

$R_{9a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$ and =O;

$R_{10}$, at each occurrence, is independently selected from alkyl, cycloalkyl, and aryl, which may each be optionally substituted with 0-3 R$_{10a}$;

$R_{10a}$, at each occurrence, is independently selected from alkyl, haloalkyl, aryl, alkenyl, alkynyl, halo, —NH$_2$, —CN, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$ and —NR$_{14}$S(O$_2$)R$_8$;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, cycloalkyl, halo, —CN, —C(=O)OH, —C(=O)OR$_{10}$, —OCF$_3$, —OR$_{10}$, —OH, —C(=O)NR$_9$R$_9$, —C(=O)R$_{10}$ and —OC(=O)R$_{10}$.

In a thirty-fifth embodiment, a method of modulating the activity of the GPR119 G protein-coupled receptor wherein for the compound of Formula IA:

ring A is optionally substituted with one or more R's shown as $R_{20}$ and $R_{21}$;

G is N;

Q is C;

X is CH;

Y is O;

$n_1$ is 1;

$n_2$ is 1;

$R_1$ is phenyl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1d}$ and $R_{1e}$ are each independently selected from the group consisting of hydrogen, alkyl, alkenyl, alkynyl, cycloalkyl, halo, —CN, —OCF$_3$, —OR$_{10}$, —OH, —C(=O)NR$_9$R$_9$, —NR$_9$R$_9$, —S(O)$_2$NR$_9$R$_9$, —NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —S(=O)R$_{10}$, —S(O)$_2$R$_{10}$, —NR$_9$C(=O)OR$_8$ and —NR$_9$S(O$_2$)R$_9$, wherein the alkyl, alkenyl, alkynyl and cycloalkyl may each be optionally substituted with one or more R$_6$'s;

$R_{1c}$ is a 5-6 membered monocyclic heteroaryl which may be optionally substituted with one or more R$_6$'s;

$R_2$ is heteroaryl or —C(=O)OR$_5$, wherein the heteroaryl may be optionally substituted with one or more R$_6$'s;

$R_5$ is alkyl, alkenyl, aryl, cycloalkyl, heteroaryl or heterocyclyl, each of which may be optionally substituted with one or more R$_6$'s;

$R_6$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —CN, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)R$_{10}$, —NR$_9$C(=O)H, —NR$_9$C(=O)R$_{10}$, —OC(=O)R$_{10}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl alkynyl, aryl, cycloalkyl, cycloalkylalkyl, heteroaryl, heteroarylalkyl, heterocyclyl and heterocyclylalkyl may each be optionally substituted with 0-5 R$_{9a}$;

$R_8$, at each occurrence, is independently selected from the group consisting of alkyl and cycloalkyl, each of which may be optionally substituted with one or more R$_{8a}$'s;

$R_{8a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, =O, —NR$_{14}$C(=O)OR$_{14}$ and —NR$_{14}$S(O$_2$)R$_{14}$;

$R_9$, at each occurrence, is independently selected from hydrogen, alkyl, cycloalkyl and aryl, wherein the alkyl, cycloalkyl and aryl may each be optionally substituted with 0-5 R$_{9a}$;

$R_{9a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$ and =O;

$R_{10}$, at each occurrence, is independently selected from alkyl, cycloalkyl, and aryl, which may each be optionally substituted with 0-3 $R_{10a}$;

$R_{10a}$, at each occurrence, is independently selected from alkyl, haloalkyl, aryl, alkenyl, alkynyl, halo, —$NH_2$, —CN, —C(=O)$OR_{14}$, —$OCF_3$, —$OR_{14}$, —OH, —C(=O)$NR_{14}R_{14}$, —$NR_{14}R_{14}$, —S(O)$_2NR_{14}R_{14}$, —$NR_{14}S(O)_2CF_3$, —C(=O)$R_{14}$, —$NR_{14}C$(=O)H, —$NR_{14}C$(=O)$R_{14}$, —OC(=O)$R_{14}$, —S(=O)$R_{14}$, —S(O)$_2R_{14}$, —$NR_{14}C$(=O)$OR_8$ and —$NR_{14}S(O)_2R_8$;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, cycloalkyl, halo, —CN, —C(=O)OH, —C(=O)$OR_{10}$, —$OCF_3$, —$OR_{10}$, —OH, —C(=O)$NR_9R_9$, —C(=O)$R_{10}$ and —OC(=O)$R_{10}$.

In a thirty-sixth embodiment, a method of modulating the activity of the GPR119 G protein-coupled receptor wherein for the compound of Formula I:

ring A is optionally substituted with one or more R's shown as $R_{20}$ and $R_{21}$;

G is N;
Q is C;
X is CH;
Y is O;
$n_1$ is 1;
$n_2$ is 1;
$n_3$ is 2;

$R_1$ is phenyl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1d}$ and $R_{1e}$ are each independently selected from the group consisting of hydrogen, alkyl, alkenyl, alkyl, cycloalkyl, halo, —CN, —$OCF_3$, —$OR_{10}$, —OH, —C(=O)$NR_9R_9$, —$NR_9R_9$, —S(O)$_2NR_9R_9$, —$NR_9S(O)_2CF_3$, —C(=O)$R_{10}$, —$NR_9C$(=O)H, —$NR_9C$(=O)$R_{10}$, —OC(=O)$R_{10}$, —OC(=O)$NR_9R_9$, —S(=O)$R_{10}$, —S(O)$_2R_{10}$, —$NR_9C$(=O)$OR_8$ and —$NR_9S(O)_2R_8$, wherein the alkyl, alkenyl, alkynyl and cycloalkyl may each be optionally substituted with one or more $R_6$'s;

$R_{1c}$ is a 5-6 membered monocyclic heteroaryl which may be optionally substituted with one or more $R_6$'s;

$R_2$ is heteroaryl or —C(=O)$OR_5$, wherein the heteroaryl may be optionally substituted with one or more $R_6$'s;

$R_5$ is alkyl, alkenyl, aryl, cycloalkyl, heteroaryl or heterocyclyl, each of which may be optionally substituted with one or more $R_6$'s;

$R_6$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —CN, —C(=O)$OR_{10}$, —$OCF_3$, —$OR_{10}$, —OH, —SH, —$SR_{10}$, —C(=O)$NR_9R_9$, —$NR_9R_9$, —S(O)$_2NR_9R_9$, —$NR_9S(O)_2CF_3$, —C(=O)$R_{10}$, —$NR_9C$(=O)H, —$NR_9C$(=O)$R_{10}$, —OC(=O)$R_{10}$, —S(=O)$R_{10}$, —S(O)$_2R_{10}$, =O, —$NR_9C$(=O)$OR_8$ and —$NR_9S(O)_2R_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_8$, at each occurrence, is independently selected from the group consisting of alkyl and cycloalkyl, each of which may be optionally substituted with one or more $R_{8a}$'s;

$R_{8a}$, at each occurrence, is independently selected from alkyl, haloalkyl, aryl, alkenyl, alkynyl, cycloalkyl, halo, —$NH_2$, —CN, —C(=O)OH, —C(=O)$OR_{14}$, —$OCF_3$, —$OR_{14}$, —OH, —C(=O)$NR_{14}R_{14}$, —$NR_{14}R_{14}$, —S(O)$_2NR_{14}R_{14}$, —$NR_{14}S(O)_2CF_3$, —C(=O)$R_{14}$, —$NR_{14}C$(=O)H, —$NR_{14}C$(=O)$R_{14}$, —OC(=O)$R_{14}$, —S(=O)$R_{14}$, —S(O)$_2R_{14}$, =O, —$NR_{14}C$(=O)$OR_{14}$ and —$NR_{14}S(O)_2R_{14}$;

$R_9$, at each occurrence, is independently selected from hydrogen, alkyl, cycloalkyl and aryl, which may each be optionally substituted with 0-5 $R_{9a}$;

$R_{9a}$, at each occurrence, is independently selected from alkyl, haloalkyl, aryl, alkenyl, alkynyl, cycloalkyl, halo, —$NH_2$, —CN, —C(=O)OH, —C(=O)$OR_{14}$, —$OCF_3$, —$OR_{14}$, —OH, —C(=O)$NR_{14}R_{14}$, —$NR_{14}R_{14}$, —S(O)$_2NR_{14}R_{14}$, —$NR_{14}S(O)_2CF_3$, —C(=O)$R_{14}$, —$NR_{14}C$(=O)H, —$NR_{14}C$(=O)$R_{14}$, —OC(=O)$R_{14}$, —S(=O)$R_{14}$, —S(O)$_2R_{14}$, —$NR_{14}C$(=O)$OR_8$, —$NR_{14}S(O)_2R_8$ and =O;

$R_{10}$, at each occurrence, is independently selected from alkyl, cycloalkyl and aryl, which may each be optionally substituted with 0-3 $R_{10a}$;

$R_{10a}$, at each occurrence, is independently selected from alkyl, haloalkyl, aryl, alkenyl, alkynyl, halo, —$NH_2$, —CN, —C(=O)$OR_{14}$, —$OCF_3$, —$OR_{14}$, —OH, —C(=O)$NR_{14}R_{14}$, —$NR_{14}R_{14}$, —S(O)$_2NR_{14}R_{14}$, —$NR_{14}S(O)_2CF_3$, —C(=O)$R_{14}$, —$NR_{14}C$(=O)H, —$NR_{14}C$(=O)$R_{14}$, —OC(=O)$R_{14}$, —S(=O)$R_{14}$, —S(O)$_2R_{14}$, —$NR_{14}C$(=O)$OR_8$ and —$NR_{14}S(O)_2R_8$;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, cycloalkyl, halo, —CN, —C(=O)OH, —C(=O)$OR_{10}$, —$OCF_3$, —$OR_{10}$, —OH, —C(=O)$NR_9R_9$, —C(=O)$R_{10}$ and —OC(=O)$R_{10}$.

In a thirty-seventh embodiment, a method of modulating the activity of the GPR119 G protein-coupled receptor wherein for the compound of Formula IA:

ring A is optionally substituted with one or more R's shown as $R_{20}$ and $R_{21}$;

G is N;
Q is C;
X is CH;
Y is O;
$n_1$ is 1;
$n_2$ is 1;

$R_1$ is phenyl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1d}$ and $R_{1e}$ are each independently selected from the group consisting of hydrogen, alkyl, alkenyl, alkynyl, cycloalkyl, halo, —CN, —$OCF_3$, —$OR_{10}$, —OH, —C(=O)$NR_9R_9$, —$NR_9R_9$, —S(O)$_2NR_9R_9$, —$NR_9S(O)_2CF_3$, —C(=O)$R_{10}$, —$NR_9C$(=O))H, —$NR_9C$(=O)$R_{10}$, —OC(=O)$R_{10}$, —OC(=O)$NR_9R_9$, —S(=O)$R_{10}$, —S(O)$_2R_{10}$, —$NR_9C$(=O)$OR_8$ and —$NR_9S(O)_2R_8$, wherein the alkyl, alkenyl, alkynyl and cycloalkyl may each be optionally substituted with one or more $R_6$'s;

$R_{1c}$ is a 5-6 membered monocyclic heteroaryl which may be optionally substituted with one or more $R_6$'s;

$R_2$ is heteroaryl or C(=O)$OR_5$, wherein the heteroaryl may be optionally substituted with one or more $R_6$'s;

$R_5$ is alkyl, alkenyl, aryl, cycloalkyl, heteroaryl or heterocyclyl, each of which may be optionally substituted with one or more $R_6$'s;

$R_6$, at each occurrence, is independently selected from alkyl, haloalkyl, aryl, alkenyl, alkynyl, cycloalkyl, cycloalkyl alkyl, heteroaryl, heteroarylalkyl, heterocyclyl, heterocyclyl alkyl, halo, —CN, —C(=O)$OR_{10}$, —$OCF_3$, —$OR_{10}$, —OH, —SH, —$SR_{10}$, —C(=O)$NR_9R_9$, —$NR_9R_9$, —S(O)$_2NR_9R_9$, —$NR_9S(O)_2CF_3$, —C(=O)$R_{10}$, —$NR_9C$(=O)H, —$NR_9C$(=O)$R_{10}$, —OC(=O)$R_{10}$, —S(=O)$R_{10}$, —S(O)$_2$ $R_{10}$, =O, —$NR_9C(=O)OR_8$ and —$NR_9S(O_2)R_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_8$, at each occurrence, is independently selected from the group consisting of alkyl and cycloalkyl, each of which may be optionally substituted with one or more $R_{8a}$'s;

$R_{8a}$, at each occurrence, is independently selected from alkyl, haloalkyl, aryl, alkenyl, alkynyl, cycloalkyl, halo, —$NH_2$, —CN, —C(=O)OH, —C(=O)$OR_{14}$, —$OCF_3$, —$OR_{14}$, —OH, —C(=O)$NR_{14}R_{14}$, —$NR_{14}R_{14}$, —$S(O)_2NR_{14}R_{14}$, —$NR_{14}S(O)_2CF_3$, —C(=O)$R_{14}$, —$NR_{14}C(=O)H$, —$NR_{14}C(=O)R_{14}$, —OC(=O)$R_{14}$, —S(=O)$R_{14}$, —$S(O)_2R_{14}$, =O, —$NR_{14}C(=O)OR_{14}$ and —$NR_{14}S(O_2)R_{14}$;

$R_9$, at each occurrence, is independently selected from hydrogen, alkyl, cycloalkyl and aryl, wherein the alkyl, cycloalkyl and aryl may each be optionally substituted with 0-5 $R_{9a}$;

$R_{9a}$, at each occurrence, is independently selected from alkyl, haloalkyl, aryl, alkenyl, alkynyl, cycloalkyl, halo, —$NH_2$, —CN, —C(=O)OH, —C(=O)$OR_{14}$, —$OCF_3$, —$OR_{14}$, —OH, —C(=O)$NR_{14}R_{14}$, —$NR_{14}R_{14}$, —$S(O)_2NR_{14}R_{14}$, —$NR_{14}S(O)_2CF_3$, —C(=O)$R_{14}$, —$NR_{14}C(=O)H$, —$NR_{14}C(=O)R_{14}$, —OC(=O)$R_{14}$, —S(=O)$R_{14}$, —$S(O)_2R_{14}$, —$NR_{14}C(=O)OR_8$, —$NR_{14}S(O_2)R_8$ and =O;

$R_{10}$, at each occurrence, is independently selected from alkyl, cycloalkyl and aryl, which may each be optionally substituted with 0-3 $R_{10a}$;

$R_{10a}$, at each occurrence, is independently selected from alkyl, haloalkyl, aryl, alkenyl, alkynyl, halo, —$NH_2$, —CN, —C(=O)$OR_{14}$, —$OCF_3$, —$OR_{14}$, —OH, —C(=O)$NR_{14}R_{14}$, —$NR_{14}R_{14}$, —$S(O)_2NR_{14}R_{14}$, —$NR_{14}S(O)_2CF_3$, —C(=O)$R_{14}$, —$NR_{14}C(=O)H$, —$NR_{14}C(=O)R_{14}$, —OC(=O)$R_{14}$, —S(=O)$R_{14}$, —$S(O)_2R_{14}$, —$NR_{14}C(=O)OR_8$ and —$NR_{14}S(O_2)R_8$;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, halo and —CN.

In a thirty-eighth embodiment, a method of modulating the activity of the GPR119 G protein-coupled receptor wherein for the compound of Formula I:

ring A is optionally substituted with one or more R's shown as $R_{20}$ and $R_{21}$;

G is N;
Q is C;
X is CH;
Y is O;
$n_1$ is 1;
$n_2$ is 1;
$n_3$ is 2;

$R_1$ is phenyl or a 6-membered monocyclic heteroaryl, each of which may be optionally substituted with one or more members selected from $R_{1a}$, $R_{1b}$, $R_{1c}$, $R_{1d}$ and $R_{1e}$;

$R_{1a}$, $R_{1b}$, $R_{1d}$ and $R_{1e}$ are each independently selected from the group consisting of hydrogen, alkyl, alkenyl, alkenyl, cycloalkyl, halo, —CN, —$OCF_3$, —$OR_{10}$, —OH, —C(=O)$NR_9R_9$, —$NR_9R_9$, —$S(O)_2NR_9R_9$, —$NR_9S(O)_2CF_3$, —C(=O)$R_{10}$, —$NR_9C(=O)H$, —$NR_9C(=O)R_{10}$, —OC(=O)$R_{10}$, —OC(=O)$NR_9R_9$, —S(=O)$R_{10}$, —$S(O)_2R_{10}$, —$NR_9C(=O)OR_8$ and —$NR_9S(O_2)R_8$, wherein the alkyl, alkenyl, alkynyl and cycloalkyl may each be optionally substituted with one or more $R_6$'s;

$R_{1c}$ is a 5-6 membered monocyclic heteroaryl which may be optionally substituted with one or more $R_6$'s;

$R_2$ is heteroaryl or C(=O)$OR_5$, wherein the heteroaryl may be optionally substituted with one or more $R_6$'s;

$R_5$ is alkyl, alkenyl, aryl, cycloalkyl, heteroaryl or heterocyclyl, each of which may be optionally substituted with one or more $R_6$'s;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —C(=O)$OR_{10}$, —$OCF_3$, —$OR_{10}$, —OH, —SH, —$SR_{10}$, —C(=O)$NR_9R_9$, —$NR_9R_9$, —$S(O)_2NR_9R_9$, —$NR_9S(O)_2CF_3$, —C(=O)$R_{10}$, —$NR_9C(=O)H$, —$NR_9C(=O)R_{10}$, —OC(=O)$R_{10}$, —S(=O)$R_{10}$, —$S(O)_2R_{10}$, =O, —$NR_9C(=O)OR_8$ and —$NR_9S(O_2)R_8$, wherein the alkyl, alkenyl, alkyl, aryl, cycloalkyl, cycloalkylalkyl, heteroaryl, heteroarylalkyl, heterocyclyl and heterocyclylalkyl may each be optionally substituted with 0-5 $R_{9a}$;

$R_8$, at each occurrence, is independently selected from the group consisting of alkyl and cycloalkyl, each of which may be optionally substituted with one or more $R_{8a}$'s;

$R_{8a}$, at each occurrence, is independently selected from alkyl, haloalkyl, aryl, alkenyl, alkynyl, cycloalkyl, halo, —$NH_2$, —CN, —C(=O)OH, —C(=O)$OR_{14}$, —$OCF_3$, —$OR_{14}$, —OH, —C(=O)$NR_{14}R_{14}$, —$NR_{14}R_{14}$, —$S(O)_2NR_{14}R_{14}$, —$NR_{14}S(O)_2CF_3$, —C(=O)$R_{14}$, —$NR_{14}C(=O)H$, —$NR_{14}C(=O)R_{14}$, —OC(=O)$R_{14}$, —S(=O)$R_{14}$, —$S(O)_2R_{14}$, =O, —$NR_{14}C(=O)OR_{14}$ and —$NR_{14}S(O_2)R_{14}$;

$R_9$, at each occurrence, is independently selected from hydrogen, alkyl, cycloalkyl and aryl, wherein the alkyl, cycloalkyl and aryl may each be optionally substituted with 0-5 $R_{9a}$;

$R_{9a}$, at each occurrence, is independently selected from alkyl, haloalkyl, aryl, alkenyl, alkynyl, cycloalkyl, halo, —$NH_2$, —CN, —C(=O)OH, —C(=O)$OR_{14}$, —$OCF_3$, —$OR_{14}$, —OH, —C(=O)$NR_{14}R_{14}$, —$NR_{14}R_{14}$, —$S(O)_2NR_{14}R_{14}$, —$NR_{14}S(O)_2CF_3$, —C(=O)$R_{14}$, —$NR_{14}C(=O)H$, —$NR_{14}C(=O)R_{14}$, —OC(=O)$R_{14}$, —S(=O)$R_{14}$, —$S(O)_2R_{14}$, —$NR_{14}C(=O)OR_8$, —$NR_{14}S(O_2)R_8$ and =O;

$R_{10}$, at each occurrence, is independently selected from alkyl, cycloalkyl and aryl, which may each be optionally substituted with 0-3 $R_{10a}$;

$R_{10a}$, at each occurrence, is independently selected from alkyl, haloalkyl, aryl, alkenyl, alkynyl, halo, —$NH_2$, —CN, —C(=O)$OR_{14}$, —$OCF_3$, —$OR_{14}$, —OH, —C(=O)$NR_{14}R_{14}$, —$NR_{14}R_{14}$, —$S(O)_2NR_{14}R_{14}$, —$NR_{14}S(O)_2CF_3$, —C(=O)$R_{14}$, —$NR_{14}C(=O)H$, —$NR_{14}C(=O)R_{14}$, —OC(=O)$R_{14}$, —S(=O)$R_{14}$, —$S(O)_2R_{14}$, —$NR_{14}C(=O)OR_8$ and —$NR_{14}S(O_2)R_8$;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, halo and —CN.

In a thirty-ninth embodiment, a method of modulating the activity of the GPR119 G protein-coupled receptor wherein for the compound of Formula IA:

ring A is optionally substituted with one or more R's shown as $R_{20}$ and $R_{21}$;

G is N;
Q is C;
X is CH;

Y is O;
$n_1$ is 1;
$n_2$ is 1;
$R_1$ is

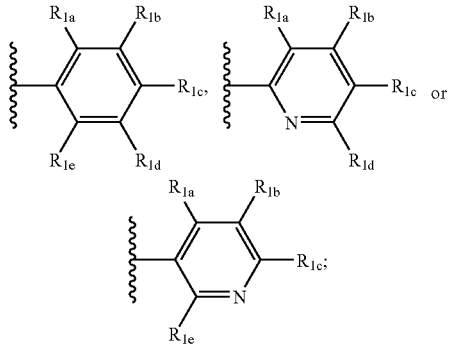

$R_{1a}$, $R_{1b}$, $R_{1d}$ and $R_{1e}$ are each independently selected from the group consisting of hydrogen, alkyl, alkenyl, alkynyl, cycloalkyl, halo, —CN, —OCF$_3$, —OR$_{10}$, —OH, —C(=O)NR$_9$R$_9$, —NR$_9$R$_9$, —S(O)$_2$NR$_9$R$_9$, —NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —S(=O)R$_{10}$, —S(O)$_2$R$_{10}$, —NR$_9$C(=O)OR$_8$ and —NR$_9$S(O$_2$)R$_8$, wherein the alkyl, alkenyl, alkynyl and cycloalkyl may each be optionally substituted with one or more R$_6$'s;

$R_{1c}$ is a 5-6 membered monocyclic heteroaryl which may be optionally substituted with one or more R$_6$'s;

$R_2$ is heteroaryl or —C(O)OR$_5$, wherein the heteroaryl may be optionally substituted with one or more R$_6$'s;

$R_5$ is alkyl, alkenyl, aryl, cycloalkyl, heteroaryl or heterocyclyl, each of which may be optionally substituted with one or more R$_6$'s;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)R$_{10}$, —NR$_9$C(=O)H, —NR$_9$C(=O)R$_{10}$, —OC(=O)R$_{10}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R$_{9a}$;

$R_8$, at each occurrence, is independently selected from the group consisting of alkyl and cycloalkyl, each of which may be optionally substituted with one or more R$_{8a}$'s;

$R_{8a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, =O, —NR$_{14}$C(=O)OR$_{14}$ and —NR$_{14}$S(=O)R$_{14}$;

$R_9$, at each occurrence, is independently selected from hydrogen, alkyl, cycloalkyl and aryl, wherein the alkyl, cycloalkyl and aryl may each be optionally substituted with 0-5 R$_{9a}$;

$R_{9a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$ and =O;

$R_{10}$, at each occurrence, is independently selected from alkyl, cycloalkyl and aryl, which may each be optionally substituted with 0-3 R$_{10a}$;

$R_{10a}$, at each occurrence, is independently selected from alkyl, haloalkyl, aryl, alkenyl, alkynyl, halo, —NH$_2$, —CN, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$ and —NR$_{14}$S(O$_2$)R$_8$;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, halo and —CN.

In a fortieth embodiment, a method of modulating the activity of the GPR119 G protein-coupled receptor wherein for the compound of Formula I:

ring A is optionally substituted with one or more R's shown as $R_{20}$ and $R_{21}$;

G is N;
Q is C;
X is CH;
Y is O;
$n_1$ is 1;
$n_2$ is 1;
$n_3$ is 2;
$R_1$ is

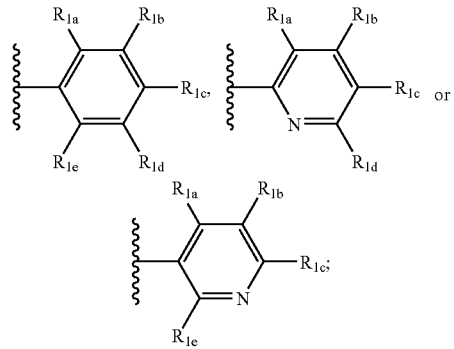

$R_{1a}$, $R_{1b}$, $R_{1d}$ and $R_{1e}$ are each independently selected from the group consisting of hydrogen, alkyl, alkenyl, alkynyl, cycloalkyl, halo, —CN, —OCF$_3$, —OR$_{10}$, —OH, —C(=O)NR$_9$R$_9$, —NR$_9$R$_9$, —S(O)$_2$NR$_9$R$_9$, —NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —S(=O)R$_{10}$, —S(O)$_2$R$_{10}$, —NR$_9$C(=O)OR$_8$ and —NR$_9$S(O$_2$)R$_8$, wherein the alkyl, alkenyl, alkynyl and cycloalkyl may each be optionally substituted with one or more R$_6$'s;

$R_{1c}$ is a 5-6 membered monocyclic heteroaryl which may be optionally substituted with one or more R$_6$'s;

$R_2$ is heteroaryl or —C(O)OR$_5$, wherein the heteroaryl may be optionally substituted with one or more R$_6$'s;

$R_5$ is alkyl, alkenyl, aryl, cycloalkyl, heteroaryl or heterocyclyl, each of which may be optionally substituted with one or more R$_6$'s;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclyl alkyl, halo, —CN, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)R$_{10}$, —NR$_9$C(=O)H, —NR$_9$C(=O)R$_{10}$, —OC(=O)R$_{10}$, —S(=O)R$_{10}$, —S(O)$_2$R$_{10}$, =O, —NR$_9$C(=O)OR$_8$ and —NR$_9$S(O)$_2$R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R$_{9a}$;

R$_8$, at each occurrence, is independently selected from the group consisting of alkyl and cycloalkyl, each of which may be optionally substituted with one or more R$_{8a}$'s;

R$_{8a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, =O, —NR$_{14}$C(=O)OR$_{14}$ and NR$_{14}$S(O)$_2$R$_{14}$;

R$_9$, at each occurrence, is independently selected from hydrogen, alkyl, cycloalkyl and aryl, wherein the alkyl, cycloalkyl and aryl may each be optionally substituted with 0-5 R$_{9a}$;

R$_{9a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$ and —NR$_{14}$S(O)$_2$R$_8$, =O;

R$_{10}$, at each occurrence, is independently selected from alkyl, cycloalkyl and aryl, which may each be optionally substituted with 0-3 R$_{10a}$;

R$_{10a}$, at each occurrence, is independently selected from alkyl, haloalkyl, aryl, alkenyl, alkynyl, halo, —NH$_2$, —CN, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, and —NR$_{14}$S(O)$_2$R$_8$;

R$_{14}$, at each occurrence, is independently selected from hydrogen, alkyl, cycloalkyl and aryl;

R$_{20}$ is hydrogen; and

R$_{21}$ is selected from the group consisting of hydrogen, alkyl, haloalkyl, halo and —CN.

In a forty-first embodiment, a method of modulating the activity of the GPR119 G protein-coupled receptor wherein for the compound of Formula IA:

ring A is optionally substituted with one or more R's shown as R$_{20}$ and R$_{21}$;

G is N;
Q is C;
X is CH;
Y is O;
n$_1$ is 1;
n$_2$ is 1;
R$_1$ is

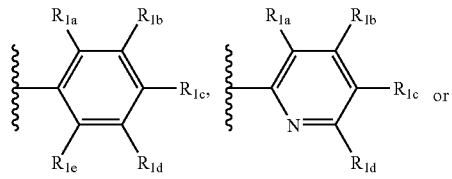

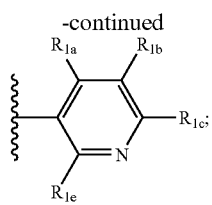

R$_{1a}$, R$_{1b}$, R$_{1d}$ and R$_{1e}$ are each independently selected from the group consisting of hydrogen, alkyl, alkenyl, alkynyl, cycloalkyl, halo, —CN, —OCF$_3$, —OR$_{10}$, —OH, —C(=O)NR$_9$R$_9$, —NR$_9$R$_9$, —S(O)$_2$NR$_9$R$_9$, —NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —S(=O)R$_{10}$, —S(O)$_2$R$_{10}$, —NR$_9$C(=O)OR$_8$ and —NR$_9$S(O)$_2$R$_8$, wherein the alkyl, alkenyl, alkynyl and cycloalkyl may each be optionally substituted with one or more R$_6$'s;

R$_{1c}$ is a 5-6 membered monocyclic heteroaryl which may be optionally substituted with one or more R$_6$'s;

R$_2$ is pyridinyl, pyrimidinyl or —C(=O)OR$_5$, wherein the pyridinyl and pyrimidinyl may each be optionally substituted with one or more R$_6$'s;

R$_5$ is alkyl, aryl or cycloalkyl, each of which may be optionally substituted with one or more R$_6$'s;

R$_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)R$_{10}$, —NR$_9$C(=O)H, —NR$_9$C(=O)R$_{10}$, —OC(=O)R$_{10}$, —S(=O)R$_{10}$, —S(O)$_2$R$_{10}$, =O, —NR$_9$C(=O)OR$_8$ and —NR$_9$S(O)$_2$R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 R$_{9a}$;

R$_8$, at each occurrence, is independently selected from the group consisting of alkyl and cycloalkyl, each of which may be optionally substituted with one or more R$_{8a}$'s;

R$_{8a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, =O, —NR$_{14}$C(=O)OR$_{14}$ and NR$_{14}$S(O)$_2$R$_{14}$;

R$_9$, at each occurrence, is independently selected from hydrogen, alkyl, cycloalkyl and aryl, wherein the alkyl, cycloalkyl and aryl may each be optionally substituted with 0-5 R$_{9a}$;

R$_{9a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(O)R$_{14}$, —S(O)$_2$R$_{14}$, —NR$_{14}$C(=O)OR$_8$, —NR$_{14}$S(O)$_2$R$_8$ and =O;

R$_{10}$, at each occurrence, is independently selected from alkyl, cycloalkyl and aryl, which may each be optionally substituted with 0-3 R$_{10a}$;

R$_{10a}$, at each occurrence, is independently selected from alkyl, haloalkyl, aryl, alkenyl, alkynyl, halo, —NH$_2$, —CN, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(O)R$_{14}$, —NR$_{14}$C(=O)H, —NR$_{14}$C(O)R$_{14}$, —OC(=O)R$_{14}$, —S(=O)R$_{14}$, —S(O)$_2$R$_{14}$, —NR$_{14}$C(=O)OR$_8$ and —NR$_{14}$S(O)$_2$R$_8$;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, halo and —CN.

In a forty-second embodiment, a method of modulating the activity of the GPR119 G protein-coupled receptor wherein for the compound of Formula I:

ring A is optionally substituted with one or more R's shown as $R_{20}$ and $R_{21}$;

G is N;
Q is C;
X is CH;
Y is O;
$n_1$ is 1;
$n_2$ is 1;
$n_3$ is 2;
$R_1$ is

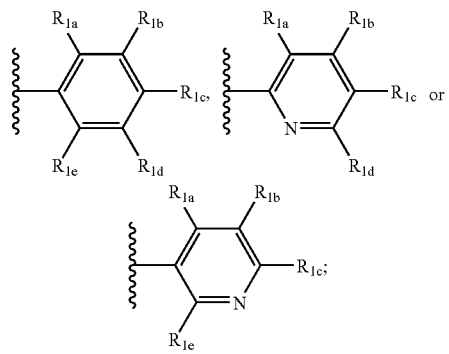

$R_{1a}$, $R_{1b}$, $R_{1d}$ and $R_{1e}$ are each independently selected from the group consisting of hydrogen, alkyl, alkenyl, alkynyl, cycloalkyl, halo, —CN, —OCF$_3$, —OR$_{10}$, —OH, —C(=O)NR$_9$R$_9$, —NR$_9$R$_9$, —S(O)$_2$NR$_9$R$_9$, —NR$_9$S(O)$_2$CF$_3$, —C(=O)R$_{10}$, —NR$_9$C(=O)H, —NR$_9$C(=O)R$_{10}$, —OC(=O)R$_{10}$, —OC(=O)NR$_9$R$_9$, —S(=O)R$_{10}$, —S(O)$_2$R$_{10}$, —NR$_9$C(=O)OR$_8$ and —NR$_9$S(O$_2$)R$_8$, wherein the alkyl, alkenyl, alkynyl and cycloalkyl may each be optionally substituted with one or more $R_6$'s;

$R_{1c}$ is a 5-6 membered monocyclic heteroaryl which may be optionally substituted with one or more $R_6$'s;

$R_2$ is pyridinyl, pyrimidinyl or —C(=O)OR$_5$, wherein the pyridinyl and pyrimidinyl may each be optionally substituted with one or more $R_6$'s;

$R_5$ is alkyl, aryl or cycloalkyl, each of which may be optionally substituted with one or more $R_6$'s;

$R_6$, at each occurrence, is independently selected from alkyl, haloalkyl, aryl, alkenyl, alkynyl, cycloalkyl, cycloalkylalkyl, heteroaryl, heteroarylalkyl, heterocyclyl, heterocyclylalkyl, halo, —CN, —C(=O)OR$_{10}$, —OCF$_3$, —OR$_{10}$, —OH, —SH, —SR$_{10}$, —C(=O)NR$_9$R$_9$, —NR$_9$R$_9$, —S(O)$_2$NR$_9$R$_9$, —NR$_9$S(O)$_2$CF$_3$, —C(=O)R$_{10}$, —NR$_9$C(=O)H, —NR$_9$C(=O)R$_{10}$, —OC(=O)R$_{10}$, —S(=O)R$_{10}$, —S(O)$_2$R$_{10}$, =O, —NR$_9$C(=O)OR$_8$ and —NR$_9$S(O$_2$)R$_8$, wherein the alkyl, alkenyl, alkynyl, aryl, cycloalkyl, cycloalkylalkyl, heteroaryl, heteroarylalkyl, heterocyclyl and heterocyclylalkyl may each be optionally substituted with 0-5 $R_{9a}$;

$R_8$, at each occurrence, is independently selected from the group consisting of alkyl and cycloalkyl, each of which may be optionally substituted with one or more $R_{8a}$'s;

$R_{8a}$, at each occurrence, is independently selected from alkyl, haloalkyl, aryl, alkenyl, alkynyl, cycloalkyl, halo, —NH$_2$—CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, =O, —NR$_{14}$C(=O)OR$_{14}$ and —NR$_{14}$S(O$_2$)R$_{14}$;

$R_9$, at each occurrence, is independently selected from hydrogen, alkyl, cycloalkyl and aryl, wherein the alkyl, cycloalkyl and aryl may each be optionally substituted with 0-5 $R_{9a}$;

$R_{9a}$, at each occurrence, is independently selected from alkyl, haloalkyl, aryl, alkenyl, alkynyl, cycloalkyl, halo, —NH$_2$, —CN, —C(=O)OH, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$, —NR$_{14}$S(O$_2$)R$_8$ and =O;

$R_{10}$, at each occurrence, is independently selected from alkyl, cycloalkyl and aryl, which may each be optionally substituted with 0-3 $R_{10a}$;

$R_{10a}$, at each occurrence, is independently selected from alkyl, haloalkyl, aryl, alkenyl, alkynyl, halo, —NH$_2$, —CN, —C(=O)OR$_{14}$, —OCF$_3$, —OR$_{14}$, —OH, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)R$_{14}$, —NR$_{14}$C(=O)H, —NR$_{14}$C(=O)R$_{14}$, —OC(=O)R$_{14}$, —S(=O)R$_{14}$, —S(O)$_2$R$_{14}$, —NR$_{14}$C(=O)OR$_8$ and —NR$_{14}$S(O$_2$)R$_8$;

$R_{14}$, at each occurrence, is independently selected from hydrogen, alkyl, cycloalkyl and aryl;

$R_{20}$ is hydrogen; and $R_{21}$ is selected from the group consisting of hydrogen, alkyl, haloalkyl, halo and —CN.

In a forty-third embodiment, compounds of Formula IA are provided wherein.

ring A is optionally substituted with one or more R's shown as $R_{20}$ and $R_{21}$;

G is N;
Q is C;
X is CH;
Y is O;
$n_1$ is 1;
$n_2$ is 1;
$R_1$ is

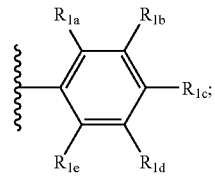

$R_{1a}$, $R_{1b}$, $R_{1d}$ and $R_{1e}$ are each independently selected from the group consisting of hydrogen, halo, CN and $C_{1-3}$ alkyl;

$R_{1c}$ is imidazolyl, oxazolyl or triazolyl;

$R_2$ is pyrimidinyl or —C(=O)OR$_5$, wherein the pyrimidinyl may be optionally substituted with $C_{1-3}$ alkyl;

$R_5$ is $C_{1-3}$ alkyl;

$R_{20}$ is hydrogen; and $R_{21}$ is hydrogen, halo or CN.

One particular method uses the compounds of Formula I.

Another particular method uses the compounds of Formula IA (noting that for Formula IA there is no $n_3$ in the formula).

For each of the embodiments used in the invention and described in this application, further and more particular values of the terms used in each of the embodiments may be selected from the following definitions; these values may be used individually or in any combination in any of the embodiments. It is noted that for any occurrences of "═O", these may be used with suitable accommodation in the bond structure at that site as will be appreciated by those skilled in the art.

The heteroaryl, heteroarylalkyl, heterocyclyl and heterocyclylalkyl used in each occurrence may each contain 1-4 heteroatoms selected from N, O and S.

$R_1$ may be selected from phenyl and a 6 membered monocyclic heteroaryl having 1 or 2 N's wherein:

a) phenyl and heteroaryl may each be substituted with 1-3 members selected from $R_{1a}$, $R_{1b}$, $R_{1c}$, $R_{1d}$ and $R_{1e}$;

b) $R_{1a}$, $R_{1b}$, $R_{1d}$ and $R_{1e}$ are each independently selected from the group consisting of hydrogen, $C_{1-3}$ alkyl, $C_{3-6}$ cycloalkyl, phenyl, halo, —CN, —$OR_{10}$, —OH, —SH, —$SR_{10}$, —C(═O)$NR_9R_9$, —$NR_9R_9$, —S(O)$_2NR_9R_9$, —$NR_9S(O)_2CF_3$, —C(═O)$R_{10}$, —$NR_9C$(═O)H, —$NR_9C$(═O)$R_{10}$, —S(═O)$R_{10}$, —S(O)$_2R_{10}$, —$NR_9C$(═O)$OR_8$ and —$NR_9S(O_2)R_8$, wherein the alkyl, cycloalkyl and phenyl may each be optionally substituted with one or more $R_6$'s; where $R_6$ may be selected from $C_{1-6}$ straight and branched chain alkyl; $C_{3-6}$ cycloalkyl; $C_{2-6}$ alkenyl; $C_{2-6}$ alkynyl; OH; phenyl; halo; $C_{1-6}$ haloalkyl; 5-6 membered heteroaryl having carbon atoms and 1-2 heteroatoms selected from O, S and N; 5-6 membered heterocycle having carbon atoms and 1-2 heteroatoms selected from O and N; $OCF_3$; $OR_{10}$ where $R_{10}$ is $C_{1-3}$ alkyl or $C_{3-6}$ cycloalkyl; and $SR_{10}$ where $R_{10}$ is $C_{1-3}$ alkyl or $C_{3-6}$ cycloalkyl; and further wherein the alkyl, alkenyl, alkynyl, phenyl, cycloalkyl, heteroaryl and heterocyclyl values of $R_6$ may each be optionally substituted with 0-3 $R_{9a}$, where $R_{9a}$ is selected from the group consisting of halo, $C_{1-3}$ haloalkyl, $C_{3-6}$ cycloalkyl, OH, $C_{1-3}$ alkoxy, CN and ═O; and c) $R_{1c}$ is a 5 membered monocyclic heteroaryl having 1-3 heteroatoms selected from O and N, which may be optionally substituted with one or more $R_6$'s; where $R_6$ may be selected from $C_{1-6}$ straight and branched chain alkyl; $C_{3-6}$ cycloalkyl; $C_{2-6}$ alkenyl; $C_{2-6}$ alkynyl; OH; phenyl; halo; $C_{1-6}$ haloalkyl; 5-6 membered heteroaryl having carbon atoms and 1-2 heteroatoms selected from O, S and N; 5-6 membered heterocycle having carbon atoms and 1-2 heteroatoms selected from O and N; $OCF_3$; $OR_{10}$ where $R_{10}$ is $C_{1-3}$ alkyl or $C_{3-6}$ cycloalkyl; and $SR_{10}$ where $R_{10}$ is $C_{1-3}$ alkyl or $C_{3-6}$ cycloalkyl; and further wherein the alkyl, alkenyl, alkynyl, phenyl, cycloalkyl, heteroaryl and heterocyclyl values of $R_6$ may each be optionally substituted with 0-3 $R_{9a}$, where $R_{9a}$ is selected from the group consisting of halo, $C_{1-3}$ haloalkyl, $C_{3-6}$ cycloalkyl, OH, $C_{1-3}$ alkoxy, CN and ═O.

$R_2$ may be selected from —C(═O)$OR_5$, a 5-6 membered monocyclic heteroaryl having 1-3 heteroatoms selected from O and N; and an 8-10 bicyclic heteroaryl having 1-3 heteroatoms selected from O and N, wherein:

i) the heteroaryls may be each substituted with 1 or 2 of $R_6$, where $R_6$ is selected from $C_{1-6}$ alkyl, $C_{1-3}$ haloalkyl, phenyl, $C_{3-6}$ cycloalkyl, halo, —CN, —$OCF_3$ and —$OC_{1-5}$alkyl, wherein the alkyl, phenyl, and cycloalkyl values for $R_6$ may each be optionally substituted with 0-2 $R_{9a}$ where $R_{9a}$ is selected from halo, $C_{1-3}$ haloalkyl, $C_{3-6}$ cycloalkyl, OH, $C_{1-3}$ alkoxy and CN; and ii) $R_5$ is selected from the group consisting of $C_{1-6}$ straight and branched chain alkyl, $C_{3-6}$ cycloalkyl and phenyl wherein the alkyl, phenyl, and cycloalkyl, may each be optionally substituted with 0-2 $R_6$ wherein 6 is as defined in i).

$R_5$ may be selected from the group consisting of $C_{1-6}$ straight and branched chain alkyl, $C_{3-6}$ cycloalkyl and phenyl wherein:

i) the alkyl, phenyl, and cycloalkyl, may each be optionally substituted with 0-2 $R_6$;

ii) $R_6$ is selected from $C_{1-6}$ straight and branched chain alkyl; $C_{3-6}$ cycloalkyl; $C_{2-6}$ alkenyl; $C_{2-6}$ alkynyl; OH; phenyl; halo; $C_{1-6}$ haloalkyl; 5-6 membered heteroaryl having carbon atoms and 1-2 heteroatoms selected from O, S and N; 5-6 membered heterocycle having carbon atoms and 1-2 heteroatoms selected from O and N; $OCF_3$; $OR_{10}$ where $R_{10}$ is $C_{1-3}$ alkyl or $C_{3-6}$ cycloalkyl; and $SR_{10}$ where $R_{10}$ is $C_{1-3}$ alkyl or $C_{3-6}$ cycloalkyl; and iii) the alkyl, alkenyl, alkynyl, phenyl, cycloalkyl, heteroaryl and heterocyclyl values of $R_6$ may each be optionally substituted with 0-3 $R_{9a}$, where $R_{9a}$ is selected from the group consisting of halo, $C_{1-3}$ haloalkyl, $C_{3-6}$ cycloalkyl, OH, $C_{1-3}$ alkoxy CN and ═O.

$R_6$ may be selected from $C_{1-6}$ straight and branched chain alkyl; $C_{3-6}$ cycloalkyl; $C_{2-6}$ alkenyl; $C_{2-6}$ alkynyl; OH; phenyl; halo; $C_{1-6}$ haloalkyl; 5-6 membered heteroaryl having carbon atoms and 1-2 heteroatoms selected from O, S and N; 5-6 membered heterocycle having carbon atoms and 1-2 heteroatoms selected from O and N; $OCF_3$; $OR_{10}$ where $R_{10}$ is $C_{1-3}$ alkyl or $C_{3-6}$ cycloalkyl; and $SR_{10}$ where $R_{10}$ is $C_{1-3}$ alkyl or $C_{3-6}$ cycloalkyl; and further wherein the alkyl, alkenyl, alkynyl, phenyl, cycloalkyl, heteroaryl and heterocyclyl values of $R_6$ may each be optionally substituted with 0-3 $R_{9a}$, where $R_{9a}$ is selected from the group consisting of halo, $C_{1-3}$ haloalkyl, $C_{3-6}$ cycloalkyl, OH, $C_{1-3}$ alkoxy, CN and ═O.

$R_8$ is selected from the group consisting of $C_{1-6}$ straight and branched chain alkyl and $C_{3-6}$ cycloalkyl each of which may be optionally substituted with one or more $R_{8a}$'s where $R_{8a}$ is selected from halo, $C_{1-3}$ haloalkyl, $C_{3-6}$ cycloalkyl, OH, $C_{1-3}$ alkoxy, CN and ═O.

$R_{8a}$ is selected from halo, $C_{1-3}$ haloalkyl, $C_{3-6}$ cycloalkyl, OH, $C_{1-3}$ alkoxy, CN and ═O.

$R_9$ is selected from H, $C_{1-3}$ straight and branched chain alkyl and $C_{3-6}$ cycloalkyl.

$R_{9a}$ is selected from halo, $C_{1-3}$ haloalkyl, $C_{3-6}$ cycloalkyl, OH, $C_{1-3}$ alkoxy, CN and ═O.

$R_{10}$ is selected from $C_{1-3}$ straight and branched chain alkyl and $C_{3-6}$ cycloalkyl.

$R_{10a}$ is selected from halo, $C_{1-3}$ haloalkyl $C_{3-6}$ cycloalkyl, OH, $C_{1-3}$ alkoxy, CN and ═O.

$R_{14}$ is H.

$R_{20}$ is H.

$R_{21}$ is selected from H, $C_{1-3}$ alkyl, $C_{3-6}$ cycloalkyl, halo and CN.

In a forty-fourth embodiment, compounds of the present invention are selected from the group of compounds exemplified in the Examples.

In a forty-fifth embodiment, the present invention relates to the use of pharmaceutical compositions comprised of a therapeutically effective amount of a compound of Formula I or IA, alone or, optionally, in combination with a pharmaceutically acceptable carrier and/or one or more other agent(s), for example, a glucagon-like peptide-1 receptor agonist or fragment thereof.

In a forty-sixth embodiment, the present invention relates to methods of modulating the activity of the GPR119 G protein-coupled receptor comprising administering to a mammalian patient, for example, a human patient, in need thereof a therapeutically effective amount of a compound of the present invention, alone, or optionally, in combination with another compound of the present invention and/or at least one other type of therapeutic agent.

In a forty-seventh embodiment, the present invention relates to a method for preventing, modulating, or treating the progression or onset of diseases or disorders associated with the activity of the GPR119 G protein-coupled receptor comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

Examples of diseases or disorders associated with the activity of the GPR119 G protein-coupled receptor that can be prevented, modulated, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis and its sequelae, abnormal heart function, myocardial ischemia, stroke, Metabolic Syndrome, hypertension, obesity, dislipidemia, dyslipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy and glaucoma.

In a forty-eighth embodiment, the present invention relates to a method for preventing, modulating, or treating the progression or onset of diabetes, hyperglycemia, obesity, dyslipidemia, hypertension and cognitive impairment comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

In a forty-ninth embodiment, the present invention relates to a method for preventing, modulating, or treating the progression or onset of diabetes, comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

In a fiftieth embodiment, the present invention relates to a method for preventing, modulating, or treating the progression or onset of hyperglycemia comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

In a fifty-first embodiment, the present invention relates to a method for preventing, modulating, or treating the progression or onset of obesity comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

In a fifty-second embodiment, the present invention relates to a method for preventing, modulating, or treating the progression or onset of dyslipidemia comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

In a fifty-third embodiment, the present invention relates to a method for preventing, modulating, or treating the progression or onset of hypertension comprising administering to a mammalian patient, for example, a human patient, in need of prevention, modulation, or treatment a therapeutically effective amount of a compound of the present invention, alone, or, optionally, in combination with another compound of the present invention and/or at least one other type of therapeutic agent.

In a fifty-fourth embodiment, the present invention relates to the use of a formulated product wherein the selected formulation is made by combining (a) a compound of Formula I and/or IA. The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

One enantiomer of a compound of Formula I and/or IA may display superior activity compared with the other. Thus, all of the stereochemistries are considered to be a part of the present invention. When required, separation of the racemic material can be achieved by high performance liquid chromatography (HPLC) using a chiral column or by a resolution using a resolving agent such as camphonic chloride as in Young, S. D. et al., *Antimicrobial Agents and Chemotherapy*, 2602-2605 (1995).

To the extent that compounds of Formula I and/or IA and salts thereof, may exist in their tautomeric form, all such tautomeric forms are contemplated herein as part of the present invention.

The term "substituted", as used herein, means that any one or more hydrogens on the designated atom or ring is replaced with a selection from the indicated group, provided that the designated atom's or ring atom's normal valency is not exceeded, and that the substitution results in a stable compound. When a substituent is keto (i.e., =O), then 2 hydrogens on the atom are replaced.

When any variable (e.g., $R_4$) occurs more than one time in any constituent or formula for a compound, its definition at each occurrence is independent of its definition at every other occurrence. Thus, for example, if a group is shown to be substituted with $(R_4)_m$ and m is 0-3, then said group may optionally be substituted with up to three $R_4$ groups and $R_4$ at each occurrence is selected independently from the definition of $R_4$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups may optionally include 1 to 4 substituents such as halo, for example F, Br, Cl, or I, or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, aryl alkylthio, aryloxyaryl, alkylamido, alkanoylamino, arylcarbonylamino, nitro, cyano, thiol, haloalkyl, trihaloalkyl, and/or alkylthio.

Unless otherwise indicated, the term "alkenyl" as used herein by itself or as part of another group refers to straight or branched chain radicals of 2 to 20 carbons, preferably 2 to 12 carbons, and more preferably 2 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio, and/or any of the alkyl substituents set out herein.

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl, and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

Unless otherwise indicated, the term "cycloalkyl" as employed herein alone or as part of another group includes saturated or partially unsaturated (containing 1 or 2 double bonds) cyclic hydrocarbon groups containing 1 to 10 rings, preferably 1 to 3 rings, including monocyclic alkyl, bicyclic alkyl (or bicycloalkyl) and tricyclic alkyl, containing a total of 3 to 20 carbons forming the ring, preferably 3 to 15 carbons, more preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl, cyclododecyl, cyclohexenyl,

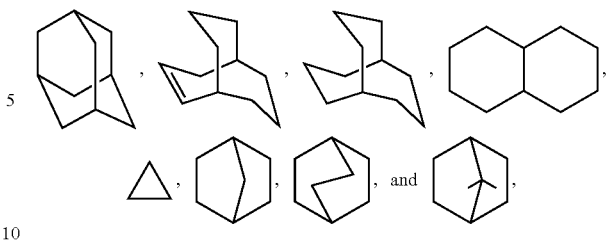

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

"Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example $-C_vF_w$ where v=1 to 3 and w=1 to (2v+1)).

Unless otherwise indicated, the term "aryl" as employed herein alone or as part of another group refers to monocyclic and bicyclic aromatic groups containing 6 to 10 carbons in the ring portion (such as phenyl or naphthyl, including 1-naphthyl and 2-naphthyl) and may optionally include 1 to 3 additional rings fused to a carbocyclic ring or a heterocyclic ring (such as aryl, cycloalkyl, heteroaryl, or cycloheteroalkyl rings for example

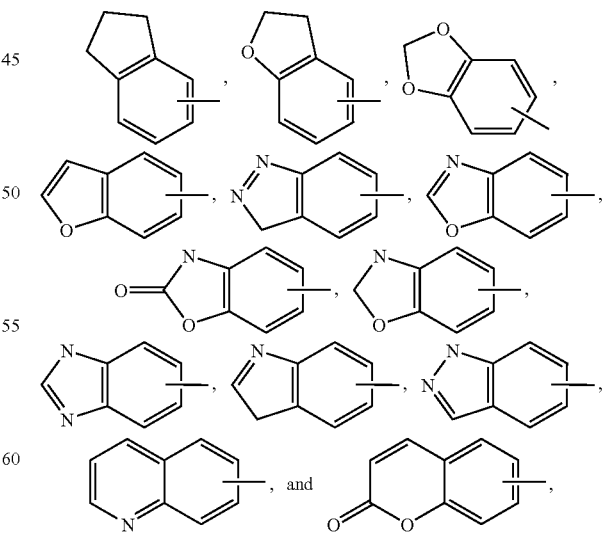

and may be optionally substituted through available carbon atoms with 1, 2, or 3 substituents, for example, hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl, or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino, or arylsulfonaminocarbonyl, and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl, or aryl groups linked to an oxygen atom.

Unless otherwise indicated, the term "amino" as employed herein alone or as part of another group refers to amino that may be substituted with one or two substituents, which may be the same or different, such as alkyl, aryl, arylalkyl, heteroaryl, heteroarylalkyl, cycloheteroalkyl, cycloheteroalkyl alkyl, cycloalkyl, cycloalkylalkyl, haloalkyl, hydroxyalkyl, alkoxyalkyl, or thioalkyl. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl, or hydroxy.

Unless otherwise indicated, the term "lower alkylthio", "alkylthio", "arylthio" or "aralkylthio" as employed herein alone or as part of another group includes any of the above alkyl, aralkyl, or aryl groups linked to a sulfur atom.

Unless otherwise indicated, the term "lower alkylamino", "alkylamino", "arylamino" or "arylalkylamino" as employed herein alone or as part of another group includes any of the above alkyl, aryl, or arylalkyl groups linked to a nitrogen atom.

As used herein, the term "heterocyclyl" or "heterocyclic system" is intended to mean a stable 4- to 14-membered monocyclic, bicyclic or tricyclic heterocyclic ring which is saturated or partially unsaturated and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom, which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another.

Examples of heterocycles include, but are not limited to, pyrrolidonyl, 4-piperidonyl, chromanyl, decahydroquinolinyl, dihydrofuro[2,3-b]tetrahydrofuran, indolinyl, isochromanyl, isoindolinyloctahydroisoquinolinyl, piperazinyl, piperidinyl, piperidonyl, 4-piperidonyl, tetrahydrofuranyl, tetrahydroisoquinolinyl, tetrahydroquinolinyl, morpholinyl, dihydrofuranyl, tetrahydrothiophenyl, pyranyl, dihydropyranyl, 1,4-dioxanyl and 1,3-dioxanyl. Also included are fused ring and spiro compounds containing, for example, the above heterocycles.

As used herein, the term "aromatic heterocyclic system" or "heteroaryl" is intended to mean a stable 5- to 7-membered monocyclic or bicyclic or 7- to 10-membered bicyclic heterocyclic aromatic ring which consists of carbon atoms and from 1 to 4 heteroatoms independently selected from the group consisting of N, O and S and is aromatic in nature Examples of heteroaryls are 1H-indazole, 2H,6H-1,5,2-dithiazinyl, indolyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, pteridinyl, purinyl, pyranyl, pyrazinyl, pyrazolidinyl, pyrazolinyl, pyrazolyl, pyrazolotriazinyl, pyridazinyl, pyridooxazole, pyridoimidazole, pyridothiazole, pyridinyl, pyridyl, pyrimidinyl, pyrrolidinyl, quinazolinyl, quinolinyl, 4H-quinolizinyl, quinoxalinyl, quinuclidinyl, carbolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, examples of heteroaryls are indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyrazolotriazinyl, pyridazinyl, pyridyl, pyridinyl, pyrimidinyl, pyrrolyl, quinazolinyl, quinolinyl, thiazolyl, thienyl, and tetrazolyl.

The term "heterocyclylalkyl" as used herein alone or as part of another group refers to heterocyclyl groups as defined above linked through a C atom or heteroatom to an alkyl chain.

The term "heteroarylalkyl" or "heteroarylalkenyl" as used herein alone or as part of another group refers to a heteroaryl group as defined above linked through a C atom or heteroatom to an alkyl chain, alkylene, or alkenylene as defined above.

The term "cyano" as used herein, refers to a —CN group.

The term "nitro" as used herein, refers to an —NO$_2$ group.

The term "hydroxy" as used herein, refers to an OH group.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., p. 1418 (1985), the disclosure of which is hereby incorporated by reference.

Any compound that can be converted in vivo to provide the bioactive agent (i.e., a compound of Formula I and/or IA) is a prodrug within the scope and spirit of the invention.

The term "prodrugs" as employed herein includes esters and carbonates formed by reacting one or more hydroxyls of compounds of Formula I and/or IA with alkyl, alkoxy, or aryl substituted acylating agents employing procedures known to those skilled in the art to generate acetates, pivalates, methylcarbonates, benzoates, and the like.

Various forms of prodrugs are well known in the art and are described in:

a) *The Practice of Medicinal Chemistry,* Camille G. Wermuth et al., Ch. 31 (Academic Press, 1996);

b) *Design of Prodrugs,* edited by H. Bundgaard, (Elsevier, 1985);

c) *A Textbook of Drug Design and Development,* P. Krogsgaard-Larson and H. Bundgaard, eds. Ch. 5, pp. 113-191 (Harwood Academic Publishers, 1991); and d) *Hydrolysis in Drug and Prodrug Metabolism,* Bernard Testa and Joachim M. Mayer, (Wiley-VCH, 2003).

Said references are incorporated herein by reference, particularly as to the description of prodrugs.

In addition, compounds of the Formula I and/or IA are, subsequent to their preparation, preferably isolated and purified to obtain a composition containing an amount by weight equal to or greater than 99% Formula I and/or IA compound ("substantially pure" compound I), which is then used or formulated as described herein. Such "substantially pure" compounds of the Formula I and/or IA are also contemplated herein as part of the present invention.

All stereoisomers of the compounds of the instant invention are contemplated, either in admixture or in pure or substantially pure form. The compounds of the present invention can have asymmetric centers at any of the carbon atoms including any one of the R substituents and/or exhibit polymorphism. Consequently, compounds of Formula I and/or IA can exist in enantiomeric, or diastereomeric forms, or in mixtures thereof. The processes for preparation can utilize racemates, enantiomers, or diastereomers as starting materials. When diastereomeric or enantiomeric products are prepared, they can be separated by conventional methods for example, chromatographic or fractional crystallization.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to modulate GPR119 or effective to treat or prevent various disorders.

As used herein, "treating" or "treatment" cover the treatment of a disease -state in a mammal, particularly in a human, and include: (a) preventing the disease-state from occurring in a mammal, in particular, when such mammal is predisposed to the disease-state but has not yet been diagnosed as having it; (b) modulating the disease-state, i.e., arresting it development; and/or (c) relieving the disease-state, i.e., causing regression of the disease state.

Selected Compounds

In addition to the methods described above, this invention also includes selected compounds as described in the Examples and their utility for the same purposes as recited for the method invention. These compounds are selected from compounds of Formula IA and enantiomers, diastereomers and pharmaceutically acceptable salts thereof, wherein:

ring A is optionally substituted with one or more R's shown as $R_{20}$ and $R_{21}$;

G is N;
Q is C;
X is CH;
Y is O;
$n_1$ is 1;
$n_2$ is 1;
$R_1$ is

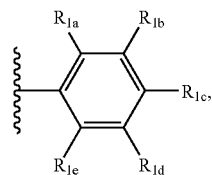

$R_{1a}$, $R_{1b}$, $R_{1d}$ and $R_{1e}$ are each independently selected from the group consisting of hydrogen, halo, CN and $C_{1-3}$ alkyl;

$R_{1c}$ is imidazolyl, oxazolyl or triazolyl;

$R_2$ is pyrimidinyl or —C(=O)OR$_5$, wherein the pyrimidinyl may be optionally substituted with $C_{1-3}$ alkyl;

$R_5$ is $C_{1-3}$ alkyl;

$R_{20}$ is hydrogen; and $R_{21}$ is hydrogen, halo or CN.

A more particular group of compounds are those described individually in the Examples, especially Examples 1-4.

Synthesis

The compounds used in the methods of the present invention and the selected compounds recited in the Examples can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The novel compounds of Formula I and/or IA may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the edict molecule must be compatible with the reagents and reactions proposed. Not all compounds of Formula I and/or IA falling into a given class may be compatible with some of the reaction conditions required in some of the methods described. Such restrictions to the substituents, which are compatible with the reaction conditions, will be readily apparent to one skilled in the art and alternate methods must be used.

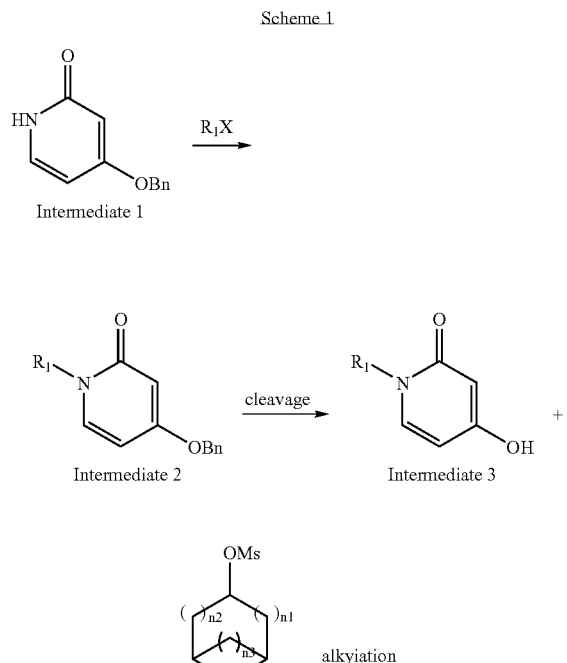

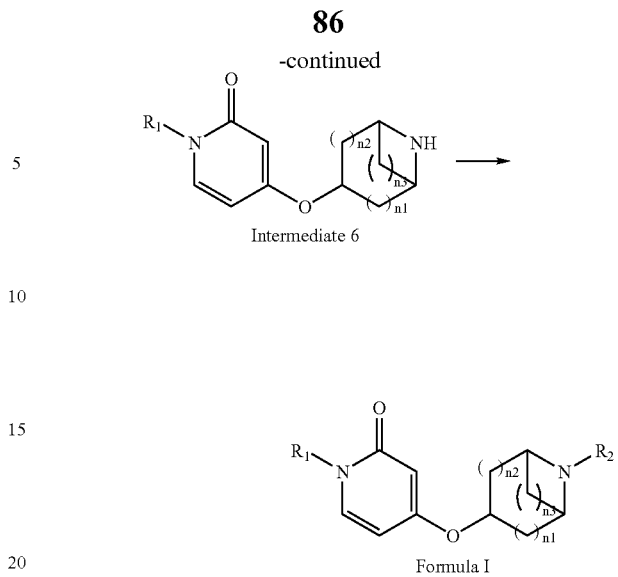

Compounds of Formula I and/or IA may be prepared by procedures depicted in Scheme 1. Intermediate 1, obtained from commercial sources, can be reacted with $R_1X$ (where $R_1$ other than H is as defined with respect to Formula I and/or IA and X is a halide) in the presence of a ligand such as 8-hydroxyquinoline, CuI (I) and a base such as $K_2CO_3$ in a suitable solvent such as DMF, DMSO etc. at an elevated temperature to yield intermediate 2. Cleavage of the benzyl group of intermediate 2 can be performed using the methods known in the art such as hydrogenolysis catalyzed by palladium. Intermediate 3 can then be alkylated with intermediate 4, which can be prepared by reaction of the corresponding alcohols with methanesulfonyl chloride, in the presence of a base such as $K_2CO_3$ at an elevated temperature. The above alcohols are commercially available or can be prepared by many methods well known to one skilled in the art (typical examples may be found in Sandler, S. et al., *Organic Functional Group Preparations*, Vol. I (Academic Press, Inc., 1983)). Removal of the protecting group of intermediate 5 can be carried out with appropriate reagents well known to those skilled in the art (for specific details see Greene et al., *Protecting Groups in Organic Synthesis* (John Wiley & Sons Inc., 1991)). The deprotected product can then be treated with $R_2X$ (where $R_2$ is defined as in Formula I and/or IA and X is a leaving group such as halide, mesylate, triflate, etc.), which are commercially available or can be prepared by many methods known in the art, at a number of conditions that are routine for those skilled in the art of organic synthesis to afford compounds of Formula I and/or IA. Alternatively the intermediate 6 can also be reacted with isocyates or isothiocyanates in the presence of a base such as $Et_3N$ to provide the compounds of Formula I and/or IA.

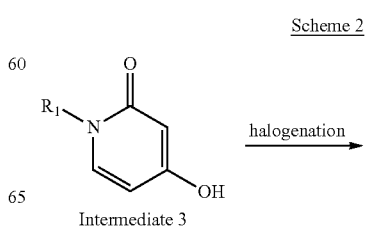

-continued

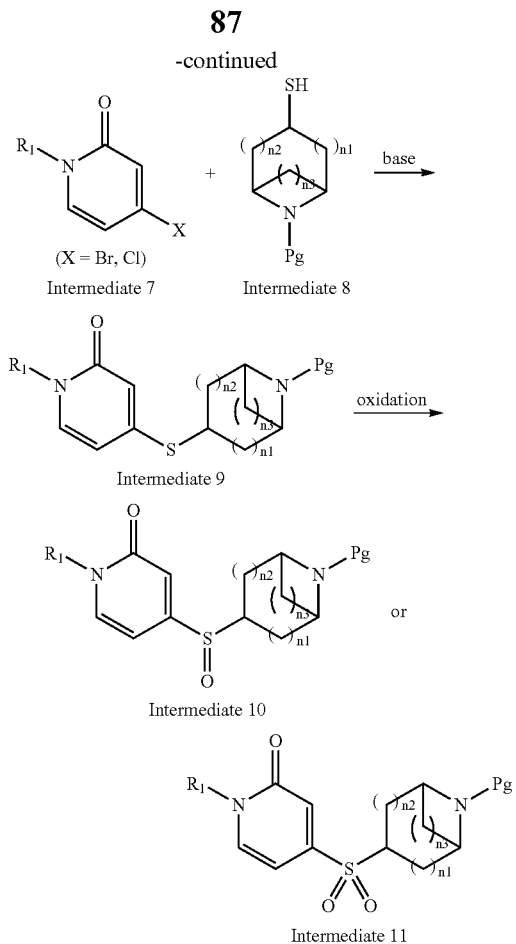

Compounds of Formula I and/or IA, wherein Y is defined as S, S(=O) or S (O)$_2$, may be prepared by procedures outlined in Scheme 2. Halogenation of intermediate 3 generated as described in Scheme I can be achieved with POBr$_3$, PBr$_3$ or POCl$_3$ using the conditions known to one skilled in the art. The halogenated pyridone can then be reacted with intermediate 8, which can be prepared according to the procedures described in U.S. Pat. No. 6,556,384 B1 (Owen, D et al.) incorporated by reference herein as to these preparations, in the presence of a base such as NaH to yield intermediate 9. Oxidation of intermediate 9 with an oxidant such as mCPBA in a suitable solvent such as CH$_2$Cl$_2$ affords intermediate 10 and intermediate 11. Intermediate 9, intermediate 10 or intermediate 11 can be carried forward to compounds of Formula I and/or IA following the procedures described above in Scheme 1 substituting intermediate 9, 10 or 11 for intermediate 5.

Scheme 3

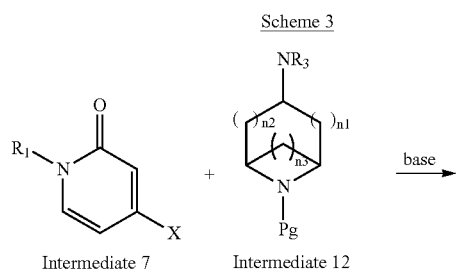

-continued

Intermediate 13

Compounds of Formula I and/or IA, wherein Y is defined as NR$_3$, may be prepared by procedures illustrated in Scheme 3. Intermediate 7 prepared as described in Scheme 11 can be reacted with intermediate 12, which are commercially available or can be prepared by the methods known to one skilled in the art, in the presence of a catalyst such as Pd (P(tBu)$_3$)$_2$ and a base such as NaOtBu in a suitable solvent such as toluene to yield intermediate 13. The products can then be further elaborated to compounds of Formula I and/or IA using the procedures described above in Scheme I substituting intermediate 13 for intermediate 5.

Alternatively, compounds of Formula I and/or IA, wherein Y is defined as N R$_3$, may also be prepared by the procedures similar to those provided in Scheme 3. Those invention compounds can be alternatively obtained by treatment of the compounds of Formula I and/or IA, wherein R$_3$=H, with a suitable electrophile R$_3$X (where X is a halide, mesylate, triflate, etc.) in the presence of a base such as K$_2$CO$_3$, CsCO$_3$, NaOtBu, etc.

Scheme 4

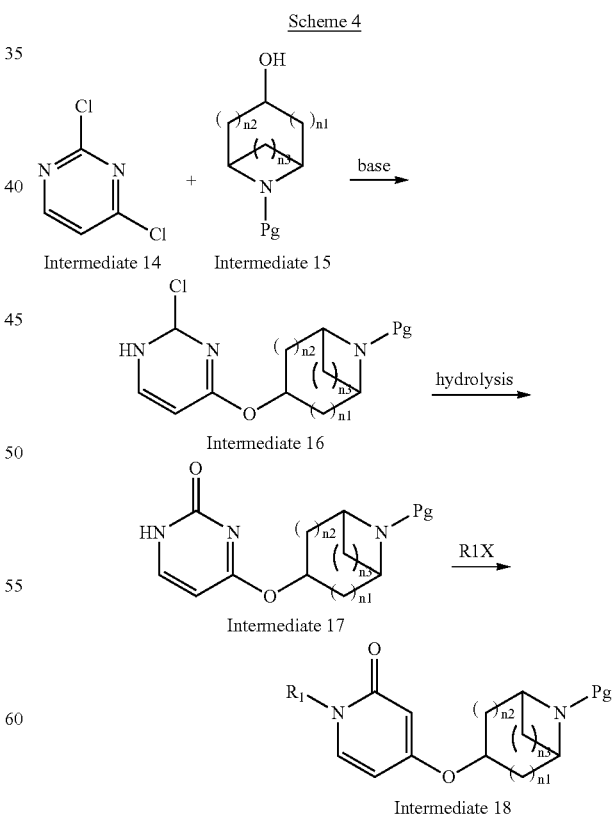

Alternatively, compounds of Formula I and/or IA can be synthesized by procedures outlined in Scheme 4. Intermediate 14, obtained from commercial sources, can be reacted with intermediate 15, which are commercially available or can be generated by many methods readily recognized by one skilled in the art (typical examples may be found in Sandler, S. et al., *Organic Functional Group Preparations*, Vol. I (Academic Press, Inc., 1983)), in the presence of a base such as NaH to yield intermediate 16. Hydrolysis of intermediate 16 can be achieved by treatment with DABCO in the presence of a base such as $K_2CO_3$ in dioxane/water at an elevated temperature. Intermediate 17 can then be reacted with $R_1X$ (where $R_1$ is defined with respect to Formula I and/or IA and X is a halide) in the presence of a ligand such as 8-hydroxyquinoline, CuI (I) and a base such as $K_2CO_3$ in a suitable solvent such as DMF, DMSO etc. at an elevated temperature to yield intermediate 18. The intermediate 18 can be carried forward to compounds of Formula I and/or IA following the procedures described above in Scheme 1 substituting intermediate 18 for intermediate 5.

Scheme 5

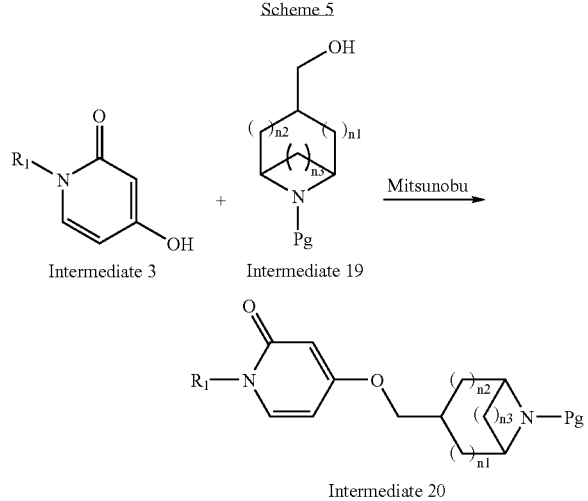

Compounds of Formula I and/or IA may be prepared by procedures illustrated in Scheme 5. Intermediate 3 generated as described in Scheme I can be reacted with intermediate 19, which are commercially available or can be made by many methods readily recognized by one skilled in the art (typical examples may be found in Sandler, S. et al., *Organic Functional Group Preparations*, Volume I, Academic Press, Inc., 1983), via Mitsunobo reaction to yield intermediate 20 which can be converted to Formula I and/or IA using the procedures described above in Scheme I substituting intermediate 20 for intermediate 5.

Scheme 6

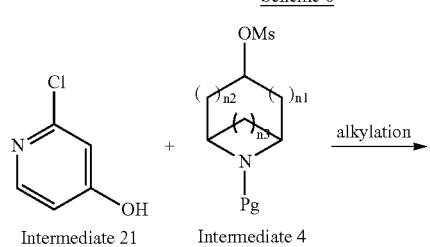

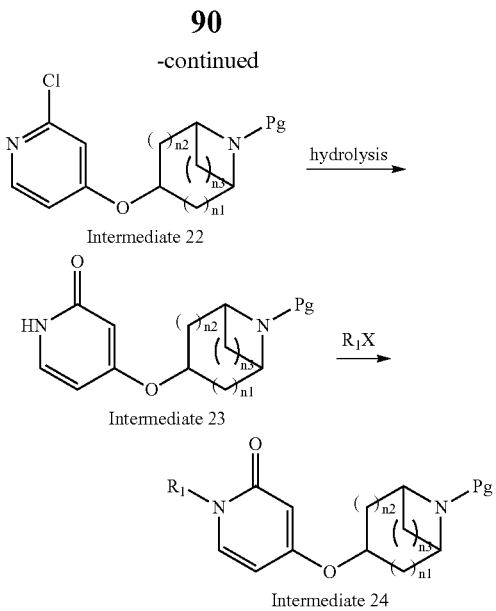

Alternatively, compounds of Formula I and/or IA may be synthesized as provided in Scheme 6. Intermediate 21, obtained from commercial sources, can be reacted with intermediate 4 prepared as described in Scheme I to give intermediate 22. Hydrolysis of intermediate 22 can be achieved by treatment with DABCO in the presence of a base such as $K_2CO_3$ in dioxane/water at an elevated temperature. Intermediate 23 can be treated with $R_1X$ (where $R_1$ is defined with respect to Formula I and/or IA and X is a halide) in the presence of a ligand such as 8-hydroxyquinoline, CuI (I) and a base such as $K_2CO_3$ in a suitable solvent such as DMF, DMSO etc at an elevated temperature to yield intermediate 24. The intermediate 24 can be carried forward to compounds of Formula I and/or IA following the procedures described above in Scheme I substituting intermediate 24 for intermediate 5.

Scheme 7

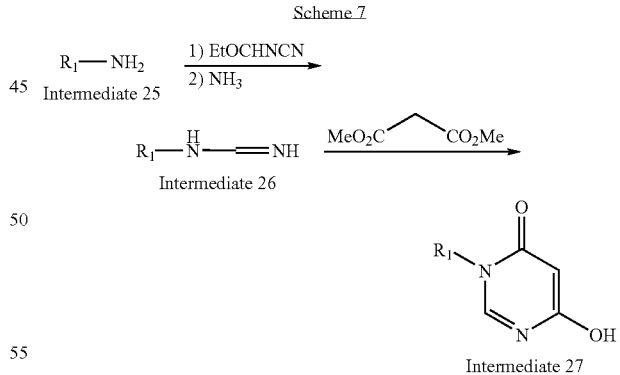

Compounds of Formula I and/or IA can also be prepared by procedures illustrated in Scheme 7. Intermediate 25 ($R_1$—$NH_2$, where $R_1$ is as defined in Formula I and/or IA), which are commercially available or can be made by methods recognized by one skilled in the art, can be converted to formamidine intermediate 26 in a two step procedure described by Donetti, A. et at. (*J. Med. Chem.*, 27:380 (1984)). Intermediate 26 can be reacted with dimethyl malonate to yield intermediate 27 using literature procedures (*J. Med. Chem.*, 45:3639 (2002)). The intermediate 27 can then be carried forward to compounds of Formula I and/or IA following the procedures described above in Scheme 1 substituting intermediate 28 for intermediate 3.

Abbreviations

The following abbreviations are employed in the Examples and elsewhere herein:

EtOAc = ethyl acetate
DMF = dimethylformamide
THF = tetrahydrofuran
$K_2CO_3$ = potassiumm carbonate
$Na_2CO_3$ = sodium carbonate
$MgSO_4$ = magnesium sulfate
$SiO_2$ = silicon dioxide
$CH_2Cl_2$ = methylene chloride
MeOH = methanol
HCl = hydrochloric acid
$Cs_2CO_3$ = cesium carbonate
KOH = potassium hydroxide
DME = 1,2-dimethoxyethane
TFA = trifluoroacetic acid
$Pd(dppf)Cl_2$ = [1,1'-bis(diphenylphosphino)ferrocene]dichloropalladium (II)
t-BuONa = sodium tert-butoxide
$Pd_2(dba)_3$ = tris(dibenzylideneacetone)dipalladium (0)
BINAP = rac-2,2'-bis(diphenylphosphino)-1,1'-binaphthyl
min = minute(s)
h or hr = hour(s)
mL or ml = milliliter
g = gram(s)
mg = milligram(s)
mmol = millimole(s)
LRMS = low resolution mass spectrometry
NMR = nuclear magnetic resonance

EXAMPLES FOR SELECTED COMPOUNDS OF THE INVENTION

The following Examples are offered as illustrative as a partial scope and as particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the Schemes and other methods disclosed herein or may be prepared using same.

Example 1

Preparation of 1-(4-(1H-1,2,4-triazol-1-yl)phenyl)-4-(1-(5-propylpyrimidin-2-yl)piperidin-4-yloxy)pyridin-2(1H)-one, hydrochloride salt

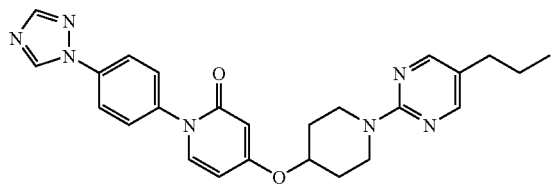

Step A. Preparation of 1-(5-propylpyrimidin-2-yl)piperidin-4-ol

To a stirring solution of piperidin-4-ol (2.33 g, 23.0 mmol, Aldrich) and potassium carbonate (6.36 g, 46.0 mmol, EMD) in DMF (15 mL) at room temperature was added 2-chloro-5-propylpyrimidine (4.33 g, 27.6 mmol, Wako). The reaction mixture was heated at 100° C. for 3 h then diluted with $H_2O$. The resulting mixture was extracted with EtOAc (2×). The organic layers were combined, dried over $Na_2SO_4$ and concentrated in vacuo to a brown oil. The oil was purified by flash chromatography ($SiO_2$, 0 to 100% EtOAc in $CH_2Cl_2$) to yield 5.01 g of desired product as a white solid. MS (ESI) 222 (M+H).

Step B. Preparation of 1-(5-propylpyrimidin-2-yl)piperidin-4-yl methanesulfonate To a stirring solution of 1-(5-propylpyrimidin-2-yl)piperidin-4-ol (9.2 g, 41.6 mmol), $Et_3N$ (12.85 mL, 91 mmol, Aldrich) in $CH_2Cl_2$ (80 mL) at 0° C. was added a solution of Methanesulfonyl chloride (3.54 mL, 45.7 mmol, Acros) in $CH_2Cl_2$ (20 mL) dropwise. The reaction mixture was stirred at room temperature for 1 h and washed with 1N HCl in $H_2O$, saturated $NaHCO_3$ in $H_2O$ and brine. The organic layer was dried over $Na_2SO_4$ and concentrated in vacuo to yield 11.7 g of the desired product as an off-white solid. MS (ESI) 300 (M+H).

Step C. Preparation of 4-(1-(5-propylpyrimidin-2-yl)piperidin-4-yloxy)pyridin-2(1H)-one A stirring suspension of 4-hydroxypyridin-2(1H)-one (5.23 g, 47.1 mmol, Aldrich), 1-(5-propylpyrimidin-2-ylpiperidin-4-yl methanesulfonate (11.7 g, 39.2 mmol), potassium carbonate (12.5 g, 90.0 mmol, EMD) and DMSO (48 mL) was heated at 100° C. for 3 hours and then cooled to room temperature. The resulting mixture was diluted with $H_2O$ and extracted with EtOAc (2×). The organic layers were combined and concentrated in vacuo to a brown solid. The solid was purified by flash chromatography ($SiO_2$, 100% EtOAc and then $SiO_2$, 10% MeOH in $CH_2Cl_2$) to yield 5.00 g of desired product as an off-white solid. MS (ESI) 315 (M+H).

Step D. Preparation of 1-(4-bromophenyl)-1H-1,2,4-triazole

A mixture of 1H-1,2,4-triazole (122 mg, 1.78 mmol, Aldrich), $K_3PO_4$ (751 mg, 3.53 mmol, Aldrich), Copper(I) iodide (33.7 mg, 0.177 mmol, Alfa-Aesar), 1-bromo-4-iodobenzene (500 mg, 1.78 mmol, Aldrich), (1S,2S)—N1,N2-dimethylcyclohexane-1,2-diamine (25 mg, 0.18 mmol, Strem) and DMSO (2 mL) was purged with Argon and then heated under microwave condition at 140° C. for 30 min and then at 160° C. for 30 min. The reaction mixture was diluted with $H_2O$ and extracted with EtOAc (2×). The organic layers were combined and concentrated in vacuo to a brown oil. The solid was purified by flash chromatography ($SiO_2$, 0-100% EtOAc in hexanes) to yield 195 mg of desired product as a white solid. MS (ESI) 224 (M+H).

Step E. Preparation of 1-(4-(1H-1,2,4-triazol-1-yl)phenyl)-4-(1-(5-propylpyrimidin-2-yl)piperidin-4-yloxy)pyridin-2(1H)-one A mixture of 1-(4-bromophenyl)-1H-1,2,4-triazole (45 mg, 0.20 mmol), 4-(1-(5-propylpyrimidin-2-yl)piperidin-4- yloxy)pyridin-2(1H)-one (58 mg, 0.18 mmol), quinolin-8-ol (11 mg, 0.074 mmol, Alfa Aesar), potassium carbonate (33 mg, 0.24 mmol), Copper(I) iodide (14 mg, 0.074 mmol, Alfa Aesar) in DMSO (2 mL) was heated under microwave condition at 160° C. for 30 min. The resulting mixture was diluted with H$_2$O and extracted with EtOAc (2×). The combined organic layers were concentrated in vacuo to a green oil. The oil was purified by flash chromatography (SiO$_2$, 0 to 100% EtOAc in CH$_2$Cl$_2$ and then SiO$_2$, 0 to 10% MeOH in CH$_2$Cl$_2$) to yield an off-white solid. The solid was dissolved in DCM and 1 eq of HCl (1N HCl in Et$_2$O) was added, the resulting mixture stirred for 5 min and then concentrated in vacuo to give 27 mg of desired product as an off-white solid. MS (ESI) 458 (M+H).

Step F. Example 1

To a stirring solution of 1-(4-(1H-1,2,4-triazol-1-yl)phenyl)-4-(1-(5-propylpyrimidin-2-yl)piperidin-4-yloxy)pyridin-2(1H)-one in CH$_2$Cl$_2$ was added 1 equivalent of HCl (1N HCl in Et$_2$O). This solution was stirred for 5 min and then concentrated in vacuo to give the desired product as an off-white solid. $^1$H NMR (400 MHz, CDCl$_3$) δ ppm 8.86 (br. s., 1 H), 8.44 (s, 2 H), 8.21 (br. s., 1 H), 7.88 (d, J=8.28 Hz, 2 H), 7.58 (d, J=8.53 Hz, 2 H), 7.35 (d, J=7.78 Hz, 1 H), 6.20-6.34 (m, 1 H), 6.15 (dd, J=7.53, 2.01 Hz, 1 H), 4.73-4.87 (m, 1 H), 4.25-4.40 (m, 2 H), 4.10-4.25 (m, 2 H), 2.56 (t, J=7.65 Hz, 2 H), 2.10-2.22 (m, 4 H), 1.61-1.72 (m, 2 H), 1.00 (t, J=7.40 Hz, 3 H). MS (ESI) 458 (M+H).

Example 2

Preparation of 1-(4-(1H-imidazol-1-yl)phenyl)-4-(1-(5-propylpyrimidin-2-yl)piperidin-4-yloxy)pyridin-2(1H)-one, hydrochloride salt

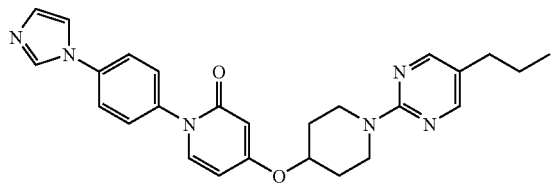

Example B was prepared according to procedures described in Example 1 substituting 1-(4-bromophenyl)-1H-imidazole (Oakwood) for 1-(4-bromophenyl)-1H-1,2,4-triazole in Step E except that the crude solid was purified by flash chromatography (SiO$_2$, 0 to 15% MeOH in CH$_2$Cl$_2$). The product was then converted to the hydrochloride salt by addition of 1 equivalent of HCl (1N HCl in Et$_2$O) to the compound stirring in CH$_2$Cl$_2$ for 5 min followed by concentration in vacuo to the desired product. $^1$H NMR (400 MHz, CDCl$_3$) δ ppm 9.76 (hr. s., 1 H), 8.40 (br. s., 2 H), 7.45-8.01 (m, 7 H), 6.45-6.59 (m, 1 H), 6.27-6.43 (m, 1 H), 4.87-5.18 (m, 1 H), 4.16-4.38 (m, 4 H), 2.45-2.60 (m, 2 H), 2.12-2.32 (m, 2 H), 1.94-2.11 (m, 2 H), 1.50-1.76 (m, 2 H), 0.96 (t, J=7.15 Hz, 3 H). MS (ESI) 457 (M+H).

Example 3

Preparation of 1-(4-(oxazol-2-yl)phenyl)-4-(1-(5-propylpyrimidin-2-yl)piperidin-4-yloxy)pyridin-2(1H)-one

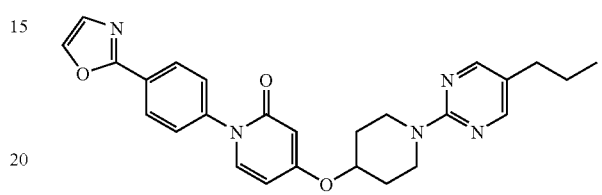

Example C was prepared according to procedures described in Example 1, Step A to E, substituting 2-(4-bromophenyl)oxazole (JW-Pharmlab) for 1-(4-bromophenyl)-1H-1,2,4-triazole in Step E. $^1$H NMR (400 MHz, CDCl$_3$) δ ppm 8.12-8.22 (m, 4 H), 7.75 (s, 1 H), 7.50 (d, J=8.53 Hz, 2 H), 7.28 (br. s., 1 H), 7.24-7.26 (m, 1 H), 5.98-6.08 (m, 2 H), 4.54-4.62 (m, 1 H), 4.16-4.26 (m, 2 H), 3.58-3.70 (m, 2 H), 2.42 (t, J=7.53 Hz, 2 H), 2.03-2.18 (m, 2 H), 1.78-1.94 (m, 2 H), 1.52-1.66 (m, 2 H), 0.95 (t, J=7.28 Hz, 3 H). MS (ESI) 458 (M+H).

Example 4

Preparation of isopropyl 4-(1-(4-(1H-1,2,4-triazol-1-yl)phenyl)-2-oxo-1,2-dihydropyridin-4-yloxy)piperidine-1-carboxylate

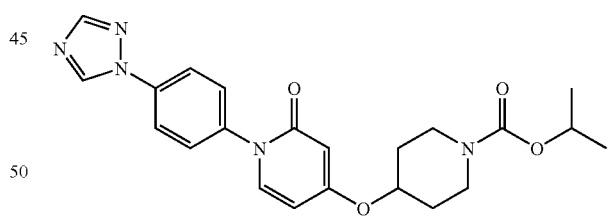

Step A. Preparation of isopropyl 4-hydroxypiperidine-1-carboxylate

To a stirring solution of piperidin-4-ol (5.22 g, 51.6 mmol, Aldrich), Et$_3$N (13.2 mL, 95 mmol, Aldrich) in CH$_2$Cl$_2$ (50 mL) at 0° C. was added a solution of Isopropyl chloroformate (1 Molar in Toluene, 43.0 mL, 43.0 mmol, Aldrich) dropwise. The reaction mixture was stirred at room temperature for 1 h and washed with 1N HCl in H$_2$O. The H$_2$O layer was extracted with DCM (2×). The organic layers were combined and concentrated in vacuo to yield 5.71 g of the desired product as a light brown oil. MS (ESI) 188 (M+H).

Step B. Example 4

Example 4 was prepared according to procedures described in Example 1, Step A to E substituting isopropyl 4-hydroxypiperidine-1-carboxylate for 1-(5-propylpyrimidin-2-yl)piperidin-4-ol in Step B. $^1$H NMR (400 MHz, CDCl$_3$) δ ppm 8.62 (br. s., 1 H), 8.16 (s, 1 H), 7.79-7.88 (m, 2 H), 7.52-7.61 (m, 2 H), 7.26-7.28 (m, 1 H), 6.05 (dd, J=7.53, 2.76 Hz, 1 H), 6.00 (d, J=2.76 Hz, 1 H), 4.90-5.01 (m, 1 H), 448-4.56 (m, 1 H), 3.72-3.84 (m, 2 H), 3.34-3.47 (m, 2 H), 1.91-2.06 (m, 2 H), 1.76-1.91 (m, 2 H), 1.28 (d, J=6.27 Hz, 6 H). MS (ESI) 424 (M+H).

Additional Examples

The following Examples are selected compounds that are believed to be particularly active for modulating the GPR119 receptor and are a subset of the compounds which may be prepared using the Schemes and methods described above, together with synthetic methods known in the art of synthetic organic chemistry, or variations thereon as appreciated by those skilled in the art.

The compounds may be selected from any combinations of $R_{1a}$, $R_{1b}$, $R_{1c}$, $R_{1d}$, $R_{1e}$, $R_{21}$ and $R_2$ shown in Table 1, Table 2 and Table 3 to the extent that such compounds can be made stable as will be appreciated by those skilled in the art.

TABLE 1

| $R_{1a}$, $R_{1b}$, $R_{1d}$ or $R_{1e}$ | $R_{1c}$ | $R_{21}$ | $R_2$ |
|---|---|---|---|
| —H, —CH$_3$, —C$_2$H$_5$, —Cl, —F, —CN, —OCH$_3$, —OCF$_3$, or 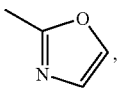 | 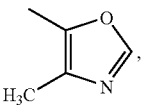, 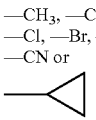, 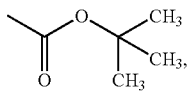, 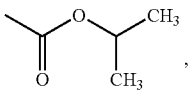, 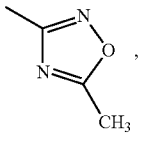, 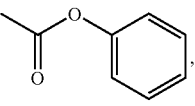, 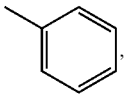, 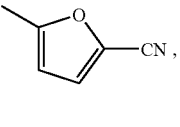, 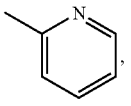, 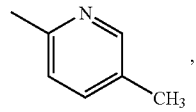 | —CH$_3$, —C$_2$H$_5$, —Cl, —Br, —F, —CN or 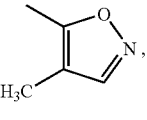 | 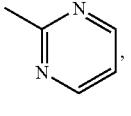, 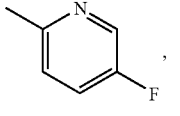, 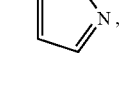, 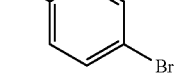, 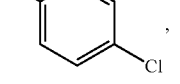, 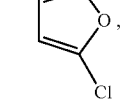, 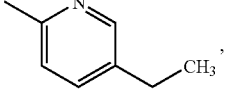 |

TABLE 1-continued
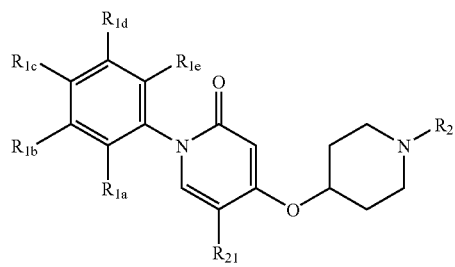
| $R_{1a}$, $R_{1b}$, $R_{1d}$ or $R_{1e}$ | $R_{1c}$ | $R_{21}$ | $R_2$ |
|---|---|---|---|
| | 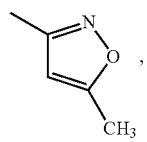 | 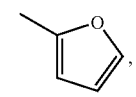 | 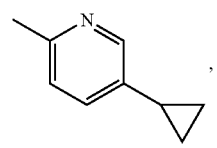 |
| | 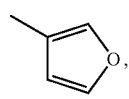 | 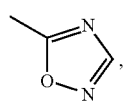 | 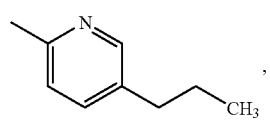 |
| | 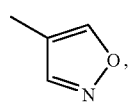 | 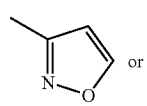 or | 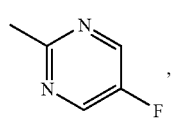 |
| | 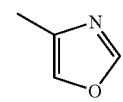 | | 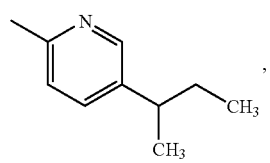 |
| | | | 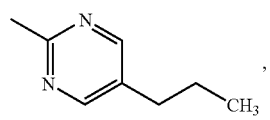 |
| | | | 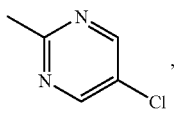 , 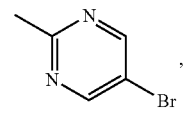 |
| | | | 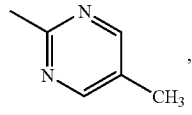 |
| | | | 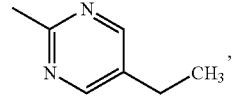 |
| | | | 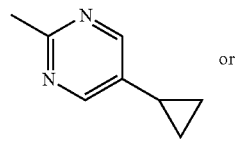 or |

TABLE 1-continued

[Structure: 1-(substituted phenyl)-4-(piperidin-4-yloxy)pyridin-2(1H)-one with R$_{1a}$, R$_{1b}$, R$_{1c}$, R$_{1d}$, R$_{1e}$ on phenyl, R$_{21}$ on pyridinone, and R$_2$ on piperidine nitrogen]

| R$_{1a}$, R$_{1b}$, R$_{1d}$ or R$_{1e}$ | R$_{1c}$ | R$_{21}$ | R$_2$ |
|---|---|---|---|
|  |  |  | 2-methyl-5-(sec-butyl)pyrimidin-5-yl |

TABLE 2

[Structure: same core as Table 1]

| R$_{1a}$, R$_{1b}$, R$_{1d}$ or R$_{1e}$ | R$_{1c}$ | R$_{21}$ | R$_2$ | |
|---|---|---|---|---|
| —H, —CH$_3$, —C$_2$H$_5$, —Cl, —F, —CN, —OCH$_3$, —OCF$_3$, or cyclopropyl | 1-methyl-1,2,4-triazol-3-yl | 1-methyl-imidazol-2-yl | —CH$_3$, —C$_2$H$_5$, —Cl, —Br, —F, —CN or cyclopropyl | —C(O)OC(CH$_3$)$_3$ | —C(O)OCH(CH$_3$)$_2$ |
|  | 1,2-dimethylpyrrol-5-yl | 1-methylpyrazol-5-yl |  | —C(O)OPh | phenyl (tolyl) |
|  | 1,3,4-trimethylpyrazol-5-yl | 1-methyl-1,2,3-triazol-5-yl |  | pyridin-2-yl | 5-methylpyridin-2-yl |
|  | 1-methylpyrrol-2-yl | 1,2,5-trimethylpyrrol-3-yl |  | 2-methylpyrimidin-5-yl | 5-fluoropyridin-2-yl |

TABLE 2-continued
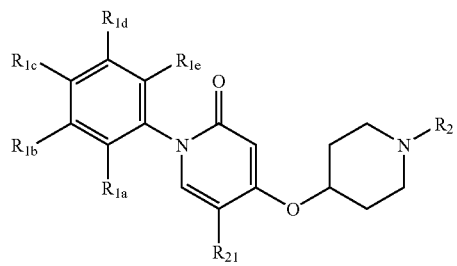
| $R_{1a}$, $R_{1b}$, $R_{1d}$ or $R_{1e}$ | $R_{1c}$ | $R_{21}$ | $R_2$ |
|---|---|---|---|

TABLE 2-continued
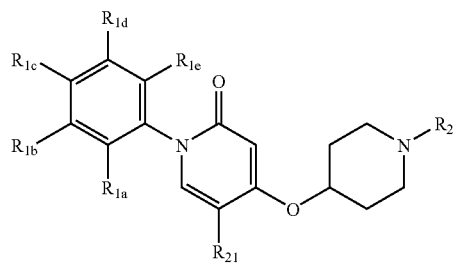
| $R_{1a}$, $R_{1b}$, $R_{1d}$ or $R_{1e}$ | $R_{1c}$ | $R_{21}$ | $R_2$ |
|---|---|---|---|
| | | | 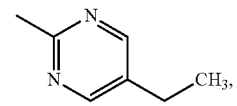 |
| | | | 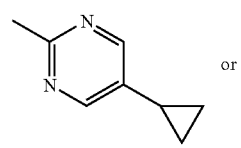 |
| | | | 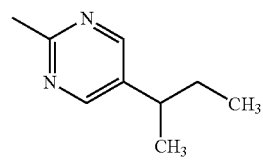 |
TABLE 3
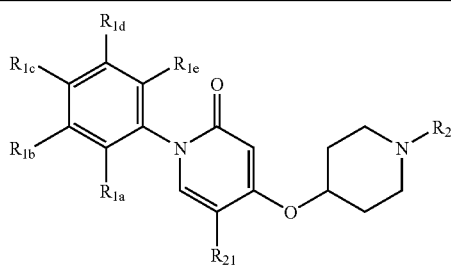
| $R_{1a}$, $R_{1b}$, $R_{1d}$ or $R_{1e}$ | $R_{1c}$ | $R_{21}$ | $R_2$ | |
|---|---|---|---|---|
| —H, —CH$_3$, —C$_2$H$_5$, —Cl, —F, —CN, —OCH$_3$, —OCF$_3$, or 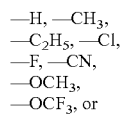 | 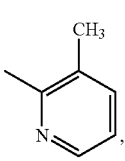 <br /> 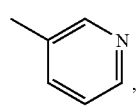 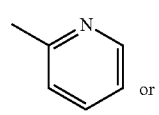 | 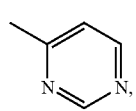 <br /> 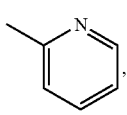 | 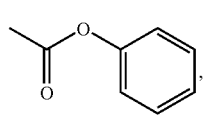 <br /> 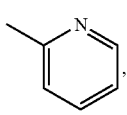 | 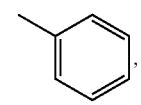 <br /> 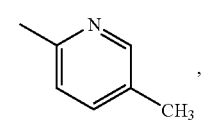 |

TABLE 3-continued
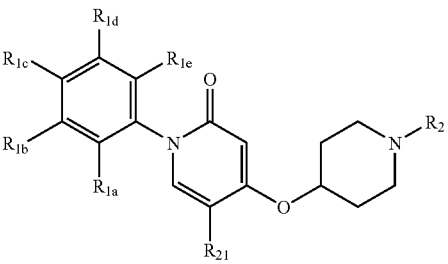
| $R_{1a}, R_{1b},$ $R_{1d}$ or $R_{1e}$ | $R_{1c}$ | $R_{21}$ | $R_2$ |
|---|---|---|---|
| | 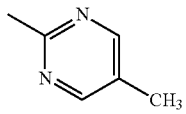 | 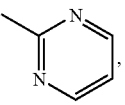 | 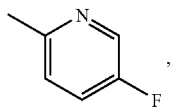, |
| | | 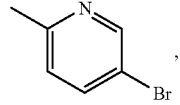, | 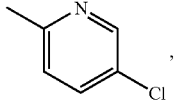, |
| | | 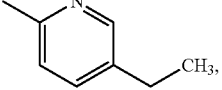, | |
| | | 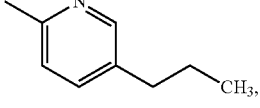, | |
| | | 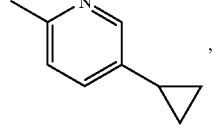, | |
| | | 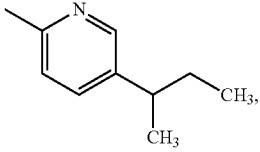, | |
| | | 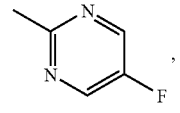, | 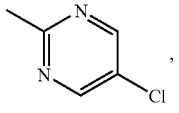, |
| | | 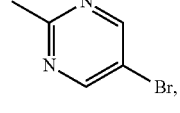, | |
| | | 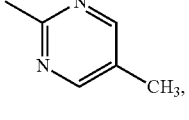, | |

TABLE 3-continued

[Structure: pyridinone core with substituted phenyl (R1a-R1e) bearing N-linkage, R21 on pyridinone, and O-linked piperidine with N-R2]

| R1a, R1b, R1d or R1e | R1c | R21 | R2 |
|---|---|---|---|
| | | | 2-methylpyrimidin-5-yl-CH2CH3 (ethyl) |
| | | | 2-methylpyrimidin-5-yl-CH3 (methyl) |
| | | | 2-methylpyrimidin-5-yl-cyclopropyl, or |
| | | | 2-methylpyrimidin-5-yl-CH(CH3)CH3 (isopropyl) |

Assay(s) for GPR119 G Protein-Coupled Receptor Activity

The in vitro modulation of recombinant human GPR119 was determined as follows.

HIT-T15 cAMP Assay

A HIT-T15 hamster insulinoma cell line was purchased from ATCC and grown in the medium recommended by ATCC (i.e., Growth Medium: F12K Medium (Invitrogen 21127-022; 10% D-horse Serum; and 2.5% FBS).

To conduct the cAMP assay, cells expressing a GPR119 receptor are plated on 96 well plates (e.g., BD Falcon: REF 353948, black side clear bottom, TC surface) at a density of about $4.5 \times 10^4$ cells per well in growth medium and incubated overnight. Following incubation, the growth medium is removed from the wells followed by a single rinse with the assay buffer from the Hit Hunter cAMP kit (100 μl/well). Following the rinse, 20 μl of assay buffer is added to each well followed by addition of 10 μl of a 3× concentration of compound working solution. The solution is then mixed well. The final concentration range of compound is from about $10^{-5}$ M to about $10^{-11}$ M. The reaction is incubated at 37° C., in a 5% $CO_2$ for 1 hour. Following incubation, the cAMP concentration is determined using the Hit Hunter cAMP kit according to the manufacturer's protocol.

Human Tet-inducible cAMP Assay

Cell lines expressing GPR119 are generated using the Flp-In-T-REx 293 tetracycline inducible gene expression system are cultured in culture medium comprising the following components: DMFM#11965, 10% FBS, 2 mM L-glutamine, 200 ug/ml Hygromycin B, and 15 ug/ml blasticidin.

For cAMP assays, cells are plated on 96 well plates (e.g., BD Falcon: REF 353948, black side, clear bottom, TC surface) at a density of about $4.5 \times 10^4$ cells per well in growth medium containing 1.0 ug/ml tetracycline (1.0 mg/ml stock). The cells are then incubated for 48 hours at 37° C.

Following the incubation, the growth medium is removed from the wells and the wells rinsed (once) with the assay buffer included in the Hit Hunter cAMP kit (100 μl/well). Following the wash, 20 μl of assay buffer is added to each well, followed by addition of 10 μl of a 3× concentration compound working solution. The solution is then mixed. The final concentration range of compound is from about $10^{-5}$ M to about $10^{-11}$ M. The reagents are then incubated at 37° C. at 5% $CO_2$ for 1 hour.

The manufacturer's protocol may be followed for cAMP determination. The Hit Hunter cAMP kit protocol is outlined for the HIT-T15 cAMP assays described above.

Compounds of the present invention were tested in the Human Tet-inducible cAMP assay described immediately above and the results shown in Table 4 below were obtained.

TABLE 4

| Example | hGPR119 EC$_{50}$ (nM) |
|---|---|
| 1 | 87 |
| 2 | 94 |
| 3 | 204 |
| 4 | 5192 |

Luciferase Assay

HEK 293 cells may be plated on poly-D-lysine treated 96-well BD black side/clear bottom plates at a density of about 3×10$^4$ cells/well in growth medium. The growth medium may comprise the following: D-MEM (Cat #12430) with high glucose and 10% fetal bovine serum.

Cells may be transfected with vectors comprising native or non-native GPR119 sequences using commercially available vectors (e.g., Stratagene) and transfection reagents. The standard manufacturer's protocols may be followed to transfect the cells. Following transfection, the transfection medium may be removed and assay medium added to the wells of the assay plates.

Once the assay plates are prepared, compound dilution plates may be made. To do so, make a first compound dilution plate using 10 mM of the compound of interest diluted to about 1 mM in DMSO. Then make 12 point half-log dilutions of the compounds (in DMSO) using an automated liquid handler. Next, make a second dilution plate by diluting the wells in the first plate ten fold (10×) using assay medium. Once the plates are complete, the highest dose is about 10 µM and the lowest dose is about 0.03 nM.

Once the dilution plates are complete, one can add about 10 µl of the 10× compound dilution to the assay plate containing the assay medium transiently transfected cells. Tap the plate to mix the reagents and incubate the plate overnight at 37° C., 95% O$_2$, and 5% CO$_2$ in an incubator.

Following incubation, a luciferase assay system may be used (e.g., Stead-Glo Luciferase Assay System from Promega) according to the manufacturer's instructions. Following completion of the reaction, immediately measure the readout of the assay using a top count luminometer.

Mouse Oral Glucose Tolerance Test 24 male C57BL/6J mice (8-10 weeks old, average weight 28 g) were randomized into 4 groups (1 mouse/cage) of 6 mice per group based on fed plasma glucose and body weight. Prior to initiating the study, mice were fasted overnight and the next morning they were weighed and placed in the experimental lab. After 30 min in the environment, the mice were bled via tail tip at −30 min and immediately given their first oral administration of vehicle (0.5% Methocel, 0.1% Tween 80 in water) or compound solutions (5 ml/kg). At time 0 the mice were bled and given 50% glucose (2 g/kg) to initiate the oral glucose tolerance test (oGTT). The mice were bled 30, 60 and 120 min after the glucose load. Blood samples were drawn into potassium EDTA, placed on ice during the study and subsequently centrifuged for 10 min at 3000 rpm at 4° C. Plasma samples were diluted 11-fold for glucose analysis in the Cobas Mira System (Roche Diagnostics). Area under the curve was calculated from the plasma glucose time course data using the trapezoid rule with fasting plasma glucose as the baseline (GraphPad Prism Software). The statistical significance of the changes in the glucose AUCs resulting from the different treatments was determined by one-way ANOVA followed by Dunnett's test using the vehicle group as the control (JMP software, release 5.1.2).

UTILITIES AND COMBINATIONS

A. Utilities

The methods and compounds of the present invention possess activity as agonists of the GPR119 receptor, and, therefore, may be used in the treatment of diseases associated with GPR119 receptor activity. Via the activation of GPR119 receptor, the compounds of the present invention may preferably be employed to increase insulin production or increase GLP-1 secretion or both.

Accordingly, the compounds of the present invention can be administered to mammals, preferably humans, for the treatment of a variety of conditions and disorders, including, but not limited to, treating, preventing, or slowing the progression of diabetes and related conditions, microvascular complications associated with diabetes, macrovascular complications associated with diabetes, cardiovascular diseases, Metabolic Syndrome and its component conditions, inflammatory diseases and other maladies. Consequently, it is believed that the compounds of the present invention may be used in preventing, inhibiting, or treating diabetes, hyperglycemia, impaired glucose tolerance, insulin resistance, hyperinsulinemia, retinopathy, neuropathy, nephropathy, wound healing, atherosclerosis and its sequelae (acute coronary syndrome, myocardial infarction, angina pectoris, peripheral vascular disease, intermittent claudication, myocardial ischemia, stroke, heart failure), Metabolic Syndrome, hypertension, obesity, dyslipidemia, hyperlipidemia, hypertriglyceridemia, hypercholesterolemia, low HDL, high LDL, vascular restenosis, peripheral arterial disease, lipid disorders, bone disease (including osteoporosis), PCOS, HIV protease associated lipodystrophy, glaucoma and inflammatory diseases, such as, psoriasis, rheumatoid arthritis and osteoarthritis, and treatment of side-effects related to diabetes, lipodystrophy and osteoporosis from corticosteroid treatment.

Metabolic Syndrome or "Syndrome X" is described in Ford et al., *J. Am. Med. Assoc.*, 287:356-359 (2002) and Arbeeny et al., *Curr. Med. Chem.—Imm., Endoc. & Metab. Agents*, 1:1-24 (2001).

B. Combinations

The present invention includes within its scope the use of pharmaceutical compositions comprising, as an active ingredient, a therapeutically effective amount of at least one of the compounds of Formula I and/or IA, alone or in combination with a pharmaceutical carrier or diluent. The present invention also includes within its scope the use of pharmaceutical compositions comprising, as an active ingredient, a therapeutically effective amount of at least one of the compounds of Formula I and/or IA, alone or in combination with a pharmaceutical carrier or diluent. Optionally, compounds of the present invention can be used alone, in combination with other compounds of the invention, or in combination with one or more other therapeutic agent(s), e.g., an antidiabetic agent or other pharmaceutically active material.

The methods of treatment using compounds of Formula I and/or IA of the present invention may be employed in combination with other GPR119 receptor agonists or one or more other suitable therapeutic agents useful in the treatment of the aforementioned disorders including: anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, appetite suppressants, treatments for heart failure, treatments for peripheral arterial disease and anti-inflammatory agents.

Examples of suitable anti-diabetic agents for use in combination with the compounds of the present invention include insulin and insulin analogs (e.g., LysPro insulin, inhaled formulations comprising insulin); glucagon-like peptides; sulfonylureas and analogs (e.g., chlorpropamide, glibenclamide, tolbutamide, tolazamide, acetohexamide, glypizide, glyburide, glimepiride, repaglinide, meglitinide); biguanides (e.g., metformin, phenformin, buformin); alpha2-antagonists and imidazolines (e.g., midaglizole, isaglidole, deriglidole, idazoxan, efaroxan, fluparoxan); other insulin secretagogues (e.g., linogliride, insulinotropin, exendin-4, N,N-dimethyl-N'-[2-(4-morpholinyl)phenyl]guanidine (E)-2-butenedioate salt (BTS-675820), (−)-N-(trans-4-isopropylcyclohexanecarbonyl)-D-phenylalanine (A-4166)); thiazolidinediones and PPAR-gamma agonists (e.g., ciglitazone, pioglitazone, troglitazone, rosiglitazone); PPAR-alpha agonists e.g., fenofibrate, gemfibrozil); PPAR alpha/gamma dual agonists (e.g., muraglitazar, peliglitazar); SGLT2 inhibitors (e.g., 3-(benzo[b]furan-5-yl)-2',6'-dihydroxy-4'-methylpropiophenone-2'-O-(6-O-methoxycarbonyl)-β-d-glucopyranoside (T-1095 Tanabe Seiyaku), phlorizin, TS-033 (Taisho), dapagliflozin (BMS), sergiflozin (Kissei), AVE 2268 (Sanofi-Aventis)); 11-beta-hydroxysteriod dehydrogenase type I inhibitors (e.g., AMG221, INC1313739); dipeptidyl peptidase-IV (DPP4) inhibitors (e.g., saxagliptin, sitagliptin, vildagliptin, and denagliptin); glucagon-like peptide-1 (GLP-1) receptor agonists (e.g., Exenatide (Byetta™), NN2211 (Liraglutide, Novo Nordisk), AVE0010 (Sanofi-Aventis), R1583 (Roche/Ipsen), SUN E7001 (Daiichi/Santory), GSK-716155 (GSK/Human Genome Sciences) and Exendin-4 (PC-DAC™); aldose reductase inhibitors (e.g., those disclosed in WO 99/26659); RXR agonists (e.g., reglitazar (JTT-501), 5-[[6-[(2-fluorophenyl)methoxy]-2-naphthalenyl]methyl]-2,4-thiazolidinedione (MCC-555), 5-[[3-(5,6,7,8-tetrahydro-3,5,5,8,8-pentamethyl-2-naphthalenyl)-4-(trifluoromethoxy)phenyl]methylene]-2,4-thiazolidinedione (M-6054), DRF2593, farglitazar, (±)-5-[(2,4-dioxothiazolidin-5-yl)methyl]-2-methoxy -N-[[(4-trifluoromethyl)phenyl]methyl]benzamide (KRP-297), 6-[1-(5,6,7,8-tetrahydro-3,5,5,8,8-pentamethyl-2-naphthalenyl)cyclopropyl]-3-pyridinecarboxylic acid (LG100268)); fatty acid oxidation inhibitors (e.g., clomoxir, etomoxir; α-glucosidase inhibitors: precose, acarbose, miglitol, emiglitate, voglibose, 2,6-dideoxy-2,6-imino-7-O-β-D-glucopyranosyl-D-glycero-L-gulo-heptitol (MDL-25,637), camiglibose); beta-agonists (e.g., methyl ester [4-[(2R)-2-[[(2R)-2-(3-chlorophenyl)-2-hydroxyethyl]amino]propyl]phenoxy]-acetic acid (BRL 35135), 2-[4-[(2S)-2-[[(2S)-2-(3-chlorophenyl)-2-hydroxyethyl]amino]propyl]phenoxy]-acetic acid (BRL 37344), 4-[(3R)-3-[bis[(2R)-2-hydroxy-2-phenylethyl]amino]butyl]-benzamide (Ro 16-8714), 2-[4-[2-[[(2S)-2-hydroxy-3-phenoxypropyl]amino]ethoxy]phenoxy]-N-(2-methoxyethyl)-acetamide (ICI D7114), 5-[(2R)-2-[[(2R)-2-(3-chlorophenyl)-2-hydroxyethyl]amino]propyl]-3-benzodioxole-2,2-dicarboxylic acid, disodium salt (CL 316, 243), TAK-667, AZ40140); phosphodiesterase inhibitors, both cAMP and cGMP type (e.g. sildenafil, 9-((1S,2R)-2-fluoro-1-methylpropyl)-2-methoxy-6-(1-piperazinyl)purine hydrochloride (L-686398), L-386,398); amylin agonists (e.g., pramlintide); lipoxygenase inhibitors (e.g., masoprocal); somatostatin analogs (e.g., lanreotide, seglitide, octreotide); glucagon antagonists (e.g., BAY 276-9955); insulin signaling agonists, insulin mimetics, PTP1B inhibitors (e.g., 2-[2-(1,1-dimethyl-2-propenyl)-1H-indol-3-yl]-3,6-dihydroxy-5-[7-(3-methyl-2-butenyl)-1H-indol-3-yl]-2,5-cyclohexadiene-1,4-dione (L-783281), TER17411, TER117529); gluconeogenesis inhibitors (e.g., GP3034); somatostatin analogs and antagonists; antilipolytic agents (e.g., nicotinic acid, acipimox, N-cyclohexyl-2'-O-methyl-adenosine (WAG 994)); glucose transport stimulating agents (e.g., 4-chloro-α-[(4-methylphenyl)sulfonyl]-benzeneheptanoic acid (BM-130795)); glucose synthase kinase inhibitors (e.g., lithium chloride, CT98014, CT98023); galanin receptor agonists; Chemokine receptor antagonist CCR2/5 (e.g., NCB3284, MK-0812, INCB8696, maraviroc (Pfizer) and vicriviroc); thyroid receptor agonists (e.g., KB-2115 (KaroBio)); Glucokinase activators (e.g., RO-27-4375, RO-28-1675 (Roche), 6-[[3-[(1S)-2-methoxy-1-methylethoxy]-5-[(1S)-1-methyl-2-phenylethoxy]benzoyl]amino]-3-pyridinecarboxylic acid (GKA-50 AstraZeneca)); GPR119 agonists (e.g., 1,1-dimethylethyl ester 4-[[3-(4-pyridinyl)-1,2,4-oxadiazol-5-yl]methoxy]-1-piperidinecarboxylic acid (PSN-632408 OSI Prosidion)); GDIR agonists (e.g., APD668 (Arena)); GPR40 modulators (e.g., (S)-4-(dimethylamino)-3-(4-((4-methyl-2-p-tolylthiazol-5-yl)methoxy)phenyl)-4-oxobutanoic acid, 6-chloro-2-(4-chlorobenzylthio)-1-(4-(methoxymethoxyphenyl)-1H-benzo[d]imidazole).

Examples of suitable lipid lowering agents and anti-atherosclerotic agents for use in combination with the compounds of the present invention include one or more MTP/ApoB secretion inhibitors (e.g., dirlopatide, N-(2,2,2-trifluoroethyl)-9-[4-[4-[[[4'-(trifluoromethyl)[1,1'-biphenyl]-2-yl]carbonyl-]amino]-1-piperidinyl]butyl]-9H-fluorene-9-carboxamide, methanesulfonate, CP-741952 (Pfizer), SLx-4090 (Surface Logix)); HMG CoA reductase inhibitors (e.g., atorvastatin, rosuvastatin, simvastatin, pravastatin, lovastatin, fluvastatin); squalene synthetase inhibitors, PPAR alpha agonists and fibric acid derivatives (e.g., fenofibrate, gemfibrozil); ACAT inhibitors; lipoxygenase inhibitors; cholesterol absorption inhibitors (e.g., ezetimibe); thyroid receptor agonists (e.g., as set forth above); Ileal Na+/bile acid cotransporter inhibitors (e.g., compounds as disclosed in Drugs of the Future, 24:425-430 (1999); upregulators of LDL receptor activity (e.g., (3R)-3-[(13R)-13-hydroxy -10-oxotetradecyl]-5,7-dimethoxy-1(3H)-isobenzofuranone (Taisho Pharmaceutical Co. Ltd.) and (3α, 4α,5α)-4-(2-propenyl)-cholestan-3-ol (Eli Lilly); bile acid sequestrants (e.g., WELCHOL®, COLESTID®, LOCHOLEST® and QUESTRAN®; and fibric acid derivatives, such as ATROMID®, LOPID® and TRICOT®); cholesterol ester transfer protein inhibitors (e.g., torcetrapib and (2R)-3-{[3-(4-chloro-3-ethyl-phenoxy)-phenyl]-[[3-(1,1,2,2-tetrafluoroethoxy)phenyl]methyl]amino}-1,1,1-trifluoro-2-propanol); nicotinic acid and derivatives thereof (e.g., niacin, acipimox); PCSK9 inhibitors; LXR agonists (e.g., those disclosed in U.S. Patent Application Publication Nos. 2003/01814206, 2005/0080111, and 2005/0245515); lipoxygenase inhibitors (e.g., such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al., "Attenuation of diet-induced atherosclerosis in rabbits with a highly selective 15-lipoxygenase inhibitor lacking significant antioxidant properties", *Brit. J. Pharmacology*, 120:1199-1206 (1997), and Cornicelli et al., "15-Lipoxygenase and its Inhibition: A Novel Therapeutic Target for Vascular Disease", *Current Pharmaceutical Design*, 5:11-20 (1999)).

Preferred hypolipidemic agents are pravastatin, lovastatin, simvastatin, atorvastatin, fluvastatin, cerivastatin, atavastatin, and rosuvastatin.

Examples of suitable anti-hypertensive agents for use in combination with the compounds of the present invention include beta adrenergic blockers, calcium channel blockers (L-type and T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors (e.g., aliskiren), ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan, and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopeptidase inhibitors (dual NEP-ACE inhibitors) (e.g., omapatrilat and gemopatrilat), nitrates, central alpha agonists (e.g., clonidine), alpha1 blockers (e.g., prazosine), arterial vasodilators (e.g., minoxidil), sympatolytics (e.g., resperine), renin inhibitors (e.g., Aliskiren (Novartis)).

Examples of suitable anti-obesity agents for use in combination with the compounds of the present invention include a cannabinoid receptor 1 antagonist or inverse agonist (e.g., rimonabant, (4S)-3-(4-chlorophenyl)-N-[(4-chlorophenyl) sulfonyl]-4,5-dihydro-N'-methyl-4-phenyl-1H-pyrazole-1-carboximidamide (SLV 319), CP-945598 (Pfizer), Surinabant (SR-147778, Sanofi -Aventis), N-[(1S,2S)-3-(4-chlorophenyl)-2-(3-cyanophenyl)-1-methylpropyl]-2-methyl-2-{[5-(trifluoromethyl)pyridin-2-yl] oxy}propanamide (Merck) and those discussed in Hertzog, D. L., *Expert Opin. Ther. Patents*, 14:1435-1452 (2004)); a beta 3 adrenergic agonist (e.g., rafabegron (AJ9677, Takeda/Dainippon), N-[4-[2-[[(2S)-3-[(6-amino-3-pyridinyl)oxy]-2-hydroxypropyl]amino]ethyl]phenyl]-4-(1-methylethyl)-benzenesulfonamide (L750355, Merck), or CP331648 (Pfizer), or other known beta 3 agonists, as disclosed in U.S. Pat. Nos. 5,541,204, 5,770,615, 5,491,134, 5,776,983, and 5,488,064, with rafabegron, N-[4-[2-[[(2S)-3-[(6-amino-3-pyridinyl)oxy]-2-hydroxypropyl]amino]ethyl]phenyl]-4-(1-methylethyl)-benzenesulfonamide, and CP331648 being preferred); a lipase inhibitor (e.g., orlistat or cetilistat, with orlistat being preferred); a serotonin and norepinephrine reuptake inhibitor (e.g., sibutramine, Abbott and tesofensine, Neurosearch) with sibutramine being preferred; a dopamine reuptake inhibitor (e.g., buproprion, GSK); or 5-HT$_{2C}$ agonist, (e.g., lorcaserin hydrochloride (Arena), WAY-163909 [(7bR,10aR)-1,2,3,4,8,9,10,10a -octahydro-7bH-cyclopenta-[b][1,4]diazepino[6,7,1hi]indole], with lorcaserin hydrochloride being preferred); 5-HT6 receptor antagonists (Suven, Biovitrum, Epix), anti -epileptics topiramate (Johnson & Johnson) and zonisamide, a ciliary neurotrophic factor agonist (e.g., axokine (Regeneron); brain-derived neurotrophic factor (BDNF), orexin antagonists, histamine receptor-3 (H3) modulators, melanin-concentrating hormone receptor (MCHR) antagonists (e.g., GSK-856464 (GlaxoSmithKline), T-0910792 (Amgen)); diacylglycerol acyltransferase (DGAT) inhibitors (e.g., BAY-74-4113 (Bayer)); acetyl-CoA carboxylase (ACC) inhibitors (e.g., N-(4-(4-(4-isopropoxyphenoxy)phenyl)but-3-yn-2-yl)acetamide (A-80040, Abbott), (R) -anthracen-9-yl(3-(morpholine-4-carbonyl)-1,4'-bipiperidin-1'-yl)methanone (CP-640186, Pfizer)), SCD-1 inhibitors as described by Jiang et al., *Diabetes*, 53 (2004), (abs 653-p); amylin receptor agonists (e.g., compounds disclosed in WO 2005/025504); thyroid receptor agonists (e.g., as set forth above); growth hormone secretagogue receptor (GHSR) antagonists (e.g., A-778193 (Abbott), leptin and leptin mimetics (e.g., OB-3 (Aegis/Albany Medical College), leptin analogs A-100 and A-200 (Amgen), CBT-001452 (Cambridge Biotechnology), ML-22952 (Millennium)), PYY receptor agonist (e.g., AC-162352 (Amylin), PYY-3-36 (Emishere), PYY (3-36)NH2 (Unigene)), NPY-Y4 agonists (7TM Pharma WO 2005/089786(A2,A3)-1), NPY-5 antagonists (e.g., NPY5RA-972 (AstraZeneca), GW-594884A (GlaxoSmithKline), J-104870 (Banyu)); MTP/apoB secretion inhibitors (as set forth above), and/or an anorectic agent.

The anorectic agent which may be optionally employed in combination with compounds of the present invention include dexamphetamine, phentermine, phenylpropanolamine, or mazindol, with dexamphetamine being preferred.

Other compounds that can be used in combination with the compounds of the present invention include CCK receptor agonists (e.g., SR-27895B); galanin receptor antagonists; MCR-4 antagonists (e.g., N-acetyl-L-norleucyl-L-glutaninyl-L -histidyl-D-phenylalanyl-L-arginyl-D-tryptophyl-glycinamide, (HP-228); urocortin mimetics, CRF antagonists, and CRF binding proteins (e.g., mifepristone (RU-486), urocortin).

Further, the compounds of the present invention may be used in combination with HIV protease inhibitors, including but not limited to REYATAZ® and KALETRA®.

Examples of suitable memory enhancing agents, anti-dementia agents, or cognition promoting agents for use in combination with the compounds of the present invention include, but are not limited to aricept, razadyne, donepezil rivastigmine, galantamine, memantine, tacrine, metrifonate, muscarine, xanomelline, deprenyl and physostigmine.

Examples of suitable anti-inflammatory agents for use in combination with the compounds of the present invention include, but are not limited to, NSAIDS, prednisone, acetaminophen, aspirin, codeine, fentanyl, ibuprofen, indomethacin, ketorolac, morphine, naproxen, phenacetin, piroxicam, sufentanyl, sunlindac, interferon alpha, prednisolone, methylprednisolone, dexamethazone, flucatisone, betamethasone, hydrocortisone, beclomethasone, remicade, orencia, and enbrel.

The aforementioned patents and patent applications are incorporated herein by reference.

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

What is claimed is:

1. A compound of Formula IA:

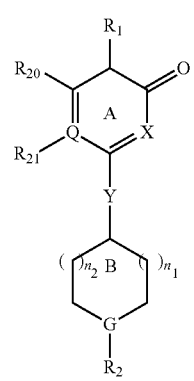

Formula IA and enantiomers, diastereomers and pharmaceutically acceptable salts thereof, wherein:

ring A is optionally substituted with one or more R's shown as $R_{20}$ and $R_{21}$;
G is N;
Q is C;
X is CH;
Y is O;
$n_1$ is 1;
$n_2$ is 1;
$R_1$ is

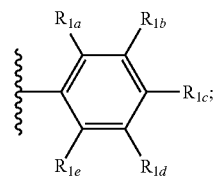

$R_{1a}$, $R_{1b}$, $R_{1d}$ and $R_{1e}$ are each independently selected from the group consisting of hydrogen, halo, CN and $C_{1-3}$ alkyl;
$R_{1c}$ is imidazolyl, oxazolyl or triazolyl;
$R_2$ is pyrimidinyl or —(=O)$OR_5$, wherein the pyrimidinyl may be optionally substituted with $C_{1-3}$ alkyl;
$R_5$ is $C_{1-3}$ alkyl;
$R_{20}$ is hydrogen; and
$R_{21}$ is hydrogen, halo or CN.

2. A compound according to claim 1, wherein the compound is

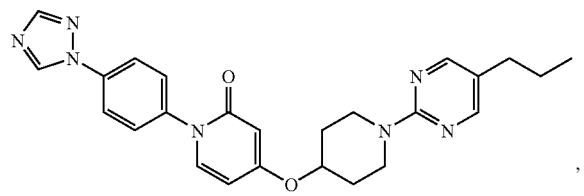

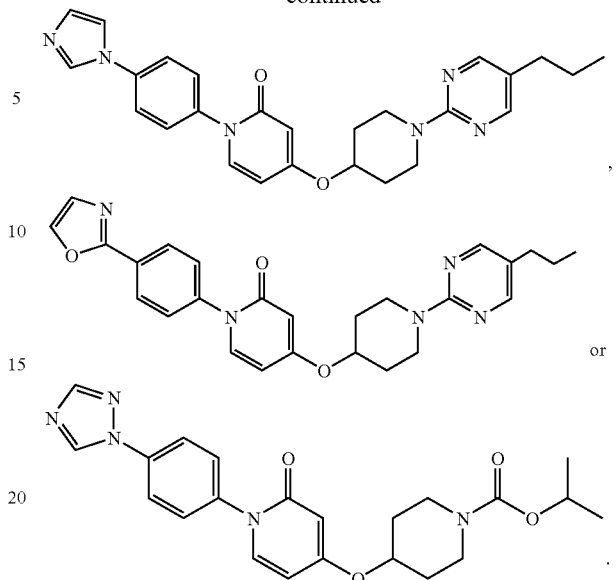

3. A pharmaceutical composition comprising a therapeutically effective amount of a compound of claim 1.

4. The pharmaceutical composition of claim 3, further comprising a pharmaceutically acceptable carrier.

5. The pharmaceutical composition of claim 3, further comprising one or more other therapeutic agent(s).

6. A pharmaceutical composition comprising a therapeutically effective amount of a compound of claim 2.

7. The pharmaceutical composition of claim 6, further comprising a pharmaceutically acceptable carrier.

8. The pharmaceutical composition of claim 6, further comprising one or more other therapeutic agent(s).

* * * * *

UNITED STATES PATENT AND TRADEMARK OFFICE
CERTIFICATE OF CORRECTION

PATENT NO. : 7,928,230 B2  Page 1 of 1
APPLICATION NO. : 12/173864
DATED : April 19, 2011
INVENTOR(S) : Dean Wacker et al.

It is certified that error appears in the above-identified patent and that said Letters Patent is hereby corrected as shown below:

Col. 115, claim 1, line 25 delete " —(=O)OR₅, " and insert -- —C(=O)OR₅, --, therefor.

Signed and Sealed this
Fourteenth Day of August, 2012

David J. Kappos
*Director of the United States Patent and Trademark Office*